US011713463B2

(12) United States Patent
Petrou et al.

(10) Patent No.: US 11,713,463 B2
(45) Date of Patent: Aug. 1, 2023

(54) COMPOSITIONS AND METHODS FOR INCREASING EXPRESSION OF SCN2A

(71) Applicant: The Florey Institute of Neuroscience and Mental Health, Parkville (AU)

(72) Inventors: Steven Petrou, Eltham (AU); Eric G. Marcusson, San Francisco, CA (US)

(73) Assignee: The Florey Institute of Neuroscience and Mental Health, Parkville (AU)

( * ) Notice: Subject to any disclaimer, the term of this patent is extended or adjusted under 35 U.S.C. 154(b) by 0 days.

(21) Appl. No.: 16/962,796

(22) PCT Filed: Jan. 17, 2019

(86) PCT No.: PCT/US2019/014030
§ 371 (c)(1),
(2) Date: Jul. 16, 2020

(87) PCT Pub. No.: WO2019/143831
PCT Pub. Date: Jul. 25, 2019

(65) Prior Publication Data
US 2021/0324386 A1 Oct. 21, 2021

Related U.S. Application Data

(60) Provisional application No. 62/618,473, filed on Jan. 17, 2018.

(51) Int. Cl.
*C12N 15/113* (2010.01)
*A61P 25/00* (2006.01)
*C12Q 1/68* (2018.01)

(52) U.S. Cl.
CPC .......... *C12N 15/1138* (2013.01); *A61P 25/00* (2018.01); *C12N 2310/11* (2013.01); *C12N 2310/314* (2013.01); *C12N 2310/315* (2013.01); *C12N 2310/321* (2013.01); *C12N 2320/34* (2013.01)

(58) Field of Classification Search
None
See application file for complete search history.

(56) References Cited

U.S. PATENT DOCUMENTS

| 9,771,579 | B2 | 9/2017 | Collard et al. |
| 10,793,857 | B2* | 10/2020 | Collard ................. A61P 25/00 |
| 2006/0088827 | A1 | 4/2006 | Hipfel et al. |
| 2015/0232836 | A1* | 8/2015 | Krieg ..................... A61P 35/02 |
| | | | 530/358 |
| 2015/0315579 | A1 | 11/2015 | Bhat et al. |
| 2017/0355990 | A1* | 12/2017 | Collard ..................... A61P 9/12 |
| 2018/0002696 | A1* | 1/2018 | Collard .................. A61P 13/08 |

FOREIGN PATENT DOCUMENTS

| WO | WO 2015/109034 A1 | 7/2015 |
| WO | WO 2016/077837 A1 | 5/2016 |
| WO | WO 2019/040923 A1 | 2/2019 |

OTHER PUBLICATIONS

International Search Report in PCT/US2019/014030 dated May 3, 2019.
Extended European Search Report in European Patent Application No. EP19741442 dated Dec. 13, 2021.
Ogiwara, I., PhD, et al., "De novo mutations of voltage-gated sodium channel an gene SCN2A in intractable epilepsies," Neurology vol. 73: 1046-1053 (2009).
Liang, Xue-Hai, et al., "Chapter 9: Specific Increase of Protein Levels by Enhancing Translation Using Antisense Oligonucleotides Targeting Upstream Open Frames", RNA Activation, Advances in Experimental Medicine and Biology, 983. 2017. (18 pages).
Liang, Xue-Hai, et al., "Antisense oligonucleotides targeting translation inhibitory elements in 5' UTRs can selectively increase protein levels," Nucleic Acids Research, 2017, vol. 45: 9528-9546.

* cited by examiner

*Primary Examiner* — Sean McGarry
(74) *Attorney, Agent, or Firm* — Knobbe, Martens, Olson & Bear, LLP

(57) ABSTRACT

Described herein are compositions and methods that are used to increase the expression of SCN2A, which may be used to treat neurological or psychiatric disorders. Antisense oligonucleotides that target upstream open reading frames (uORFs) may be administered to prevent translation initiation from a uORF to increase expression from a primary ORF (pORF), thus increasing the levels of SCN2A protein.

7 Claims, No Drawings

Specification includes a Sequence Listing.

COMPOSITIONS AND METHODS FOR INCREASING EXPRESSION OF SCN2A

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 34678911_1.TXT, the date of creation of the ASCII text file is Mar. 26, 2021, and the size of the ASCII text file is 81.2 KB.

BACKGROUND OF THE INVENTION

Neurological and psychiatric diseases can arise from mutations or other causes that produce a decrease in expression or activity of key proteins. Loss of function mutations in the SCN2A gene have been causally linked to developmental epileptic encephalopathies (DEEs), autism, and schizophrenia (Howell et al. *Neurology* 85(11) 958-966. 2015; Baasch et al. *Epilepsia* 55(4): e25-e2, 2014; Dhamija et al., *Ped. Neurol.*, 49(6): 486-488 2013: and Nakamura et al. *Neurology* 81(11): 992-998. 2013, Stossman et al., *Nat. Genet.* 49(4): 515-526. 2017). Effective methods for treating such disorders are not currently available. Thus, a need exists for compositions and methods useful for treating various disorders by increasing the expression of the SCN2A gene.

SUMMARY OF THE INVENTION

Disclosed herein are compositions and methods that are used to increase the expression of SCN2A.

In one aspect, the invention features a compound comprising a modified oligonucleotide that is 10-80 nucleosides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides, e.g., 12-40 nucleosides, e g, 16-30 nucleosides, e.g., 16 nucleosides) in length and has a nucleobase sequence with a portion of at least 10 contiguous nucleobases complementary to an equal length portion of a target region of an mRNA transcript upstream of a primary open reading frame (pORF) of a human SCN2A gene, wherein the compound (i) does not decrease mRNA levels by known mechanisms including activation of RNase H or RNA-induced silencing complex (RISC) pathways, and (ii) increases expression of the pORF of the human SCN2A gene.

In some embodiments, the oligonucleotide is complementary to at least one (e.g., ono, two, or three) nucleotide within an AUG codon of any one of SEQ ID NOs: 1-10.

In some embodiments, the oligonucleotide is complementary to a region adjacent (e.g., 1, 2, 3, 4, 5, nucleobases away) to an AUG codon of any one of SEQ ID NOs: 1-10.

In some embodiments, the oligonucleotide has one or more modified sugars. The one or more modified sugars may be independently selected from the group consisting of a bicyclic sugar, a 2'-O-methoxyethyl (2MOE) modified sugar, a 2'-methoxy (2OMe) modified sugar, a 2'-O-alkyl modified sugar, a constrained ethyl (cEt) modified sugar, a locked sugar, and an unlocked sugar. The oligonucleotide may have 2MOE modified sugars throughout the length of the oligonucleotide.

In some embodiments the oligonucleotide has one or more modified internucleoside linkages. The internucleoside linkage may have a modified phosphate. The one or more modified phosphates may be independently selected from the group consisting of, a phosphorothioate, a phosphorodithioate, a phosphoramidate, a phosphorodiamidate, a thiophosphoramidate, a thiophosphorodiamidate, a methyl phosphonate, a phosphoromorpholidate, and a phosphoropiperazidate The oligonucleotide may have phosphorothioate internucleoside linkages throughout the length of the oligonucleotide. The oligonucleotide may have phosphorodiamidate morpholino (PMO) internucleoside linkages throughout the length of the oligonucleotide.

In some embodiments the oligonucleotide has at least one modified nucleobase. The modified nucleobase may be selected from the group consisting of 5-methylcytosine, 5-hydroxymethyl cytosine, xanthine, hypoxanthine, 2-aminoadenine, 6-methyladenine, 6-methylguanine, 2-propyladenine, 2-propylguanine, 2-thiouracil, 2-thiothymine, 2-thiocytosine, 5-halouracil, 5-halocytosine, 5-propynyluracil, 5-propynylcytosine, 6-azouracil, 6-azocytosine, 6-azothymine, 5-uracil (pseudouracil), 4-thiouracil, 8-haloadenine, 8-aminoadenine, 8-thioladenine, 8-thioalkyladenine, 8-hydroxyladenine, 8-haloguanine, 8-aminoguanine, 8-thiolguanine, 8-thioalkylguanine, 8-hydroxylguanine, 5-halouracil, 5-bromouracil, 5-trifluoromethyluracil, 5-halocytosine, 5-bromocytosine, 5-trifluoromethylcytosine, 7-methylguanine, 7-methyladenine, 2-fluoroadenine, 2-aminoadenine, 8-azaguanine, 8-azaadenine, 7-deazaguanine, 7-deazaadenine, 3-deazaguanine, and 3-deazaadenine.

In some embodiments, the oligonucleotide consists of 12 to 40 nucleosides (e.g., 16-30 nucleosides).

In some embodiments, the oligonucleotide has the sequence of any one of SEQ ID NOs: 12-268.

In another aspect, the invention features a pharmaceutical composition comprising the compound of any of the above embodiments and a pharmaceutically acceptable carrier.

In another aspect, the invention features a method of treating an encephalopathy in a subject in need thereof by administering the compound or pharmaceutical composition of any of the above embodiments in an amount and for a duration sufficient to treat the encephalopathy. In some embodiments, the encephalopathy is SCN2A-related.

In another aspect, the invention features a method of treating autism in a subject in need thereof by administering the compound pharmaceutical composition of any of the above embodiments in an amount and for a duration sufficient to treat the autism.

In another aspect, the invention features a method of increasing expression of SCN2A in cells of a subject by administering the compound or pharmaceutical composition of any of the above embodiments in an amount and for a duration sufficient to increase expression of SCN2A.

In some embodiments, the subject has a mutation in the SCN2A gene that reduces SCN2A activity.

In some embodiments, the subject has a mutation (e.g., a known mutation) that reduces SCN2A transcription or translation.

In some embodiments, increased expression of SCN2A provides a therapeutic effect.

DEFINITIONS

As used herein, the term "oligonucleotide" refers to an oligomer or polymer of nucleosides, such as naturally-occurring nucleosides (i.e., adenosine, guanosine, cytidine, 5-methyluridine, or uridine) or modified forms thereof, that are covalently linked to each other through internucleoside linkages. An oligonucleotide may be antisense to a target nucleic acid, such that the oligonucleotide is complementary to the target nucleic acid sequence. A modified form of a nucleoside, or a modified nucleoside, refers to a nucleoside that has at least one change that is structurally distinguishable from a naturally-occurring nucleoside. In some embodiments, a modified nucleoside includes a modified nucleobase and/or a modified sugar.

As used herein, the term "complementary" refers to the capacity for precise pairing between nucleobases, nucleosides, or nucleotides. For example, if a nucleoside at a certain position of an antisense oligonucleotide is capable of hydrogen bonding with a nucleoside at the same position of the target nucleic acid sequence of the antisense oligonucleotide, then the antisense oligonucleotide and its target nucleic acid sequence are considered to be complementary at that position. Complementary nucleic acids may hybridize or anneal to each other (i.e., an antisense oligonucleotide and its target nucleic acid) through hydrogen bonding interactions that occur between complementary nucleobases, nucleosides, or nucleotides. The hydrogen bonding interactions may be Watson-Crick hydrogen bonding or Hoogsteen or reverse Hoogsteen hydrogen bonding. Examples of complementary nucleobase pairs include, but are not limited to, adenine and thymine, cytosine and guanine, and adenine and uracil, which all pair through the formation of hydrogen bonds.

As used herein, the term "nucleobase" refers to a heterocyclic base moiety capable of forming hydrogen bonds with another nucleobase. Nucleobases provide the hydrogen bonding interactions that are needed bind or hybridize one nucleic acid strand to another in a sequence specific manner. A nucleobase may be a naturally occurring nucleobase (i.e., adenine, guanine, cytosine, thymine, or uracil) or a modified nucleobase. Examples of modified nucleobases are described in detail further herein.

As used herein, the term "nucleotide" refers a nucleobase covalently linked to a sugar or analog thereof and a 5' functional moiety (e.g., a phosphorous moiety). In other words, a nucleotide includes a nucleoside and a 5' functional moiety (e.g., a phosphorous moiety) covalently linked to the 5' carbon of the sugar portion of the nucleoside. A 5' functional moiety in a nucleotide refers to a functional group that is covalently attached to the 5' carbon of the sugar and generally serves to connect neighboring nucleotides (i.e., the functional moiety joined to the 5' carbon of the sugar of one nucleoside is covalently linked to the 3' carbon of the sugar of the adjacent nucleoside). An example of a 5' functional moiety is a phosphorous moiety, which refers to a phosphorous-containing functional moiety that is covalently linked to the 5' carbon of the sugar and functions to connect neighboring nucleotides. Examples of phosphorous moieties include, but are not limited to, a phosphate, a phosphorothioate, a phosphorodithioate, a phosphoramidate, a phosphorodiamidate, a thiophosphoramidate, thiophosphorodiamidate, a methyl phosphonate, a phosphoromorpholidate, and a phosphoropiperazidate. The 5' functional moiety (e.g., a phosphorous moiety) of a nucleotide forms part of the internucleoside linkage, which is defined further herein.

A nucleotide may be a naturally-occurring nucleotide or a modified nucleotide. A naturally-occurring nucleotide has a naturally-occurring nucleoside (i.e., adenosine, guanosine, cytidine, 5-methyluridine, or uridine) covalently linked to a phosphate at the 5' carbon of the sugar. A modified nucleotide refers to a nucleotide having at least one change that is structurally distinguishable from a naturally-occurring nucleotide.

As used herein, the term "modified nucleobase" refers to a nucleobase having at least one change from a naturally-occurring nucleobase (i.e., adenine, guanine, cytosine, thymine, or uracil).

As used herein, the term "modified sugar" refers to a sugar having at least one change from a naturally-occurring sugar (i.e., 2'-deoxyribose in DNA or ribose in RNA). In some embodiments, a modified sugar is a pentofuranosyl sugar. In some embodiments, a modified sugar is a locked sugar. In some embodiments, a modified sugar is an unlocked sugar.

As used here, the term "internucleoside linkage" refers to the backbone linkage of the oligonucleotide that connects the neighboring nucleosides. An internucleoside linkage may be a naturally-occurring internucleoside linkage (i.e., a phosphate linkage, also referred to as a 3' to 5' phosphodiester linkage) or a modified internucleoside linkage. As used herein, the term "modified internucleoside linkage" refers to an internucleoside linkage having at least one change from a naturally-occurring internucleoside linkage. Examples of modified internucleoside linkages include, but are not limited to, a phosphorothioate linkage, a phosphorodithioate linkage, a phosphoramidate linkage, a phosphorodiamidate linkage, a thiophosphoramidate linkage, a thiophosphorodiamidate linkage, a phosphoramidate morpholino linkage, a phosphorodiamidate morpholino (PMO) linkage, and a thiophosphoramidate morpholino linkage, and a thiophosphorodiamidate morpholino linkage, which are known in the art and described in, e.g., Bennett and Swayze, *Annu Rev Pharmacol Toxicol.* 50:259-293, 2010.

As used herein, the term "phosphorothioate linkage" refers to a 3' to 5' phosphodiester linkage that has a sulfur atom for a non-bridging oxygen in the phosphate backbone of an oligonucleotide.

As used herein, the term "phosphorodithioate linkage" refers to a 3' to 5' phosphodiester linkage that has two sulfur atoms for non-bridging oxygens in the phosphate backbone of an oligonucleotide.

As used herein, the term "thiophosphoramidate linkage" refers to a 3' to 5' phospho-linkage that has a sulfur atom for a non-bridging oxygen and a NH group as the 3'-bridging oxygen in the phosphate backbone of an oligonucleotide.

As used herein, the term "bicyclic sugar" refers to a modified pentofuranosyl sugar containing two fused rings. For example, a bicyclic sugar may have the 2' ring carbon of the pentofuranose linked to the 4' ring carbon by way of one or more carbons (i.e., a methylene) and/or heteroatoms (i.e., sulfur, oxygen, or nitrogen). An example of a bicyclic sugar is a locked sugar.

As used herein, the term "locked sugar" refers to a pentofuranosyl sugar in which the 2'-oxygen is linked to the 4' ring carbon by way of a carbon (i.e., a methylene) or a heteroatom (i.e., sulfur, oxygen, or nitrogen). In some embodiments, a locked sugar has the 2'-oxygen linked to the 4' ring carbon by way of a carbon (i.e., a methylene). A nucleoside having a locked sugar is referred to as a locked nucleoside.

As used herein, the term "unlocked sugar" refers to an acyclic sugar that has a 2', 3'-seco acyclic structure, where the bond between the 2' carbon and the 3' carbon in a pentofuranosyl ring is absent.

As used herein, the term "subject" refers to a mammal, e.g., a human.

As used herein, the term "pharmaceutical composition" refers to a medicinal or pharmaceutical formulation that contains an active ingredient at a pharmaceutically acceptable purity as well as one or more excipients and diluents to enable the active ingredient suitable for the method of administration.

The pharmaceutical composition includes pharmaceutically acceptable components that are compatible with, for example, a oligonucleotide. The pharmaceutical composition may be in aqueous form, for example, for intravenous or subcutaneous administration or in tablet or capsule form, for example, for oral administration.

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. The pharmaceutically acceptable carrier must provide adequate pharmaceutical stability to the oligonucleotide. The nature of the carrier differs with the mode of administration. For example, for intravenous administration, an aqueous solution carrier is generally used; for oral administration, a solid carrier is preferred.

As used herein, the term "therapeutically effective amount" refers to an amount, e.g., a pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

As used herein, the terms "treatment" or "treating" refer to reducing, decreasing, decreasing the risk of progression, or decreasing the side effects of (e.g., by 1%, 2%, 3%, 4%, 5%, 6%, 7%, 8%, 9%, 10%, 20%, 30%, 40%, 50%, 60%, 70%, 80%, 90%, 95%, 97%, 99%, or about 100%) a particular disease or condition. Reducing, decreasing, decreasing the risk of progression, or decreasing the side effects of are relative to a subject who did not receive treatment, e.g., a control, a baseline, or a known control level or measurement.

As used herein, the term "SCN2A" refers to the human sodium voltage-gated channel alpha subunit 2 gene or protein.

DETAILED DESCRIPTION

Described herein are compositions and methods that are used to increase the expression of SCN2A in order to treat neurological or psychiatric disorders.

Abnormal expression or function of proteins can cause diseases due to the essential roles that proteins play in various biological processes. Some diseases may be associated with decreased levels of protein or decreased activity of functional protein. As a result, regulation of protein expression and/or protein function may provide a potential therapeutic benefit. Additionally, some diseases may not be associated with decreased protein or functional protein levels, but increased protein levels still provide a therapeutic benefit. Accordingly, increasing the level of a specific protein may be a viable therapeutic strategy to treat certain diseases.

Post-transcriptional regulation of gene expression allows cells and organisms to respond to stimuli by changing gene expression patterns. One such post-transcriptional regulation target includes upstream initiation codons, AUG, that are associated with upstream open reading frames (uORFs). uORFs are sequences that start with the initiation codon and are in frame with a termination codon. uORFs can interfere with proper translation of the downstream primary open reading frame (pORF) that encodes the main protein product in the same mRNA. Due to this interference with translation of the main protein product, uORFs correlate with significantly altered protein expression levels. Such altered expression levels can lead to a decrease in targeted protein expression, incorrect protein expression, modification of mutant protein expression, an absence of protein expression, or degradation of transcribed mRNA.

SCN2A is a gene encoding the human voltage-gated sodium channel alpha subunit 2 protein (also referred to as $Na_v1.2$). SCN2A is located on the long (q) arm of human chromosome 2 at position 24.3. Voltage-gated sodium channels are transmembrane glycoprotein complexes consisting of an alpha-subunit with four domains comprising 24 transmembrane segments and one or more regulatory beta subunits. They are involved in the generation and propagation of neuronal and muscular action potentials. SCN2A is heterogeneously expressed in the brain, and mutations, dysfunction, and/or dysregulation of the protein or levels of functional protein are associated with various neurodevelopmental disorders.

Upon transcription of the SCN2A gene, the SCN2A mRNA may be alternatively spliced, resulting in multiple mRNA transcript variants. The SCN2A gene may have a missense or nonsense mutation in one or both alleles. In some instances, a mutation may cause one or both of the SCN2A alleles to not function properly, resulting in a decreased level of functional protein. In some instances, expression of SCN2A may be dysregulated by a primary disorder or a mutation in the gene or a regulatory region, thus resulting in decreased levels of protein or functional protein. In other instances, SCN2A levels are not altered, but increasing levels of functional protein provides a therapeutic effect for a neurological disorder or psychiatric.

Antisense oligonucleotides (ASOs) may be used to increase levels of protein to provide a therapeutic effect. ASOs and methods of use thereof described herein are particularly useful for treating neurological or psychiatric disorders (e.g., disorders related to the SCN2A gene). Upstream open reading frames (uORFs) are found in the 5'UTR region of many human genes and are thought to be a natural regulatory mechanism for reducing protein expression by diverting the translation initiation complex to bind the mRNA at an incorrect location such that SCN2A translation at the pORF occurs less efficiently. The disclosed ASOs typically hybridize to a region that includes a uORF. By binding to and sterically hindering access of the pre-initiation complex (PIC) to a uORF AUG start codon, the antisense oligonucleotide reduces PIC binding and/or translation from that particular start codon. This may function to preferentially direct the PIC/ribosome to the pORF AUG to increase expression of the of the human SCN2A gene.

The ASOs disclosed herein hybridize to a portion of a SCN2A-encoding mRNA, blocking the translation initiation complex from binding the mRNA at a uORF. This may be achieved by hybridizing specifically to at least a portion (e.g., one, two, and three nucleotides) of a uORF AUG start codon. The ASO may be designed so that binding of the ASO to the mRNA does not trigger unwanted reduction in mRNA levels through the RNA-induced silencing complex (RISC) or by way of RNaseH-mediated degradation. Also, when bound to the portion of a SCN2A-encoding mRNA upstream of the pORF, the ASO should not interfere with binding of the translation initiation complex to the pORF. To this end, the ASOs disclosed herein may either be removed from the mRNA, permitting the approaching translation initiation complex to properly bind the pORF, or may ensure that the ASO does not sterically hinder the translation initiation complex from properly binding the pORF.

The methods disclosed herein may be used with any mammal (e.g., a human) having an SCN2A gene, but are particularly useful for treating a human with an encephalopathy or other neurological disorder or condition. Patients with SCN2A encephalopathy, psychiatric disorders, neurological disorders, or conditions associated with SCN2A translational dysregulation (comprising mutation, reduced transcription or translation of SCN2A mRNA, reduced or altered activity of SCN2A) may exhibit a wide range of symptoms including, for example, seizure disorders (e.g., epilepsies), intellectual disability, autism, movement disorders (e.g., dystonia, chorea, dyskinesia, stereotypies), hypotonia, gastrointestinal symptoms, schizophrenia, or other behavioral disorders. More specific examples of seizure disorders include, without limitation, infantile spasms, Ohtahara syndrome, West syndrome, epilepsy of infancy with migrating focal seizures (EIMFS) and Developmental Epileptic Encephalopathy, (DEE). Paradoxically, it appears that mutations that cause both loss and gain of function in SCN2A may result in DEE although autism is widely thought to arise exclusively from loss of function mutations. The ASOs may be administered (e.g., in neuronal cells of a subject) to treat one or more of these neurological disorders. Antisense Oligonucleotides An antisense oligonucleotide (ASO) described herein is an oligomer or polymer of nucleosides that targets and binds specifically to a region of messenger RNA (mRNA) upstream of a primary open reading frame (pORF) of a sodium voltage-gated channel alpha subunit 2 (SCN2A) transcript. The antisense oligonucleotide is complementary to a region of an mRNA transcript. The antisense oligonucleotide may hybridize to at least one (e.g., one, two, or three) nucleotide of an AUG start codon upstream of the primary AUG start codon. The antisense oligonucleotide may hybridize to a region adjacent (e.g., 1, 2, 3, 4, or 5, nucleotides away) to an AUG codon upstream of the primary AUG start codon. The antisense oligonucleotide may have a nucleobase sequence that preferentially hybridizes to an upstream ORF (uORF) at least 20% more (e.g., at least 20%, 30%, 40%, 50%, 60%, 70%, 80%, or 90% more, twice more, or three times more, etc.) than it hybridizes to the pORF under identical conditions.

The ASOs described herein may be 10 to 80 nucleosides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides, e.g., 12-40 nucleosides, e.g., 16-30 nucleosides, e.g., 16 nucleosides) in length and have a nucleobase sequence comprising a portion of at least 10 contiguous nucleobases complementary to an equal length portion of a target region of an mRNA transcript upstream of a primary open reading frame (pORF) of a human SCN2A gene. The ASOs may comprise a nucleoside sequence complementary to at least 10 nucleotides (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleosides, e.g., 12-40 nucleosides, e.g., 16-30 nucleosides, e.g., 16 nucleosides) to any one of SEQ ID NOs: 1-10. The oligomer may have a sequence of about 10-80 nucleosides that is 100% complementary to the target mRNA; however, those of skill in the art will appreciate that the oligonucleotide sequence need not be 100% complementary in order to hybridize to the target mRNA. Rather, some degree of mismatch with the target can be tolerated without substantially interfering with the ability of the ASO to hybridize to the target mRNA. For example, the sequence of about 10-80 nucleosides can have about 1, 2, 3, 4, 5, 6, 7, 8, 9, 10, or more mismatched residues. The sequence may have at least 70% (e.g., 75%, 80%, 85%, 90%, 95%, 97%, 98%, 99%, or 100%) identity to an oligonucleotide complementary to an equal length portion of its target region. Exemplary ASOs targeting the sequence of any one of SEQ ID NOs: 1-9 are shown in Tables 1-19 below.

Based on the mRNA transcript sequences of SEQ ID NOs: 1-9, we designed 16mer ASOs having a length that are 100% complementary to each unique ORF including at least two nucleosides within an AUG start codon upstream of the pORF. The ASOs are shown in Tables 1-19 below, including SEQ ID NOs: 12-268.

TABLE 1

Unique ORF 1

| Name | ASO Sequence | Target Sequence |
| --- | --- | --- |
| Unique ORF 1, construct 1 | ATCCTGCTCCTTTAAT (SEQ ID NO: 12) | AUUAAAGGAGCAGG<u>AU</u> (SEQ ID NO: 269) |
| Unique ORF 1, construct 2 | CATCCTGCTCCTTTAA (SEQ ID NO: 13) | UUAAAGGAGCAGG<u>AUG</u> (SEQ ID NO: 270) |
| Unique ORF 1, construct 3 | TCATCCTGCTCCTTTA (SEQ ID NO: 14) | UAAAGGAGCAGG<u>AUG</u>A (SEQ ID NO: 271) |
| Unique ORF 1, construct 4 | TTCATCCTCCTCCTTT (SEQ ID NO: 15) | AAAGGAGCAGG<u>AUG</u>AA (SEQ ID NO: 272) |
| Unique ORF 1, construct 5 | TTTCATCCTGCTCCTT (SEQ ID NO: 16) | AAGGAGCAGG<u>AUG</u>AAA (SEQ ID NO: 273) |
| Unique ORF 1, construct 6 | TTTTCATCCTGCTCCT (SEQ ID NO: 17) | AGGAGCAGG<u>AUG</u>AAAA (SEQ ID NO: 274) |
| Unique ORF 1, construct 7 | CTTTTCATCCTGCTCC (SEQ ID NO: 18) | GGAGCAGG<u>AUG</u>AAAAG (SEQ ID NO: 275) |

TABLE 2

Unique ORF 2

| Name | ASO Sequence | Target Sequence |
|---|---|---|
| Unique ORF 2, construct 1 | ATAAGAAAGTGCTGAA (SEQ ID NO: 19) | UUCAGCACUUUCUUAU (SEQ ID NO: 276) |
| Unique ORF 2, construct 2 | CATAAGAAAGTGCTGA (SEQ ID NO: 20) | UCAGCACUUUCUUAUG (SEQ ID NO: 277) |
| Unique ORF 2, construct 3 | GCATAAGAAAGTGCTG (SEQ ID NO: 21) | CAGCACUUUCUUAUGC (SEQ ID NO: 278) |
| Unique ORF 2, construct 4 | TGCATAAGAAAGTGCT (SEQ ID NO: 22) | AGCACUUUCUUAUGCA (SEQ ID NO: 279) |
| Unique ORF 2, construct 5 | TTGCATAAGAAAGTGC (SEQ ID NO: 23) | GCACUUUCUUAUGCAA (SEQ ID NO: 280) |
| Unique ORF 2, construct 6 | CTTGCATAAGAAAGTG (SEQ ID NO: 24) | CACUUUCUUAUGCAAG (SEQ ID NO: 281) |
| Unique ORF 2, construct 7 | CCTTGCATAAGAAAGT (SEQ ID NO: 25) | ACUUUCUUAUGCAAGG (SEQ ID NO: 282) |
| Unique ORF 2, construct 8 | TCCTTGCATAAGAAAG (SEQ ID NO: 26) | CUUUCUUAUGCAAGGA (SEQ ID NO: 283) |
| Unique ORF 2, construct 9 | CTCCTTGCATAAGAAA (SEQ ID NO: 27) | UUUCUUAUGCAAGGAG (SEQ ID NO: 284) |
| Unique ORF 2, construct 10 | GCTCCTTGCATAAGAA (SEQ ID NO: 28) | UUCUUAUGCAAGGAGC (SEQ ID NO: 285) |
| Unique ORF 2, construct 11 | AGCTCCTTGCATAAGA (SEQ ID NO: 29) | UCUUAUGCAAGGAGCU (SEQ ID NO: 286) |
| Unique ORF 2, construct 12 | TAGCTCCTTGCATAAG (SEQ ID NO: 30) | CUUAUGCAAGGAGCUA (SEQ ID NO: 287) |
| Unique ORF 2, construct 13 | TTAGCTCCTTGCATAA (SEQ ID NO: 31) | UUAUGCAAGGAGCUAA (SEQ ID NO: 288) |
| Unique ORF 2, construct 14 | TTTAGCTCCTTGCATA (SEQ ID NO: 32) | UAUGCAAGGAGCUAAA (SEQ ID NO: 289) |
| Unique ORF 2, construct 15 | GTTTAGCTCCTTGCAT (SEQ ID NO: 33) | AUGCAAGGAGCUAAAC (SEQ ID NO: 290) |
| Unique ORF 2, construct 16 | TGTTTACCTCCTTGCA (SEQ ID NO: 34) | UGCAAGGAGCUAAACA (SEQ ID NO: 291) |

TABLE 3

Unique ORF 3

| Name | ASO Sequence | Target Sequence |
|---|---|---|
| Unique ORF 3, construct 1 | ATAACACAGAATCCAC (SEQ ID NO: 35) | GUGGAUUCUGUGUUAU (SEQ ID NO: 292) |
| Unique ORF 3, construct 2 | CATAACACAGAATCCA (SEQ ID NO: 36) | UGGAUUCUGUGUUAUG (SEQ ID NO: 293) |
| Unique ORF 3, construct 3 | TCATAACACAGAATCC (SEQ ID NO: 37) | GGAUUCUGUGUUAUGA (SEQ ID NO: 294) |
| Unique ORF 3, construct 4 | ATCATAACACAGAATC (SEQ ID NO: 38) | GAUUCUGUGUUAUGAU (SEQ ID NO: 295) |
| Unique ORF 3, construct 5 | AATCATAACACAGAAT (SEQ ID NO: 39) | AUUCUGUGUUAUGAUU (SEQ ID NO: 296) |
| Unique ORF 3, construct 6 | AAATCATAACACAGAA (SEQ ID NO: 40) | UUCUGUGUUAUGAUUU (SEQ ID NO: 297) |

TABLE 3-continued

Unique ORF 3

| Name | ASO Sequence | Target Sequence |
|---|---|---|
| Unique ORF 3, construct 7 | TAAATCATAACACAGA (SEQ ID NO: 41) | UCUGUGUUAUGAUUUA (SEQ ID NO: 298) |
| Unique ORF 3, construct 8 | GTAAATCATAACACAG (SEQ ID NO: 42) | CUGUGUUAUGAUUUAC (SEQ ID NO: 299) |
| Unique ORF 3, construct 9 | TGTAAATCATAACACA (SEQ ID NO: 43) | UGUGUUAUGAUUUACA (SEQ ID NO: 300) |
| Unique ORF 3, construct 10 | ATGTAAATCATAACAC (SEQ ID NO: 44) | GUGUUAUGAUUUACAU (SEQ ID NO: 301) |
| Unique ORF 3, construct 11 | AATGTAAATCATAACA (SEQ ID NO: 45) | UGUUAUGAUUUACAUU (SEQ ID NO: 302) |
| Unique ORF 3, construct 12 | AAATGTAAATCATAAC (SEQ ID NO: 46) | GUUAUGAUUUACAUUU (SEQ ID NO: 303) |
| Unique ORF 3, construct 13 | AAAATGTAAATCATAA (SEQ ID NO: 47) | UUAUGAUUUACAUUUU (SEQ ID NO: 304) |
| Unique ORF 3, construct 14 | AAAAATGTAAATCATA (SEQ ID NO: 48) | UAUGAUUUACAUUUUU (SEQ ID NO: 305) |
| Unique ORF 3, construct 15 | GAAAAATGTAAATCAT (SEQ ID NO: 49) | AUGAUUUACAUUUUUC (SEQ ID NO: 306) |
| Unique ORF 3, construct 16 | AGAAAAATGTAAATCA (SEQ ID NO: 50) | UGAUUUACAUUUUUCU (SEQ ID NO: 307) |

TABLE 4

Unique ORF 4

| Name | ASO Sequence | Target Sequence |
|---|---|---|
| Unique ORF 4, construct 1 | ATTTCATGACAGGTGA (SEQ ID NO: 51) | UCACCUGUCAUGAAAU (SEQ ID NO: 308) |
| Unique ORF 4, construct 2 | CATTTCATGACAGGTG (SEQ ID NO: 52) | CACCUGUCAUGAAAUG (SEQ ID NO: 309) |
| Unique ORF 4, construct 3 | CCATTTCATGACAGGT (SEQ ID NO: 53) | ACCUGUCAUGAAAUGG (SEQ ID NO: 310) |
| Unique ORF 4, construct 4 | CCTGTCATGAAATGGC (SEQ ID NO: 54) | CCUGUCAUGAAAUGGC (SEQ ID NO: 311) |
| Unique ORF 4, construct 5 | TGCCATTTGATGACAG (SEQ ID NO: 55) | CUGUCAUGAAAUGGCA (SEQ ID NO: 312) |
| Unique ORF 4, construct 6 | CTGCCATTTCATGACA (SEQ ID NO: 56) | UGUCAUGAAAUGGCAG (SEQ ID NO: 313) |
| Unique ORF 4, construct 7 | ACTGCCATTTGATGAC (SEQ ID NO: 57) | GUCAUGAAAUGGCAGU (SEQ ID NO: 314) |
| Unique ORF 4, construct 8 | CACTGCCATTTCATGA (SEQ ID NO: 58) | UCAUGAAAUGGCAGUG (SEQ ID NO: 315) |
| Unique ORF 4, construct 9 | CCACTGCCATTTCATG (SEQ ID NO: 59) | CAUGAAAUGGCAGUGG (SEQ ID NO: 316) |
| Unique ORF 4, construct 10 | TCCACTGCCATTTCAT (SEQ ID NO: 60) | AUGAAAUGGCAGUGGA (SEQ ID NO: 317) |
| Unique ORF 4, construct 11 | TTCCACTGCCATTTCA (SEQ ID NO: 61) | UGAAAUGGCAGUGGAA (SEQ ID NO: 318) |
| Unique ORF 4, construct 12 | TTTCCACTCCCATTTC (SEQ ID NO: 62) | GAAAUGGCAGUGGAAA (SEQ ID NO: 319) |

TABLE 4-continued

Unique ORF 4

| Name | ASO Sequence | Target Sequence |
|---|---|---|
| Unique ORF 4, construct 13 | CTTTCCACTGCCATTT (SEQ ID NO: 63) | AAAUGCAGUGGAAAG (SEQ ID NO: 320) |
| Unique ORF 4, construct 14 | TCTTTCCACTGCCATT (SEQ ID NO: 64) | AAUGGCAGUGGAAAGA (SEQ ID NO: 321) |
| Unique ORF 4, construct 15 | GTCTTTCCACTGCCAT (SEQ ID NO: 65) | AUGGCAGUGGAAAGAC (SEQ ID NO: 322) |
| Unique ORF 4, construct 16 | AGTCTTTCCACTGCCA (SEQ ID NO: 66) | UGGCAGUGGAAAGACU (SEQ ID NO: 323) |

TABLE 5

Unique ORF 5

| Name | ASO Sequence | Target Sequence |
|---|---|---|
| Unique ORF 5, construct 1 | ATGACAGGTGAATGCA (SEQ ID NO: 67) | UGCAUUCACCUGUCAU (SEQ ID NO: 324) |
| Unique ORF 5, construct 2 | CATGACAGGTGAATGC (SEQ ID NO: 68) | GCAUUCACCUGUCAUG (SEQ ID NO: 325) |
| Unique ORF 5, construct 3 | TCATGACAGGTGAATG (SEQ ID NO: 69) | CAUUCACCUGUCAUGA (SEQ ID NO: 326) |
| Unique ORF 5, construct 4 | AUUCACCUGUCAUGAA (SEQ ID NO: 70) | AUUCACCUGUCAUGAA (SEQ ID NO: 327) |
| Unique ORF 5, construct 5 | TTTCATGACAGGTGAA (SEQ ID NO: 71) | UUCACCUGUCAUGAAA (SEQ ID NO: 328) |
| Unique ORF 5, construct 6 | ATTTCATGACAGGTGA (SEQ ID NO: 51) | UCACCUGUCAUGAAAU (SEQ ID NO: 308) |
| Unique ORF 5, construct 7 | CATTTCATGACAGGTG (SEQ ID NO: 52) | CACCUGUCAUGAAAUG (SEQ ID NO: 309) |
| Unique ORF 5, construct 8 | CCATTTCATGACAGGT (SEQ ID NO: 53) | ACCUGUCAUGAAAUGG (SEQ ID NO: 310) |
| Unique ORF 5, construct 9 | CCUGUCAUGAAAUGGC (SEQ ID NO: 54) | CCUGUCAUGAAAUGGC (SEQ ID NO: 311) |
| Unique ORF 5, construct 10 | TGCCATTTCATGACAG (SEQ ID NO: 55) | CUGUCAUGAAAUGGCA (SEQ ID NO: 312) |
| Unique ORF 5, construct 11 | CTGCCATTTCATGACA (SEQ ID NO: 56) | UGUCAUGAAAUGGCAG (SEQ ID NO: 313) |
| Unique ORF 5, construct 12 | ACTGCCATTTCATGAC (SEQ ID NO: 57) | GUCAUGAAAUGGCAGU (SEQ ID NO: 314) |
| Unique ORF 5, construct 13 | CACTGCCATTTCATGA (SEQ ID NO: 58) | UCAUGAAAUGGCAGUG (SEQ ID NO: 315) |
| Unique ORF 5, construct 14 | CCACTGCCATTTCATG (SEQ ID NO: 59) | CAUGAAAUGGCAGUGG (SEQ ID NO: 316) |
| Unique ORF 5, construct 15 | TCCACTGCCATTTCAT (SEQ ID NO: 60) | AUGAAAUGGCAGUGGA (SEQ ID NO: 317) |
| Unique ORF 5, construct 16 | TTCCACTGCCATTTCA (SEQ ID NO: 61) | UGAAAUGGCAGUGGAA (SEQ ID NO: 318) |

TABLE 6

Unique ORF 6

| Name | ASO Sequence | Target Sequence |
|---|---|---|
| Unique ORF 6, construct 1 | ATTCACCTTAGAGGAG (SEQ ID NO: 72) | CUCCUCUAAGGUGAAU (SEQ ID NO: 329) |
| Unique ORF 6, construct 2 | CATTCACCTTAGAGGA (SEQ ID NO: 73) | UCCUCUAAGGUGAAUG (SEQ ID NO: 330) |
| Unique ORF 6, construct 3 | GCATTCACCTTAGAGG (SEQ ID NO: 74) | CCUCUAAGGUGAAUGC (SEQ ID NO: 331) |
| Unique ORF 6, construct 4 | TGCATTCACCTTAGAG (SEQ ID NO: 75) | CUCUAAGGUGAAUGCA (SEQ ID NO: 332) |
| Unique ORF 6, construct 5 | ATGCATTCACCTTAGA (SEQ ID NO: 76) | UCUAAGGUGAAUGCAU (SEQ ID NO: 333) |
| Unique ORF 6, construct 6 | AATGCATTCACCTTAG (SEQ ID NO: 77) | CUAAGGUGAAUGCAUU (SEQ ID NO: 334) |
| Unique ORF 6, construct 7 | AAATGCATTCACCTTA (SEQ ID NO: 78) | UAAGGUGAAUGCAUUU (SEQ ID NO: 335) |
| Unique ORF 6, construct 8 | AAAATGCATTCACCTT (SEQ ID NO: 79) | AAGGUGAAUGCAUUUU (SEQ ID NO: 336) |
| Unique ORF 6, construct 9 | GAAAATGCATTCACCT (SEQ ID NO: 80) | AGGUGAAUGCAUUUUC (SEQ ID NO: 337) |
| Unique ORF 6, construct 10 | AGAAAATGCATTCACC (SEQ ID NO: 81) | GGUGAAUGCAUUUUCU (SEQ ID NO: 338) |
| Unique ORF 6, construct 11 | AAGAAAATGCATTCAC (SEQ ID NO: 82) | GUGAAUGCAUUUUCUU (SEQ ID NO: 339) |
| Unique ORF 6, construct 12 | CAAGAAAATGCATTCA (SEQ ID NO: 83) | UGAAUGCAUUUUCUUG (SEQ ID NO: 340) |
| Unique ORF 6, construct 13 | GCAAGAAAATGCATTC (SEQ ID NO: 84) | GAAUGCAUUUUCUUGC (SEQ ID NO: 341) |
| Unique ORF 6, construct 14 | TCCAAGAAAATGCATT (SEQ ID NO: 85) | AAUGCAUUUUCUUGCA (SEQ ID NO: 342) |
| Unique ORF 6, construct 15 | ATGCAAGAAAATGCAT (SEQ ID NO: 86) | AUGCAUUUUCUUGCAU (SEQ ID NO: 343) |
| Unique ORF 6, construct 16 | AATGCAAGAAAATGCA (SEQ ID NO: 87) | UGCAUUUUCUUGCAUU (SEQ ID NO: 344) |

TABLE 7

Unique ORF 7

| Name | ASO Sequence | Target Sequence |
|---|---|---|
| Unique ORF 7, construct 1 | ATTCTGGTGGATGTGG (SEQ ID NO: 88) | CCACAUCCACCAGAAU (SEQ ID NO: 345) |
| Unique ORF 7, construct 2 | CATTCTGGTGGATGTG (SEQ ID NO: 89) | CACAUCCACCAGAAUG (SEQ ID NO: 346) |
| Unique ORF 7, construct 3 | CCATTCTGGTGGATGT (SEQ ID NO: 90) | ACAUCCACCAGAAUGG (SEQ ID NO: 347) |
| Unique ORF 7, construct 4 | GCCATTCTGGTGGATG (SEQ ID NO: 91) | CAUCCACCAGAAUGGC (SEQ ID NO: 348) |
| Unique ORF 7, construct 5 | AGCCATTCTGGTGGAT (SEQ ID NO: 92) | AUCCACCAGAAUGGCU (SEQ ID NO: 349) |
| Unique ORF 7, construct 6 | TAGCCATTCTGGTGGA (SEQ ID NO: 93) | UCCACCAGAAUGGCUA (SEQ ID NO: 350) |

TABLE 7-continued

Unique ORF 7

| Name | ASO Sequence | Target Sequence |
|---|---|---|
| Unique ORF 7, construct 7 | CCACCAGAATGGCTAC (SEQ ID NO: 94) | CCACCAGA<u>AUG</u>GCUAC (SEQ ID NO: 351) |
| Unique ORF 7, construct 8 | TGTAGCCATTCTGGTG (SEQ ID NO: 95) | CACCAGA<u>AUG</u>GCUACA (SEQ ID NO: 352) |
| Unique ORF 7, construct 9 | TTGTAGCCATTCTGGT (SEQ ID NO: 96) | ACCAGA<u>AUG</u>GCUACAA (SEQ ID NO: 353) |
| Unique ORF 7, construct 10 | GTTGTAGCCATTCTGG (SEQ ID NO: 97) | CCAGA<u>AUG</u>GCUACAAC (SEQ ID NO: 354) |
| Unique ORF 7, construct 11 | AGTTGTAGCCATTCTG (SEQ ID NO: 98) | CAGA<u>AUG</u>GCUACAACU (SEQ ID NO: 355) |
| Unique ORF 7, construct 12 | AAGTTGTAGCCATTCT (SEQ ID NO: 99) | AGA<u>AUG</u>GCUACAACUU (SEQ ID NO: 356) |
| Unique ORF 7, construct 13 | TAAGTTGTAGCCATTC (SEQ ID NO: 100) | GA<u>AUG</u>GCUACAACUUA (SEQ ID NO: 357) |
| Unique ORF 7, construct 14 | TTAAGTTGTAGCCATT (SEQ ID NO: 101) | A<u>AUG</u>GCUACAACUUAA (SEQ ID NO: 358) |
| Unique ORF 7, construct 15 | TTTAAGTTGTAGCCAT (SEQ ID NO: 102) | <u>AUG</u>GCUACAACUUAAA (SEQ ID NO: 359) |
| Unique ORF 7, construct 16 | TTTTAAGTTGTAGCCA (SEQ ID NO: 103) | <u>UG</u>GCUACAACUUAAAA (SEQ ID NO: 360) |

TABLE 8

Unique ORF 8

| Name | ASO Sequence | Target Sequence |
|---|---|---|
| Unique ORF 8, construct 1 | ATCATGCTTTAAAAAA (SEQ ID NO: 104) | UUUUUUAAAGC<u>AUG</u>AU (SEQ ID NO: 361) |
| Unique ORF 8, construct 2 | CATCATGCTTTAAAAA (SEQ ID NO: 105) | UUUUUAAAGC<u>AUG</u>AUG (SEQ ID NO: 362) |
| Unique ORF 8, construct 3 | CCATCATGCTTTAAAA (SEQ ID NO: 106) | UUUUAAAGC<u>AUG</u>AUGG (SEQ ID NO: 363) |
| Unique ORF 8, construct 4 | TCCATCATGCTTTAAA (SEQ ID NO: 107) | UUUAAAGC<u>AUG</u>AUGGA (SEQ ID NO: 364) |
| Unique ORF 8, construct 5 | TTCCATCATGCTTTAA (SEQ ID NO: 108) | UUAAAGC<u>AUG</u>AUGGAA (SEQ ID NO: 365) |
| Unique ORF 8, construct 6 | ATTCCATCATGCTTTA (SEQ ID NO: 109) | UAAAGC<u>AUG</u>AUGGAAU (SEQ ID NO: 366) |
| Unique ORF 8, construct 7 | AATTCCATCATGCTTT (SEQ ID NO: 110) | AAAGC<u>AUG</u>AUGGAAUU (SEQ ID NO: 367) |
| Unique ORF 8, construct 8 | AAATTCCATCATGCTT (SEQ ID NO: 111) | AAGC<u>AUG</u>AUGGAAUUU (SEQ ID NO: 368) |
| Unique ORF 8, construct 9 | AAAATTCCATCATCCT (SEQ ID NO: 112) | AGC<u>AUG</u>AUGGAAUUUU (SEQ ID NO: 369) |
| Unique ORF 8, construct 10 | TAAAATTCCATCATGC (SEQ ID NO: 113) | GC<u>AUG</u>AUGGAAUUUUA (SEQ ID NO: 370) |
| Unique ORF 8, construct 11 | CTAAAATTCCATCATG (SEQ ID NO: 114) | C<u>AUG</u>AUGGAAUUUUAG (SEQ ID NO: 371) |
| Unique ORF 8, construct 12 | GCTAAAATTCCATCAT (SEQ ID NO: 115) | <u>AUG</u>AUGGAAUUUUAGC (SEQ ID NO: 372) |

TABLE 8-continued

Unique ORF 8

| Name | ASO Sequence | Target Sequence |
|---|---|---|
| Unique ORF 8, construct 13 | AGCTAAAATTCCATCA (SEQ ID NO: 116) | UGAUGGAAUUUUAGCU (SEQ ID NO: 373) |
| Unique ORF 8, construct 14 | CAGCTAAAATTCCATC (SEQ ID NO: 117) | GAUGGAAUUUUAGCUG (SEQ ID NO: 374) |
| Unique ORF 8, construct 15 | GCAGCTAAAATTCCAT (SEQ ID NO: 118) | AUGGAAUUUUAGCUGC (SEQ ID NO: 375) |
| Unique ORF 8, construct 16 | TGCAGCTAAAATTCCA (SEQ ID NO: 119) | UGGAAUUUUAGCUGCA (SEQ ID NO: 376) |

TABLE 9

Unique ORF 9

| Name | ASO Sequence | Target Sequence |
|---|---|---|
| Unique ORF 9, construct 1 | ATGCTTTAAAAAAAA (SEQ ID NO: 120) | UUUUUUUUUAAAGCAU (SEQ ID NO: 377) |
| Unique ORF 9, construct 2 | CATGCTTTAAAAAAA (SEQ ID NO: 121) | UUUUUUUUAAACCAUG (SEQ ID NO: 378) |
| Unique ORF 9, construct 3 | TCATGCTTTAAAAAA (SEQ ID NO: 122) | UUUUUUUAAAGCAUGA (SEQ ID NO: 379) |
| Unique ORF 9, construct 4 | ATCATGCTTTAAAAA (SEQ ID NO: 123) | UUUUUUAAACCAUGAU (SEQ ID NO: 380) |
| Unique ORF 9, construct 5 | CATCATGCTTTAAAA (SEQ ID NO: 105) | UUUUUAAAGCAUGAUG (SEQ ID NO: 362) |
| Unique ORF 9, construct 6 | CCATCATGCTTTAAA (SEQ ID NO: 106) | UUUUAAAGCAUGAUGG (SEQ ID NO: 363) |
| Unique ORF 9, construct 7 | TCCATCATGCTTTAA (SEQ ID NO: 107) | UUUAAAGCAUGAUGGA (SEQ ID NO: 364) |
| Unique ORF 9, construct 8 | TTCCATCATGCTTTA (SEQ ID NO: 108) | UUAAAGCAUGAUGGAA (SEQ ID NO: 365) |
| Unique ORF 9, construct 9 | ATTCCATCATGCTTT (SEQ ID NO: 109) | UAAAGCAUGAUGGAAU (SEQ ID NO: 366) |
| Unique ORF 9, construct 10 | AATTCCATCATGCTTT (SEQ ID NO: 110) | AAAGCAUGAUGGAAUU (SEQ ID NO: 367) |
| Unique ORF 9, construct 11 | AAATTCCATCATCCTT (SEQ ID NO: 111) | AAGCAUGAUGGAAUUU (SEQ ID NO: 368) |
| Unique ORF 9, construct 12 | AAAATTCCATCATGCT (SEQ ID NO: 112) | AGCAUGAUGGAAUUUU (SEQ ID NO: 369) |
| Unique ORF 9, construct 13 | TAAAATTCCATCATGC (SEQ ID NO: 113) | GCAUGAUGGAAUUUUA (SEQ ID NO: 370) |
| Unique ORF 9, construct 14 | CTAAAATTCCATCATG (SEQ ID NO: 114) | CAUGAUGGAAUUUUAG (SEQ ID NO: 371) |
| Unique ORF 9, construct 15 | GCTAAAATTCCATCAT (SEQ ID NO: 115) | AUGAUGGAAUUUUAGC (SEQ ID NO: 372) |
| Unique ORF 9, construct 16 | AGCTAAAATTCCATCA (SEQ ID NO: 116) | UGAUGGAAUUUUAGCU (SEQ ID NO: 373) |

TABLE 10

Unique ORF 10

| Name | ASO Sequence | Target Sequence |
|---|---|---|
| Unique ORF 10, construct 1 | ATTAGTCCAGCAGAAC (SEQ ID NO: 124) | GUUCUGCUGGACUA<u>AU</u> (SEQ ID NO: 381) |
| Unique ORF 10, construct 2 | CATTAGTCCAGCAGAA (SEQ ID NO: 125) | UUCUGCUGGACUA<u>AUG</u> (SEQ ID NO: 382) |
| Unique ORF 10, construct 3 | TCATTAGTCCAGCAGA (SEQ ID NO: 126) | UCUGCUGGACUA<u>AUGA</u> (SEQ ID NO: 383) |
| Unique ORF 10, construct 4 | TTCATTAGTCCAGCAG (SEQ ID NO: 127) | CUGCUGGACUA<u>AUG</u>AA (SEQ ID NO: 384) |
| Unique ORF 10, construct 5 | CTTCATTAGTCCAGCA (SEQ ID NO: 128) | UGCUGGACUA<u>AUG</u>AAG (SEQ ID NO: 385) |
| Unique ORF 10, construct 6 | ACTTCATTAGTCCAGC (SEQ ID NO: 129) | GCUGGACUA<u>AUG</u>AAGU (SEQ ID NO: 386) |
| Unique ORF 10, construct 7 | CACTTCATTAGTCCAG (SEQ ID NO: 130) | CUGGACUA<u>AUG</u>AAGUG (SEQ ID NO: 387) |
| Unique ORF 10, construct 8 | GCACTTCATTAGTCCA (SEQ ID NO: 131) | UGGACUA<u>AUG</u>AAGUGC (SEQ ID NO: 388) |
| Unique ORF 10, construct 9 | CCCACTTCATTAGTCC (SEQ ID NO: 132) | GGACUA<u>AUG</u>AAGUGCC (SEQ ID NO: 389) |
| Unique ORF 10, construct 10 | TGGCACTTCATTAGTC (SEQ ID NO: 133) | GACUA<u>AUG</u>AAGUGCCA (SEQ ID NO: 390) |
| Unique ORF 10, construct 11 | GTGGCACTTCATTAGT (SEQ ID NO: 134) | ACUA<u>AUG</u>AAGUGCCAC (SEQ ID NO: 391) |
| Unique ORF 10, construct 12 | AGTGGCACTTCATTAG (SEQ ID NO: 135) | CUA<u>AUG</u>AAGUGCCACU (SEQ ID NO: 392) |
| Unique ORF 10, construct 13 | GAGTGGCACTTCATTA (SEQ ID NO: 136) | UA<u>AUG</u>AAGUGCCACUC (SEQ ID NO: 393) |
| Unique ORF 10, construct 14 | GGAGTGGCACTTCATT (SEQ ID NO: 137) | A<u>AUG</u>AAGUGCCACUCC (SEQ ID NO: 394) |
| Unique ORF 10, construct 15 | TGGAGTGGCACTTCAT (SEQ ID NO: 138) | <u>AUG</u>AAGUGCCACUCCA (SEQ ID NO: 395) |
| Unique ORF 10, construct 16 | GTGGAGTGGCACTTCA (SEQ ID NO: 139) | <u>UG</u>AAGUGCCACUCCAC (SEQ ID NO: 396) |

TABLE 11

Unique ORF 11

| Name | ASO Sequence | Target Sequence |
|---|---|---|
| Unique ORF 11, construct 1 | ATGTGCTCTATCCTCA (SEQ ID NO: 140) | <u>U</u>GAGGAUAGAGCAC<u>AU</u> (SEQ ID NO: 397) |
| Unique ORF 11, construct 2 | CATGTGCTCTATCCTC (SEQ ID NO: 141) | <u>G</u>AGGAUAGAGCAC<u>AUG</u> (SEQ ID NO: 398) |
| Unique ORF 11, construct 3 | ACATGTGCTCTATCCT (SEQ ID NO: 142) | AGGAUAGAGCAC<u>AUG</u>U (SEQ ID NO: 399) |
| Unique ORF 11, construct 4 | GGAUAGAGCACAUGUG (SEQ ID NO: 143) | GGAUAGAGCAC<u>AUG</u>UG (SEQ ID NO: 400) |
| Unique ORF 11, construct 5 | TCACATGTGCTCTATC (SEQ ID NO: 144) | GAUAGAGCAC<u>AUG</u>UGA (SEQ ID NO: 401) |
| Unique ORF 11, construct 6 | CTCACATGTGCTCTAT (SEQ ID NO: 145) | AUAGAGCAC<u>AUG</u>UGAG (SEQ ID NO: 402) |

TABLE 11-continued

Unique ORF 11

| Name | ASO Sequence | Target Sequence |
|---|---|---|
| Unique ORF 11, construct 7 | UAGAGCACAUGUGAGA (SEQ ID NO: 146) | UAGAGCACAUGUGAGA (SEQ ID NO: 403) |
| Unique ORF 11, construct 8 | ATCTGACATGTGCTCT (SEQ ID NO: 147) | AGAGCACAUGUGAGAU (SEQ ID NO: 404) |
| Unique ORF 11, construct 9 | AATCTCACATGTGCTC (SEQ ID NO: 148) | GAGCACAUGUGAGAUU (SEQ ID NO: 405) |
| Unique ORF 11, construct 10 | AAATCTCACATGTGCT (SEQ ID NO: 149) | AGCACAUGUGAGAUUU (SEQ ID NO: 406) |
| Unique ORF 11, construct 11 | AAAATCTCACATGTGC (SEQ ID NO: 150) | GCACAUGUGAGAUUUU (SEQ ID NO: 407) |
| Unique ORF 11, construct 12 | TAAAATCTCACATCTC (SEQ ID NO: 151) | CACAUGUGAGAUUUUA (SEQ ID NO: 408) |
| Unique ORF 11, construct 13 | GTAAAATCTCACATGT (SEQ ID NO: 152) | ACAUGUGAGAUUUUAC (SEQ ID NO: 409) |
| Unique ORF 11, construct 14 | AGTAAAATCTCACATG (SEQ ID NO: 153) | CAUGUGAGAUUUUACU (SEQ ID NO: 410) |
| Unique ORF 11, construct 15 | AAGTAAAATCTCACAT (SEQ ID NO: 154) | AUGUGAGAUUUUACUU (SEQ ID NO: 411) |
| Unique ORF 11, construct 16 | AAAGTAAAATCTCACA (SEQ ID NO: 155) | UGUGAGAUUUUACUUU (SEQ ID NO: 412) |

TABLE 12

Unique ORF 12

| Name | ASO Sequence | Target Sequence |
|---|---|---|
| Unique ORF 12, construct 1 | ATTAAAGAAGAAAAA (SEQ ID NO: 156) | UUUUUUCUUCUUUAAU (SEQ ID NO: 413) |
| Unique ORF 12, construct 2 | CATTAAAGAAGAAAAA (SEQ ID NO: 157) | UUUUUCUUCUUUAAUG (SEQ ID NO: 414) |
| Unique ORF 12, construct 3 | TCATTAAAGAAGAAAA (SEQ ID NO: 158) | UUUUCUUCUUUAAUGA (SEQ ID NO: 415) |
| Unique ORF 12, construct 4 | CTCATTAAAGAAGAAA (SEQ ID NO: 159) | UUUCUUCUUUAAUGAG (SEQ ID NO: 416) |
| Unique ORF 12, construct 5 | CCTCATTAAAGAAGAA (SEQ ID NO: 160) | UUCUUCUUUAAUGAGG (SEQ ID NO: 417) |
| Unique ORF 12, construct 6 | TCCTCATTAAAGAAGA (SEQ ID NO: 161) | UCUUCUUUAAUGAGGA (SEQ ID NO: 418) |
| Unique ORF 12, construct 7 | ATCCTCATTAAAGAAG (SEQ ID NO: 162) | CUUCUUUAAUGAGGAU (SEQ ID NO: 419) |
| Unique ORF 12, construct 8 | TATCCTCATTAAAGAA (SEQ ID NO: 163) | UUCUUUAAUGAGGAUA (SEQ ID NO: 420) |
| Unique ORF 12, construct 9 | CTATCCTCATTAAAGA (SEQ ID NO: 164) | UCUUUAAUGAGGAUAG (SEQ ID NO: 421) |
| Unique ORF 12, construct 10 | TCTATCCTCATTAAAG (SEQ ID NO: 165) | CUUUAAUGAGGAUAGA (SEQ ID NO: 422) |
| Unique ORF 12, construct 11 | CTCTATCCTCATTAAA (SEQ ID NO: 166) | UUUAAUGAGGAUAGAG (SEQ ID NO: 423) |
| Unique ORF 12, construct 12 | GCTCTATCCTCATTAA (SEQ ID NO: 167) | UUAAUGAGGAUAGAGC (SEQ ID NO: 424) |

TABLE 12-continued

Unique ORF 12

| Name | ASO Sequence | Target Sequence |
|---|---|---|
| Unique ORF 12, construct 13 | TGCTCTATCCTCATTA (SEQ ID NO: 168) | UA<u>AUG</u>AGGAUAGACCA (SEQ ID NO: 425) |
| Unique ORF 12, construct 14 | GTGCTCTATCCTCATT (SEQ ID NO: 169) | A<u>AUG</u>AGGAUAGAGCAC (SEQ ID NO: 426) |
| Unique ORF 12, construct 15 | AUGACGAUAGAGCACA (SEQ ID NO: 170) | <u>AUG</u>AGGAUAGAGCAC<u>A</u> (SEQ ID NO: 427) |
| Unique ORF 12, construct 16 | ATGTGCTCTATCCTCA (SEQ ID NO: 140) | <u>UG</u>AGGAUAGAGCAC<u>AU</u> (SEQ ID NO: 397) |

TABLE 13

Unique ORF 13

| Name | ASO Sequence | Target Sequence |
|---|---|---|
| Unique ORF 13, construct 1 | ATCCTCCCTCCTTTGC (SEQ ID NO: 171) | GCAAAGGAGGGAGG<u>AU</u> (SEQ ID NO: 428) |
| Unique ORF 13, construct 2 | CATCCTCCCTCCTTTG (SEQ ID NO: 172) | CAAAGGAGGGAGG<u>AUG</u> (SEQ ID NO: 429) |
| Unique ORF 13, construct 3 | GCATCCTCCCTCCTTT (SEQ ID NO: 173) | AAAGGAGGGAGG<u>AUG</u>C (SEQ ID NO: 430) |
| Unique ORF 13, construct 4 | AGCATCCTCCCTCCTT (SEQ ID NO: 174) | AAGGAGGGAGG<u>AUG</u>CU (SEQ ID NO: 431) |
| Unique ORF 13, construct 5 | CAGCATCCTCCCTCCT (SEQ ID NO: 175) | AGGAGGGAGG<u>AUG</u>CUG (SEQ ID NO: 432) |
| Unique ORF 13, construct 6 | ACAGCATCCTCCCTCC (SEQ ID NO: 176) | GGAGGGAGG<u>AUG</u>CUGU (SEQ ID NO: 433) |
| Unique ORF 13, construct 7 | CACAGCATCCTCCCTC (SEQ ID NO: 177) | GAGGGAGG<u>AUG</u>CUGUG (SEQ ID NO: 434) |
| Unique ORF 13, construct 8 | CCACAGCATCCTCCCT (SEQ ID NO: 178) | AGGGAGG<u>AUG</u>CUGUGG (SEQ ID NO: 435) |
| Unique ORF 13, construct 9 | ACCACAGCATCCTCCC (SEQ ID NO: 179) | GGGAGG<u>AUG</u>CUGUGGU (SEQ ID NO: 436) |
| Unique ORF 13, construct 10 | GGAGGATGCTGTGGTC (SEQ ID NO: 180) | GGAGG<u>AUG</u>CUGUGGUC (SEQ ID NO: 437) |
| Unique ORF 13, construct 11 | TGACCACAGCATCCTC (SEQ ID NO: 181) | GAGG<u>AUG</u>CUGUGGUCA (SEQ ID NO: 438) |
| Unique ORF 13, construct 12 | ATGACCACACCATCCT (SEQ ID NO: 182) | AGG<u>AUG</u>CUGUGGUCAU (SEQ ID NO: 439) |
| Unique ORF 13, construct 13 | GATGACCACAGCATCC (SEQ ID NO: 183) | GG<u>AUG</u>CUGUGGUCAUC (SEQ ID NO: 440) |
| Unique ORF 13, construct 14 | GGATGACCACAGCATC (SEQ ID NO: 184) | G<u>AUG</u>CUGUCCUCAUCC (SEQ ID NO: 441) |
| Unique ORF 13, construct 15 | AGCATGACCACACCAT (SEQ ID NO: 185) | <u>AUG</u>CUGUGGUCAUCCU (SEQ ID NO: 442) |
| Unique ORF 13, construct 16 | AAGGATGACCACAGCA (SEQ ID NO: 186) | <u>UG</u>CUGUGGUCAUCCUU (SEQ ID NO: 443) |

TABLE 14

Unique ORF 14

| Name | ASO Sequence | Target Sequence |
|---|---|---|
| Unique ORF 14, construct 1 | ATTTCCTGTACAGGGA (SEQ ID NO: 187) | UCCCUGUACAGGAAAU (SEQ ID NO: 444) |
| Unique ORF 14, construct 2 | CATTTCCTGTACAGGG (SEQ ID NO: 188) | CCCUGUACAGGAAAUG (SEQ ID NO: 445) |
| Unique ORF 14, construct 3 | GCATTTCCTGTACAGG (SEQ ID NO: 189) | CCUGUACAGGAAAUGC (SEQ ID NO: 446) |
| Unique ORF 14, construct 4 | GGCATTTCCTGTACAG (SEQ ID NO: 190) | CUGUACAGGAAAUGCC (SEQ ID NO: 447) |
| Unique ORF 14, construct 5 | AGGCATTGCCTGTACA (SEQ ID NO: 191) | UGUACAGGAAAUGCCU (SEQ ID NO: 448) |
| Unique ORF 14, construct 6 | GAGGCATTTCCTGTAC (SEQ ID NO: 192) | GUACAGGAAAUGCCUC (SEQ ID NO: 449) |
| Unique ORF 14, construct 7 | AGAGGCAGTTCCTGTA (SEQ ID NO: 193) | UACAGGAAAUGCCUCU (SEQ ID NO: 450) |
| Unique ORF 14, construct 8 | AAGAGGCATTTCCTGT (SEQ ID NO: 194) | ACAGGAAAUGCCUCUU (SEQ ID NO: 451) |
| Unique ORF 14, construct 9 | GAAGAGGCATTTCCTG (SEQ ID NO: 195) | CAGGAAAUGCCUCUUC (SEQ ID NO: 452) |
| Unique ORF 14, construct 10 | AGAAGAGGCATTTCCT (SEQ ID NO: 196) | AGGAAAUGCCUCUUCU (SEQ ID NO: 453) |
| Unique ORF 14, construct 11 | AAGAAGAGGCATTTCC (SEQ ID NO: 197) | GGAAAUGCCUCUUCUU (SEQ ID NO: 454) |
| Unique ORF 14, construct 12 | TAAGAAGAGGCATTTC (SEQ ID NO: 198) | GAAAUGCCUCUUCUUA (SEQ ID NO: 455) |
| Unique ORF 14, construct 13 | GTAAGAAGAGGCATTT (SEQ ID NO: 199) | AAAUGCCUCUUCUUAC (SEQ ID NO: 456) |
| Unique ORF 14, construct 14 | AGTAAGAAGAGGCATT (SEQ ID NO: 200) | AAUGCCUCUUCUUACU (SEQ ID NO: 457) |
| Unique ORF 14, construct 15 | AAGTAAGAAGAGGCAT (SEQ ID NO: 201) | AUGCCUCUUCUUACUU (SEQ ID NO: 458) |
| Unique ORF 14, construct 16 | GAAGTAAGAAGAGGCA (SEQ ID NO: 202) | UGCCUCUUCUUACUUC (SEQ ID NO: 459) |

TABLE 15

Unique ORF 15

| Name | ASO Sequence | Target Sequence |
|---|---|---|
| Unique ORF 15, construct 1 | ATTCGATGGTACCCAA (SEQ ID NO: 203) | UUGGGUACCAUCGAAU (SEQ ID NO: 460) |
| Unique ORF 15, construct 2 | CATTCGATGGTACCCA (SEQ ID NO: 204) | UGCGUACCAUCGAAUG (SEQ ID NO: 461) |
| Unique ORF 15, construct 3 | TCATTCCATGCTACCC (SEQ ID NO: 205) | GGGUACCAUCGAAUGA (SEQ ID NO: 462) |
| Unique ORF 15, construct 4 | GTCATTCCATGGTACC (SEQ ID NO: 206) | CGUACCAUCGAAUGAC (SEQ ID NO: 463) |
| Unique ORF 15, construct 5 | AGTCATTCGATGGTAC (SEQ ID NO: 207) | GUACCAUCGAAUGACU (SEQ ID NO: 464) |
| Unique ORF 15, construct 6 | CAGTCATTCGATGGTA (SEQ ID NO: 208) | UACCAUCGAAUGACUG (SEQ ID NO: 465) |

TABLE 15-continued

Unique ORF 15

| Name | ASO Sequence | Target Sequence |
|---|---|---|
| Unique ORF 15, construct 7 | ACAGTCATTCGATCGT (SEQ ID NO: 209) | ACCAUCGA<u>AUG</u>ACUGU (SEQ ID NO: 466) |
| Unique ORF 15, construct 8 | GACAGTCATTCGATGG (SEQ ID NO: 210) | CCAUCGA<u>AUG</u>ACUGUC (SEQ ID NO: 467) |
| Unique ORF 15, construct 9 | TCACACTCATTCGATG (SEQ ID NO: 211) | CAUCGA<u>AUG</u>ACUGUCA (SEQ ID NO: 468) |
| Unique ORF 15, construct 10 | CTGACAGTCATTCGAT (SEQ ID NO: 212) | AUCGA<u>AUG</u>ACUGUCAG (SEQ ID NO: 469) |
| Unique ORF 15, construct 11 | TCTGACAGTCATTCGA (SEQ ID NO: 213) | UCGA<u>AUG</u>ACUGUCAGA (SEQ ID NO: 470) |
| Unique ORF 15, construct 12 | TTCTGACAGTCATTCG (SEQ ID NO: 214) | CGA<u>AUG</u>ACUGUCAGAA (SEQ ID NO: 471) |
| Unique ORF 15, construct 13 | GTTCTGACAGTCATTC (SEQ ID NO: 215) | GA<u>AUG</u>ACUGUCAGAAC (SEQ ID NO: 472) |
| Unique ORF 15, construct 14 | TGTTCTGACAGTCATT (SEQ ID NO: 216) | A<u>AUG</u>ACUGUCAGAACA (SEQ ID NO: 473) |
| Unique ORF 15, construct 15 | CTGTTCTGACAGTCAT (SEQ ID NO: 217) | <u>AUG</u>ACUGUCAGAACAG (SEQ ID NO: 474) |
| Unique ORF 15, construct 16 | TCTGTTCTGACAGTCA (SEQ ID NO: 218) | <u>UG</u>ACUGUCAGAACAGA (SEQ ID NO: 475) |

TABLE 16

Unique ORF 16

| Name | ASO Sequence | Target Sequence |
|---|---|---|
| Unique ORF 16, construct 1 | ATTATTGTAACTACCA (SEQ ID NO: 219) | UGGUAGUUACAAUA<u>AU</u> (SEQ ID NO: 476) |
| Unique ORF 16, construct 2 | CATTATTGTAACTACC (SEQ ID NO: 220) | GGUAGUUACAAUA<u>AUG</u> (SEQ ID NO: 477) |
| Unique ORF 16, construct 3 | GUAGUUACAAUAAUGC (SEQ ID NO: 221) | GUAGUUACAAUA<u>AUG</u>C (SEQ ID NO: 478) |
| Unique ORF 16, construct 4 | GGCATTATTGTAACTA (SEQ ID NO: 222) | UAGUUACAAUA<u>AUG</u>CC (SEQ ID NO: 479) |
| Unique ORF 16, construct 5 | TGGCATTATTGTAACT (SEQ ID NO: 223) | AGUUACAAUA<u>AUG</u>CCA (SEQ ID NO: 480) |
| Unique ORF 16, construct 6 | ATGGCATTATTGTAAC (SEQ ID NO: 224) | GUUACAAUA<u>AUG</u>CCAU (SEQ ID NO: 481) |
| Unique ORF 16, construct 7 | AATGGCATTATTGTAA (SEQ ID NO: 225) | UUACAAUA<u>AUG</u>CCAUU (SEQ ID NO: 482) |
| Unique ORF 16, construct 8 | AAATGGCATTATTGTA (SEQ ID NO: 226) | UACAAUA<u>AUG</u>CCAUUU (SEQ ID NO: 483) |
| Unique ORF 16, construct 9 | AAAATGGCATTATTGT (SEQ ID NO: 227) | ACAAUA<u>AUG</u>CCAUUUU (SEQ ID NO: 484) |
| Unique ORF 16, construct 10 | CAAAATCGCATTATTG (SEQ ID NO: 228) | CAAUA<u>AUG</u>CCAUUUUG (SEQ ID NO: 485) |
| Unique ORF 16, construct 11 | ACAAAATGCCATTATT (SEQ ID NO: 229) | AAUA<u>AUG</u>CCAUUUUGU (SEQ ID NO: 486) |
| Unique ORF 16, construct 12 | TACAAAATCGCATTAT (SEQ ID NO: 230) | AUA<u>AUG</u>CCAUUUUGUA (SEQ ID NO: 487) |

TABLE 16-continued

Unique ORF 16

| Name | ASO Sequence | Target Sequence |
|---|---|---|
| Unique ORF 16, construct 13 | CTACAAAATGGCATTA (SEQ ID NO: 231) | UA<u>AUG</u>CCAUUUGUAG (SEQ ID NO: 488) |
| Unique ORF 16, construct 14 | ACTACAAAATGGCATT (SEQ ID NO: 232) | A<u>AUG</u>CCAUUUGUAGU (SEQ ID NO: 489) |
| Unique ORF 16, construct 15 | GACTACAAAATGGCAT (SEQ ID NO: 233) | <u>AUG</u>CCAUUUGUAGUC (SEQ ID NO: 490) |
| Unique ORF 16, construct 16 | GGACTACAAAATGGCA (SEQ ID NO: 234) | <u>UG</u>CCAUUUGUAGUCC (SEQ ID NO: 491) |

TABLE 17

Unique ORF 17

| Name | ASO Sequence | Target Sequence |
|---|---|---|
| Unique ORF 17, construct 1 | TGTTAGAAAACAGCAT (SEQ ID NO: 235) | <u>AUG</u>CUGUUUUCUAACA (SEQ ID NO: 492) |
| Unique ORF 17, construct 2 | CTGTTAGAAAACAGCA (SEQ ID NO: 236) | <u>UG</u>CUGUUUUCUAACAG (SEQ ID NO: 493) |

TABLE 18

Unique ORF 18

| Name | ASO Sequence | Target Sequence |
|---|---|---|
| Unique ORF 18, construct 1 | ATATGTCTGAAGCAGC (SEQ ID NO: 237) | GCUGCUUCAGACAU<u>AU</u> (SEQ ID NO: 494) |
| Unique ORF 18, construct 2 | CATATGTCTGAAGCAG (SEQ ID NO: 238) | CUGCUUCAGACAU<u>AUG</u> (SEQ ID NO: 495) |
| Unique ORF 18, construct 3 | ACATATGTCTGAAGCA (SEQ ID NO: 239) | UGCUUCAGACAU<u>AUGU</u> (SEQ ID NO: 496) |
| Unique ORF 18, construct 4 | GACATATGTCTGAAGC (SEQ ID NO: 240) | GCUUCAGACAU<u>AUGUC</u> (SEQ ID NO: 497) |
| Unique ORF 18, construct 5 | AGACATATGTCTGAAG (SEQ ID NO: 241) | CUUCAGACAU<u>AUGUCU</u> (SEQ ID NO: 498) |
| Unique ORF 18, construct 6 | CAGACATATGTCTGAA (SEQ ID NO: 242) | UUCAGACAU<u>AUGUCUG</u> (SEQ ID NO: 499) |
| Unique ORF 18, construct 7 | ACAGACATATGTCTGA (SEQ ID NO: 243) | UCAGACAU<u>AUGUCUGU</u> (SEQ ID NO: 500) |
| Unique ORF 18, construct 8 | CACAGACATATGTCTG (SEQ ID NO: 244) | CAGACAU<u>AUGUCUGUG</u> (SEQ ID NO: 501) |
| Unique ORF 18, construct 9 | ACACAGACATATGTCT (SEQ ID NO: 245) | AGACAU<u>AUGUCUGUGU</u> (SEQ ID NO: 502) |
| Unique ORF 18, construct 10 | CACACAGACATATGTC (SEQ ID NO: 246) | GACAU<u>AUGUCUGUGUG</u> (SEQ ID NO: 503) |
| Unique ORF 18, construct 11 | ACACACAGACATATGT (SEQ ID NO: 247) | ACAU<u>AUGUCUGUGUGU</u> (SEQ ID NO: 504) |
| Unique ORF 18, construct 12 | TACACACAGACATATG (SEQ ID NO: 248) | CAU<u>AUGUCUGUGUGUA</u> (SEQ ID NO: 505) |
| Unique ORF 18, construct 13 | GTACACACAGACATAT (SEQ ID NO: 249) | AU<u>AUGUCUGUGUGUAC</u> (SEQ ID NO: 506) |
| Unique ORF 18, construct 14 | CGTACACACAGACATA (SEQ ID NO: 250) | U<u>AUGUCUGUGUGUACG</u> (SEQ ID NO: 507) |
| Unique ORF 18, construct 15 | GCGTACACACAGACAT (SEQ ID NO: 251) | <u>AUGUCUGUGUGUACGC</u> (SEQ ID NO: 508) |
| Unique ORF 18, construct 16 | AGCGTACACACAGACA (SEQ ID NO: 252) | <u>UGUCUGUGUGUACGCU</u> (SEQ ID NO: 509) |

TABLE 19

Unique ORF 19

| Name | ASO Sequence | Target Sequence |
|---|---|---|
| Unique ORF 19, construct 1 | ATGGATCCCGTAAAAA (SEQ ID NO: 253) | UUUUUACGGGAUCC<u>AU</u> (SEQ ID NO: 510) |
| Unique ORF 19, construct 2 | CATGGATCCCGTAAAA (SEQ ID NO: 254) | UUUUACGGGAUCC<u>AUG</u> (SEQ ID NO: 511) |
| Unique ORF 19, construct 3 | CCATGGATCCCGTAAA (SEQ ID NO: 255) | UUUACGGGAUCC<u>AUGG</u> (SEQ ID NO: 512) |

TABLE 19-continued

Unique ORF 19

| Name | ASO Sequence | Target Sequence |
|---|---|---|
| Unique ORF 19, construct 4 | TCCATGGATCCCGTAA (SEQ ID NO: 256) | UUACGGGAUCCAUGGA (SEQ ID NO: 513) |
| Unique ORF 19, construct 5 | TTCCATGGATCCCGTA (SEQ ID NO: 257) | UACGGGAUCCAUGGAA (SEQ ID NO: 514) |
| Unique ORF 19, construct 6 | ATTCCATGGATCCCGT (SEQ ID NO: 258) | ACGGGAUCCAUGGAAU (SEQ ID NO: 515) |
| Unique ORF 19, construct 7 | AATTCCATGGATCCCG (SEQ ID NO: 259) | CGGGAUCCAUGGAAUU (SEQ ID NO: 516) |
| Unique ORF 19, construct 8 | CAATTCCATGCATCCC (SEQ ID NO: 260) | GGGAUCCAUGGAAUUG (SEQ ID NO: 517) |
| Unique ORF 19, construct 9 | CCAATTCCATGGATCC (SEQ ID NO: 261) | GGAUCCAUGGAAUUGG (SEQ ID NO: 518) |
| Unique ORF 19, construct 10 | ACCAATTCCATGGATC (SEQ ID NO: 262) | GAUCCAUGGAAUUGGU (SEQ ID NO: 519) |
| Unique ORF 19, construct 11 | AACCAATTCCATGGAT (SEQ ID NO: 263) | AUCCAUGGAAUUGGUU (SEQ ID NO: 520) |
| Unique ORF 19, construct 12 | CAACCAATTCCATGGA (SEQ ID NO: 264) | UCCAUGGAAUUGGUUG (SEQ ID NO: 521) |
| Unique ORF 19, construct 13 | CCAACCAATTCCATGG (SEQ ID NO: 265) | CCAUGGAAUUGGUUGG (SEQ ID NO: 522) |
| Unique ORF 19, construct 14 | TCCAACCAATTCCATG (SEQ ID NO: 266) | CAUGGAAUUGGUUGGA (SEQ ID NO: 523) |
| Unique ORF 19, construct 15 | ATCCAACCAATTCCAT (SEQ ID NO: 267) | AUGGAAUUGGUUGGAU (SEQ ID NO: 524) |
| Unique ORF 19, construct 16 | AATCCAACCAATTCCA (SEQ ID NO: 268) | UGGAAUUGGUUGGAUU (SEQ ID NO: 525) |

In any of the antisense oligonucleotides described above, the antisense oligonucleotide may include at least one modified nucleoside. The antisense oligonucleotide may include at least one modified nucleobase (e.g., 5-methylcytosine), at least one modified sugar (e.g., a locked sugar (i.e., a locked sugar that has the 2'-oxygen linked to the 4' ring carbon by way of a methylene)), and/or at least one modified internucleoside linkage (e.g., a phosphorothioate linkage). In certain oligonucleotides, all of the internucleoside linkages are modified (e.g., phosphorothioate) linkages. In certain oligonucleotides, all of the sugars are modified (e.g., with 2MOE modifications).

The antisense oligonucleotides described herein may be covalently linked to one or more moieties or conjugates, which enhance the activity, cellular distribution, and/or cellular uptake of the resulting antisense oligonucleotides. Typical conjugate groups include, but are not limited to, cholesterol moieties and lipid moieties. Other conjugate groups include, but are not limited to, carbohydrates, phospholipids, peptides, antibodies, biotin, phenazine, folate, phenanthridine, anthraquinone, acridine, fluoresceins, rhodamines, coumarins, dyes, and other small molecules. Antisense oligonucleotides described herein may also be modified to have one or more stabilizing groups that are generally attached to one or both termini of antisense oligonucleotides to enhance properties such as, for example, nuclease stability. Stabilizing groups include, for example, cap structures. These terminal modifications protect the antisense oligonucleotide having terminal nucleic acid from exonuclease degradation, and may help in delivery and/or localization of the antisense oligonucleotide within a cell. The cap can be present at the 5'-terminus (5'-cap), or at the 3'-terminus (3'-cap), or can be present on both termini. Cap structures are well-known in the art and include, for example, inverted deoxy abasic caps. Targeting molecules may be attached to the ASO to deliver the ASO to a specific cellular location. For example, the oligonucleotide may be conjugated with an antibody targeting a neuronal cell marker.

SCN2A mRNA Transcripts

Alternative splicing of the SCN2A gene results in multiple mRNA transcript variants. We identified 10 exemplary predicted transcript variant sequences. Shown below (SEQ ID NOs: 1-10) are the 5' untranslated regions (UTRs) upstream of the pORF for each mRNA variant. All AUG start codons are bold and underline. The AUG of the pORF is also italicized.

>mRNA transcript 1
(SEQ ID NO: 1)
CAUCCAUAGAUCUACCAAAAGAUUCCCAGACUCUGGCCCAAUUUUCUUGUUUCCUAGACCAUUAUUUCCC

ACACACUCAUUCCACCAAUACUACUGUUCUCCUCGACUAAUGAAGUCCCACUCCACAUCCACCAGA*AUG*C

CUACAACUUAAAAAGGCUUAUCAUACUGUUUGUGAGAAUCUAGAGCUACAGAAGCUGUCAGAGACUUCAG

CACUUUCUUAUGCAAGGAGCUAAACAGUGAUUAAAGGAGCAGGAUGAAAG*AUG*

>mRNA transcript 2
(SEQ ID NO: 2)
CUACCAGAAGUUCCUUUUUUCUCCAUUUCUUCUGGCAGUUACAGAAUCCUCUUGGGGCUUUCUUAGAGCC AAUCUCCUCUAAGGUGAAUGCAUUUUCUUGCAUUCACCUGUCAUGAAAUGGCAGUGGAAAGACUUGAGA AGGCACAGGCGUUGCACUUUCUUAUGCAAGGAGCUAAACAGUGAUUAAAGGAGCAGGAUGAAAG*AUG*

>mRNA transcript 3
(SEQ ID NO: 3)
AUUUUUCUAAUUUAGCAUGCUGUUUUCUAACAGACAUUGGGUACCAUCGAAUGACUGUCAGAACAGAAAG

CUAAGGCAAAGGAGGGAGCAUGCUGUGGUCAUCCUUUCUUGUUUUUUUCUUCUUUAAUGAGGAUAGAGCA

CAUGUGAGAUUUUACUUUCUACUCCAGUAAAAAUUCUGAAGAAUUGCAUUGGAGACUGUUUAUAUUCAACA

CAUACGUGGAUUCUGUGUUAUGAUUUACAUUUUUCUUUAUUUCAGCACUUUCUUAUGCAAGGAGCUAAAC

AGUGAUUAAAGGAGCAGGAUGAAAG*AUG*

>mRNA transcript 4
(SEQ ID NO: 4)
CACUUUCUUAUGCAAGGAGCUAAACAGUGAUUAAAGGAGCAGGAUGAAAG*AUG*

>mRNA transcript 5
(SEQ ID NO: 5)
AUGCUGUUUUCUAACAGACAUUGGGUACCAUCGAAUGACUGUCAGAACAGAAAGCUAAGGCAAAGGAGGG AGGAUGCUGUGGUCAUCCUUUCUUGUUUUUUUCUUCUUUAAUGAGGAUAGAGCACAUGUGAGAUUUUACU

UUCUACUCGAGUAAAAAUUCUGAAGAAUUGCAUUGGAGACUGUUAUAUUCAACACAUACGUGGAUUCUGU

GUUAUGAUUUACAUUUUUCUUUAUUUCAGCACUUUCUUAUGCAAGGAGCUAAACAGUGAUUAAAGGAGCA

GGAUGAAAAC*AUG*

>mRNA transcript 6
(SEQ ID NO: 6)
GGCUGCUUCAGACAUAUGUCUGUGUGUACGCUGUGAAGGUGUUUCUCUUCACAGUUCCCCGCCCUCUAGU

CCUACUUACAAUAAUGCCAUUUUGUACUCCCUGUACACGAAAUGCCUCUUCUUACUUUCACUUACCACAAU

CCUUUUACAGGAAGUUAGGUGUGGUCUUUGAAGGAGAAUUAAAAAAAAAAAAAAAAAAAAAAAAAAAAGA

UUUUUUUUUUUUAAAGCAUGAUGGAAUUUUAGCUGCAGUCUUGUUGGUGCCAGCUUAUCAAUCCCAAAC

UCUGGGUGUAAAAGAUUCUACAGGGCACUUUCUUAUGCAAGGAGCUAAACAGUGAUUAAAGGAGCAGGAU

GAAAAC*AUG*

>mRNA transcript 7
(SEQ ID NO: 7)
AAAAAAAAAAGAUUUUUUUUUUUUAAAGCAUGAUGGAAUUUUAGCUGCAGUCUUCUUGGUGCCAGCUUA

UCAAUCCCAAACUCUGGGUGUAAAAGAUUCUACAGGGCACUUUCUUAUGCAAGGAGCUAAACAGUGAUUA

AAGGAGCAGGAUGAAAG*AUG*

>mRNA transcript 8
(SEQ ID NO: 8)
UUUCUAACAGACAUUGGGUACCAUCGAAUGACUGUCAGAACAGAAAGCUAAGGCAAAGGAGGGAGGAUGC

UGUGGUCAUCCUUUCUUGUUUUUUUCUUCUUUAAUGAGCAUACAGCACAUGUCAGAUUUUACUUUCUACU

CCAGUAAAAAUUCUCAACAAUUGCAUUGGAGACUGUUAUAUUCAACACAUACCUGGAUUCUGUCUUAUGA

UUUACAUUUUUCUUUAUUUCAGCACUUUCUUAUGCAAGGAGCUAAACAGUGAUUAAAGGAGCAGGAUGAA

AAG*AUG*

>mRNA transcript 9
(SEQ ID NO: 9)
AAAUACUUCCAACCCCCUUUUCUUUACAACAUUUCACAUUUUUACCCCAUCCAUGCAAUUCCUUCCAUUU

CACAGUCAUUACUUUUGCGCCUGAAGACCAUUGUGGGGGCCCUGAUCCAGUCAGUGAAGAAGCUUUCUGA

UGUC*AUG*

```
>mRNA transcript 10
                                                          (SEQ ID NO: 10)
CGUCACAGUUACUUGGUGCUUUGGUAAUGAUGAAAAAACACUUCAUAAAUUUCAAUAAAAUACUUCCUGA

CUUGAUAUUGUAUCAUUAUUACACAUUUUACUAAAUAACAGUAAAAUCCGUGCAUAACUCAUGGAUUCUA

UUAUCUUCCACAGAUUUUUUUUUUUAUAUUUAGCCUCCAGAAAGCOGCUGCAAAUGUAAGGUAUAUUUU

GAACACCACUUUCAUACAUUAAAUUCUAAACAUUGAAACUUGUGUGCAUGACGUUGAAAAGAGUGUAAUG

AUAAAUGCUUAUACUUAUGAUGAUGCUAAGCCAUUUGGAUUAUAUUAACUGCUUGAGACACAAGUUAUAA

AAUCCUAUGACUUAACCAGAAAUAUAAAUUAAAAAUGUGAAUUAGGGUUUGAUAUUAACUUCCUUGAAGC

AAAGUGUUUAAAAUUUUGUAGUCCUACUUUUGCCUUUCUCUGACCAGAUUCUUACAAUAUAUCAGCUUUC

UCUUUAGUUGCAGAUUUUAUCUGAAUAGUUAACAUAAUGUGUAGCAGUCUGGAUCUCAGAAUGCCAAAAU

AAAGACUUUGGGGACAGCUUAAUCUGUGAUCAAUUUCUGGCUCUGCCAUAUGUUAAAUGUGUUAAUUUGU

GACUUUGAAUUUCAGUCUCCUCAUCAGUAAAAUGUGGAUGAUGAUGUUUAGGCAUAAGGUUGUUGAAUGG

AUUAAAUAAGCCUUCUUAGAUAAAACACUGAUGUAUUUGGCAUGCAGAAGACAGUUAAUAAAUAUUAUCA

AUAUUAGUUGUUUUGUUGUUGUUAUUUUUGUUAAUUCACAUGUUUUUGCCUUUCCAUACUGUAAGUGAAU

UCAAACAACUGUCAACUUCAACUACUUGGAAAAUAUUUUCAUGUAAAAUGUAUUCUAUCCCCCUUCCUUG

CCCUCCUAUUGCCUCCUCUCCCUAUCUCUUUACAAACCUUCUCGCUUGUACCCCUUCCCAGGUAUGUGUG

UGAGUGUGAGUGUGUGUAGAUGUGUCAAGGGAGAAGAGAAAAGGAGAAUGAAAGCAAAAGAGAGCAAGCA

UACACGUCCCUUUCUUAUUGAUAAUUAGAUUUUCUCUUGAGAUUGGAUAGAUUCCUGGAAUAAUUCUUUU

CCUGUCUGUAUGCAAAGAUCCCAUAAUAUUAUUAAUACCAAUACGAAAAGCCUGAAAAUCACAGCCAGAA

AAAAUUCACAGUGUAGACGACUGUGUACAUCACAGACAAGUCAGUAUUACAAAACCCAAUUUUCAUAGUG

UCCUAUUUGAGUAUCCUAAUGGAAUUCACUGAUUUCAAUUGAAUAUUAAACUCUAGUACGUUCUUCCCCA

ACCUCGCCUCCCUUACCUUCCACUCCCUCUUCCCCCAGCUGCCACUACCUUCCUCCUCCCUCUCCCUCC

AGGUAAAUGUUUUGAAGAUUGUCUGGCCUUCCGCUCCUUGCCAUAGCAAAACCACUGAGAGGAAGCUGCC

AGUGGUUCUGCUACCGAUGUCAGCAGCAUGUCUGCUCCCUAAAGCAGGAAGUAGAGAAGGAGACAGGAAC

UUGAAGAAUCCAGACAGAAAUGCCCACCAUGCUGGUAUAAAUUUGCUAAUAUG
```

One of ordinary skill in the art can perform sequencing analysis by routine methods (e.g., RT-PCR, RNASeq) to identify variant SCN2A mRNA transcripts (e.g., from alternative splicing variants) that may be used to design antisense oligonucleotides in conjunction with the compositions and methods of the invention as described herein.

Modified Nucleobases

A modified nucleobase (or base) refers to a nucleobase having at least one change that is structurally distinguishable from a naturally-occurring nucleobase (i.e., adenine, guanine, cytosine, thymine, or uracil). A modified nucleobase may be functionally interchangeable with its naturally-occurring counterpart. Both naturally-occurring and modified nucleobases are capable of hydrogen bonding. Modifications on modified nucleobases may help to improve the stability of the antisense oligonucleotides to nucleases, increase binding affinity of the antisense oligonucleotides to their target nucleic acids, and decrease off-target binding of the antisense oligonucleotides. An antisense oligonucleotide described herein may include at least one modified nucleobase. Examples of modified nucleobases include, but are not limited to, 5-methylcytosine, 5-hydroxymethyl cytosine, xanthine, hypoxanthine, 2-aminoadenine, 6-methylguanine, 6-methylguanine, 2-propyladenine, 2-propylguanine, 2-thiouracil, 2-thiothymine, 2-thiocytosine, 5-halouracil, 5-halocytosine, 5-propynyluracil, 5-propynylcytosine, 6-azouracil, 6-azocytosine, 6-azothymine, 5-uracil (pseudouracil), 4-thiouracil, 8-haloadenine, 8-aminoadenine, 8-thioladenine, 8-thioalkyladenine, 8-hydroxyladenine, 8-haloguanine, 8-aminoguanine, 8-thiolguanine, 8-thioalkylguanine, 8-hydroxylguanine, 5-halouracil, 5-bromouracil, 5-trifluoromethyluracil, 5-halocytosine, 5-bromocytosine, 5-trifluoromethylcytosine, 7-methylguanine, 7-methyladenine, 2-fluoroadenine, 2-aminoadenine, 8-azaguanine, 8-azaadenine, 7-deazaguanine, 7-deazaadenine, 3-deazaguanine, and 3-deazaadenine. An antisense oligonucleotide described herein may have one or more modified nucleobases (e.g., 5-methylcytosine).

Modified Sugars

A modified sugar refers to a sugar having at least one change that is structurally distinguishable from a naturally-occurring sugar (i.e., 2'-deoxyribose in DNA or ribose in RNA). Modifications on modified sugars may help to improve the stability of the antisense oligonucleotides to nucleases, increase binding affinity of the antisense oligonucleotides to their target nucleic acids, and decrease off-target binding of the antisense oligonucleotides. The sugar may be a pentofuranosyl sugar. The pentofuranosyl sugar ring of a nucleoside may be modified in various ways including, but not limited to, addition of a substituent group, particularly, at the 2' position of the ring; bridging two non-geminal ring atoms to form a bicyclic sugar (i.e., a locked sugar); and substitution of an atom or group such as —S—, —N(R)— or —C(R$_1$)(R$_2$) for the ring oxygen. Examples of modified sugars include, but are not limited to, substituted sugars, especially 2'-substituted sugars having a 2'-F, 2'-OCH$_2$ (2'-OMe), or a 2'-O(CH$_2$)$_2$OCH$_3$ (2'-O-methoxyethyl or 2'-MOE) substituent group; and bicyclic sugars. A bicyclic sugar refers to a modified pentofuranosyl sugar containing two fused rings. For example, a bicyclic sugar may have the 2' ring carbon of the pentofuranose linked to the 4' ring carbon by way of one or more carbons (i.e., a methylene) and/or heteroatoms (i.e., sulfur, oxygen, or nitrogen). The second ring in the sugar limits the flexibility of the sugar ring and thus, constrains the oligonucleotide in a conformation that is favorable for base pairing interactions with its target nucleic acids. An example of a bicyclic sugar is a locked sugar, which is a pentofuranosyl sugar having the 2'-oxygen linked to the 4' ring carbon by way of a carbon (i.e., a methylene) or a heteroatom (i.e., sulfur, oxygen, or nitrogen). In some embodiments, a locked sugar has the 2'-oxygen linked to the 4' ring carbon by way of a carbon (i.e., a methylene). In other words, a locked sugar has a 4'-(CH$_2$)—O-2' bridge, such as α-L-methyleneoxy (4'-CH$_2$—O-2') and β-D-methyleneoxy (4'-CH$_2$—O-2'). A nucleoside having a lock sugar is referred to as a locked nucleoside.

Other examples of bicyclic sugars include, but are not limited to, (6'S)-6' methyl bicyclic sugar, aminooxy (4'-CH$_2$—O—N(R)-2') bicyclic sugar, oxyamino (4'-CH$_2$—N(R)—O-2') bicyclic sugar, wherein R is, independently, H, a protecting group or C1-C12 alkyl. The substituent at the 2' position can also be selected from allyl, amino, azido, thio, O-allyl, O—C1-C10 alkyl, OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), wherein each R$_m$ and R$_n$ is, independently, H or substituted or unsubstituted C1-C10 alkyl.

The modified sugar may be an unlocked sugar. An unlocked sugar refers to an acyclic sugar that has a 2', 3'-seco acyclic structure, where the bond between the 2' carbon and the 3' carbon in a pentofuranosyl ring is absent.

Modified Internucleoside Linkages

An internucleoside linkage refers to the backbone linkage that connects the nucleosides. An internucleoside linkage may be a naturally-occurring internucleoside linkage (i.e., a phosphate linkage, also referred to as a 3' to 5' phosphodiester linkage, which is found in DNA and RNA) or a modified internucleoside linkage. A modified internucleoside linkage refers to an internucleoside linkage having at least one change that is structurally distinguishable from a naturally-occurring internucleoside linkage. Modified internucleoside linkages may help to improve the stability of the antisense oligonucleotides to nucleases and enhance cellular uptake.

Examples of modified internucleoside linkages include, but are not limited to, a phosphorothioate linkage, a phosphorodithioate linkage, a phosphoramidate linkage, a phosphorodiamidate linkage, a thiophosphoramidate linkage, a thiophosphorodiamidate linkage, a phosphoramidate morpholino linkage, and a thiophosphoramidate morpholino linkage, and a thiophosphorodiamidate morpholino linkage, which are known in the art and described in, e.g., Bennett and Swayze, *Annu Rev Pharmacol Toxicol.* 50:259-293, 2010. A phosphorothioate linkage is a 3' to 5' phosphodiester linkage that has a sulfur atom for a non-bridging oxygen in the phosphate backbone of an oligonucleotide. A phosphorodithioate linkage is a 3' to 5' phosphodiester linkage that has two sulfur atoms for non-bridging oxygens in the phosphate backbone of an oligonucleotide. A thiophosphoramidate linkage refers to a 3' to 5' phospho-linkage that has a sulfur atom for a non-bridging oxygen and a NH group as the 3'-bridging oxygen in the phosphate backbone of an oligonucleotide. In some embodiments, an antisense oligonucleotide described herein has at least one phosphorothioate linkage. In some embodiments, all of the internucleoside linkages in an antisense oligonucleotide described herein are phosphorothioate linkages.

Pharmaceutical Compositions and Preparations

The invention features pharmaceutical compositions that include an antisense oligonucleotide described herein. In addition to the antisense oligonucleotide, the pharmaceutical compositions may contain one or more pharmaceutically acceptable carriers or excipients, which can be formulated by methods known to those skilled in the art. A pharmaceutical composition of the present invention may include an antisense oligonucleotide in a therapeutically effective amount. The therapeutically effective amount of the antisense oligonucleotide may be sufficient to prevent, alleviate, or ameliorate symptoms of a disease or to prolong the survival of the subject being treated. Determination of a therapeutically effective amount is within the capability of those skilled in the art.

Antisense oligonucleotides may be mixed with pharmaceutically acceptable active and/or inert substances for the preparation of pharmaceutical compositions. Compositions and methods for the formulation of pharmaceutical compositions are dependent upon a number of criteria, including, but not limited to, route of administration, extent of disease, or dose to be administered. An antisense oligonucleotide targeted to a uORF of the SCN2A gene can be utilized in pharmaceutical compositions by combining the antisense oligonucleotide with a suitable pharmaceutically acceptable diluent or carrier. A pharmaceutically acceptable diluent includes phosphate-buffered saline (PBS). PBS is a diluent suitable for use in compositions to be delivered parenterally.

Pharmaceutical compositions including antisense oligonucleotides encompass any pharmaceutically acceptable salts or esters thereof, which, upon administration to a mammal (e.g., a human), is capable of providing (directly or indirectly) the biologically active form of the antisense oligonucleotide. Accordingly, for example, the disclosure is also drawn to pharmaceutically acceptable salts of antisense oligonucleotides, prodrugs, pharmaceutically acceptable salts of such prodrugs, and other bioequivalents. Suitable pharmaceutically acceptable salts include, but are not limited to, sodium and potassium salts. A prodrug may include the incorporation of additional nucleosides or nucleotides at one or both ends of an antisense oligonucleotide which are cleaved by endogenous nucleases within the body, to form the active antisense oligonucleotide.

Pharmaceutical compositions of the present invention may include one or more oligonucleotides and one or more pharmaceutically acceptable carriers or excipients. Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. In some embodiments, carriers and excipients are selected from water, salt solutions, alcohol, polyethylene glycols, gelatin, lactose, amylase, magnesium stearate, talc, silicic acid, viscous paraffin, hydroxymethylcellulose, and polyvinylpyrrolidone. A pharmaceutical composition of the present invention may include a co-solvent system. Examples of co-solvent systems include, but are not limited to, benzyl alcohol, a nonpolar surfactant, a water-miscible organic polymer, and an aqueous phase. Such co-solvent systems may be used for hydrophobic compounds. A non-limiting example of such a co-solvent system is the VPD co-solvent system, which is a solution of absolute ethanol including 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

A pharmaceutical composition of the present invention may be prepared using known techniques, including, but not limited to mixing, dissolving, granulating, dragee-making, levigating, emulsifying, encapsulating, entrapping, and tabletting processes. In some embodiments, a pharmaceutical composition of the present invention is a liquid (e.g., a suspension, elixir and/or solution). A liquid pharmaceutical composition may be prepared using ingredients known in the art, including, but not limited to, water, glycols, oils, alcohols, flavoring agents, preservatives, and coloring agents. A pharmaceutical composition of the present invention may be a solid (e.g., a powder, tablet, and/or capsule). A solid pharmaceutical composition including one or more oligonucleotides may be prepared using ingredients known in the art, including, but not limited to, starches, sugars, diluents, granulating agents, lubricants, binders, and disintegrating agents. A pharmaceutical composition of the present invention may be formulated as a depot preparation. In general, depot preparations are typically longer acting than non-depot preparations. Such preparations may be administered by implantation (for example subcutaneously or intramuscularly) or by intramuscular injection. Depot preparations may be prepared using suitable polymeric or hydrophobic materials (for example an emulsion in an acceptable oil) or ion exchange resins, or as sparingly soluble derivatives, for example, as a sparingly soluble salt.

A pharmaceutical composition of the present invention may include a delivery system. Examples of delivery systems include, but are not limited to, exosomes, liposomes, and emulsions. Antisense oligonucleotides described herein may be loaded or packaged in exosomes that specifically target a cell type, tissue, or organ to be treated. Exosomes are small membrane-bound vesicles of endocytic origin that are released into the extracellular environment following fusion of mutivesicular bodies with the plasma membrane. Exosome production has been described for many immune cells including B cells, T cells, and dendritic cells. Techniques used to load a therapeutic compound (e.g., an antisense oligonucleotide described herein) into exosomes are known in the art and described in, e.g., U.S. Patent Publication Nos. US 20130053426 and US 20140348904, and International Patent Publication No. WO 2015/002956, which are incorporated herein by reference. Therapeutic compounds may be loaded into exosomes by electroporation or the use of a transfection reagent (e.g., cationic liposomes). An exosome-producing cell may be engineered to produce the exosome and load it with the therapeutic compound (i.e., an antisense oligonucleotide described herein). For example, exosomes may be loaded by transforming or transfecting an exosome-producing host cell with a genetic construct that expresses the therapeutic compound (i.e., an antisense oligonucleotide described herein), such that the therapeutic compound is taken up into the exosomes as the exosomes are produced by the host cell. An exosome-targeted protein in the exosome-producing cell may bind (i.e., non-covalently) to the therapeutic compound. Various targeting moieties may be introduced into exosomes, so that the exosomes can be targeted to a selected cell type, tissue, or organ. Targeting moieties may bind to cell-surface receptors or other cell-surface proteins or peptides that are specific to the targeted cell type, tissue, or organ. In some embodiments, exosomes have a targeting moiety expressed on their surface. In some embodiments, the targeting moiety expressed on the surface of exosomes is fused to an exosomal transmembrane protein. Techniques of introducing targeting moieties to exosomes are known in the art and described in, e.g., U.S. Patent Publication Nos. US 20130053426 and US 20140348904, and International Patent Publication No. WO 2015/002956, which are incorporated herein by reference.

Certain delivery systems are useful for preparing certain pharmaceutical compositions including those including hydrophobic compounds. Certain organic solvents such as dimethylsulfoxide may be used. A pharmaceutical composition of the present invention may include one or more tissue-specific delivery molecules designed to deliver the one or more pharmaceutical agents of the present invention to specific tissues or cell types. For example, pharmaceutical compositions may include liposomes coated with a tissue-specific antibody. A pharmaceutical composition of the present invention may include a sustained-release system. A non-limiting example of such a sustained-release system is a semi-permeable matrix of solid hydrophobic polymers. Sustained-release systems may, depending on their chemical nature, release pharmaceutical agents over a period of hours, days, weeks or months.

A pharmaceutical agent may be a sterile lyophilized antisense oligonucleotide that is reconstituted with a suitable diluent, e.g., sterile water for injection. The reconstituted product is administered as a subcutaneous injection or as an intravenous infusion after dilution into saline. The lyophilized drug product may consist of the antisense oligonucleotide which has been prepared in water for injection, adjusted to pH 7.0-9.0 with acid or base during preparation, and then lyophilized. The lyophilized antisense oligonucleotide may be 5-800 mg of the antisense oligonucleotide. It is understood that this encompasses 5, 10, 15, 20, 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized antisense oligonucleotide. The lyophilized drug product may be packaged in a 2 mL Type I, clear glass vial (ammonium sulfate-treated), stoppered with a bromobutyl rubber closure and sealed with an aluminum FLIP-OFF® overseal.

A pharmaceutical composition may be prepared for gene therapy. The pharmaceutical composition for gene therapy may be in an acceptable diluent or include a slow release matrix in which the gene delivery vehicle is embedded. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

A pharmaceutical composition of the present invention may be prepared for oral administration. A pharmaceutical composition may be formulated by combining one or more antisense oligonucleotides with one or more pharmaceutically acceptable carriers and excipients. Certain carriers and excipients may enable pharmaceutical compositions to be formulated as tablets, pills, dragees, capsules, liquids, gels, syrups, slurries, and suspensions, for oral ingestion by a subject. Pharmaceutical compositions for oral use may be obtained by mixing oligonucleotide and one or more solid excipients. Suitable carriers and excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. Such a mixture may be optionally ground, and auxiliaries may be optionally added. Pharmaceutical compositions may be formed to obtain tablets or dragee cores. Disintegrating agents (e.g., cross-linked polyvinyl pyrrolidone, agar, or alginic acid or a salt thereof, such as sodium alginate) may be added.

A pharmaceutical composition may be prepared for administration by injection (e.g., intravenous, subcutaneous, intramuscular, etc.). A pharmaceutical composition may include a carrier and is formulated in aqueous solution, such as water or physiologically compatible buffers such as PBS, Hank's solution, Ringer's solution, or physiological saline buffer. Examples of solvents suitable for use in pharmaceutical compositions for injection include, but are not limited to, lipophilic solvents and fatty oils, such as sesame oil, and synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

A pharmaceutical composition may be prepared for topical administration. Such pharmaceutical compositions may include bland moisturizing bases, such as ointments or creams. Exemplary suitable ointment bases include, but are not limited to, petrolatum, petrolatum plus volatile silicones, lanolin, and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP), and Lubriderm™, available from Pfizer (Morris Plains, N.J.).

Dosages and Administration

The pharmaceutical compositions used in this invention can be administered to a subject (e.g., a human patient) in a variety of ways. The compositions must be suitable for the subject receiving the treatment and the mode of administration. Furthermore, the severity of the disease to be treated affects the dosages and routes. The pharmaceutical compositions used in this invention may be administered orally, buccally, sublingually, parenterally, intravenously, subcutaneously, intramedullary, intranasally, as a suppository, using a flash formulation, topically, intradermally, subcutaneously, via pulmonary delivery, via intra-arterial injection, ophthalmically, optically, intrathecally, intracerebroventricularly (ICV), or via a mucosal route.

In general, the dosage of a pharmaceutical composition or the active agent in a pharmaceutical composition may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g, 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 µg, e.g., 200 ng, 300 ng, 400 ng, 500 ng, 600 ng, 700 ng, 800 ng, 900 ng, 1 µg, e.g., 1-10 µg, e.g., 1 µg, 2 µg, 3 µg, 4 µg, 5 µg, 6 µg, 7 µg, 8 µg, 9 µg, 10 µg, e.g., 10 µg-100 µg, e.g., 20 µg, 30 µg, 40 µg, 50 µg, 60 µg, 70 µg, 80 µg, 90 µg, 100 µg, e.g., 100 µg-1 mg, e.g., 200 µg, 300 µg, 400 µg, 500 µg, 600 µg, 700 µg, 800 µg, 900 µg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g).

The pharmaceutical composition may also be administered as in a unit dose form or as a dose per mass or weight of the patient from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the patient per unit day (e.g., 0.1-10 mg/kg/day).

The dosage regimen may be determined by the clinical indication being addressed, as well as by various patient variables (e.g., weight, age, sex) and clinical presentation (e.g., extent or severity of disease). Furthermore, it is understood that all dosages may be continuously given or divided into dosages given per a given time frame. The composition may be administered, for example, every hour, day, week, month, or year.

Assessment of ASOs

The activity of the antisense oligonucleotides of the present disclosure can be assessed (e.g., for increasing SCN2A pORF expression or reducing uORF expression) and confirmed using various techniques known in the art. For example, the ability of the antisense oligonucleotides to increase SCN2A pORF expression and/or whole cell current can be assessed in in vitro assays to confirm that the antisense oligonucleotides are suitable for use in treating a disease or condition associated with SCN2A. Mouse models can be used to not only assess the ability of the antisense oligonucleotides to increase SCN2A pORF expression or whole cell current, but to also ameliorate symptoms associated with SCN2A encephalopathies.

In one example, cells such as mammalian cells (e.g. CHO cells) that are transfected with SCN2A and express this gene are also transfected with an antisense oligonucleotide of the present disclosure. In another example, a human neuronal cell line (e.g. SH-SY5Y) that naturally expresses native wild type SCN2A is used. The levels of SCN2A pORF or uORF mRNA can be assessed using qRT-PCR or Northern blot as is well known in the art. The level of expression of protein from SCN2A pORF or uORF can be assessed by Western blot on total cell lysates or fractions as described in Rizzo et al. (Mol Cell Neurosci. 72:54-63, 2016). Function of the SCN2A-encoded channels can also be assessed using electrophysiology or ion flux assay. In another example, the presence or amount of protein can be detected and/or quantified using mass spectrometry. Mass spectrometry may be used to characterize the SCN2A protein that is expressed. For example, the relative abundances of each uORF protein and the pORF protein can be measured before and after treatment with an ASO to assess the change in expression.

In a particular example, the activity of the antisense oligonucleotides of the present disclosure is assessed and confirmed using stem cell modelling (for review, see e.g. Tidball and Parent Stem Cells 34:27-33, 2016; Parent and Anderson Nature Neuroscience 18:360-366, 2015). For example, human induced pluripotent stem cells (iPSCs) can be produced from somatic cells (e.g. dermal fibroblasts or blood-derived hematopoietic cells) derived from a patient presenting with an associated disease or condition (e.g. epilepsy). The iPSCs containing the SCN2A, and optionally the isogenic control, can then be differentiated into neurons, including excitatory neurons, using known techniques (see e.g. Kim et al. Front Cell Neurosci 8:109, 2014; Zhang et al. 2013, Chambers et al. Nat Biotechnol 27, 275-280, 2009). The effect of the antisense oligonucleotides of the present invention on SCN2A pORF and uORF expression (as assessed by SCN2A mRNA or protein levels) and/or activity (as assessed by ion flux assay and/or electrophysiology, e.g. using the whole cell patch clamp technique, the single electrode voltage clamp technique or the two-electrode voltage clamp (TEVC) technique) can then be assessed following exposure of the iPSCs to the antisense oligonucleotides of the present invention.

The levels of SCN2A expression (mRNA or protein) or whole cell current observed when cells expressing SCN2A are exposed to an antisense oligonucleotide of the present disclosure are compared to the respective levels observed when cells expressing SCN2A are exposed with a negative control antisense oligonucleotide, so as to determine the level of increase resulting from the antisense oligonucleotide of the present disclosure. Typically, expression levels of SCN2A or whole cell current levels are increased by at least or about 20%, 25%, 30%, 35%, 40%, 45%, 50%, 55%, 60%, 65%, 70%, 75%, 80%, 85%, 90% or more. Accordingly, the antisense oligonucleotides of the present disclosure can be used for treating a disease or condition associated with SCN2A.

Mouse models can also be used to assess and confirm the activity of the antisense oligonucleotides of the present disclosure. For example, knock-in or transgenic mouse models can be generated using SCN2A genes, e.g., containing one or more uORFs, e.g., similarly to as described in Kearney et al. Neuroscience 102, 307-317, 2001; Ogiwara et al. J Neurosci 27:5903-5914, 2007; Yu et al. Nat Neurosci 9:1142-1149, 2006).

For example, the levels of SCN2A mRNA and/or protein can be assessed following administration of an antisense oligonucleotide of the present disclosure or a negative control antisense oligonucleotide to the mice. In a particular example, SCN2A mRNA and/or protein levels in the brain, and in particular the neurons, are assessed. The levels of SCN2A expression following administration of an antisense oligonucleotide of the present disclosure are compared to the respective levels observed when a negative control antisense oligonucleotide is administered, so as to determine the level of increase resulting from the antisense oligonucleotide of the present disclosure. Typically, expression levels of SCN2A in the mice (e.g. in the brains of the mice) are increased by at least or about 20%, 25%, 30%, 35%, 40%, 45%, 50%, 55%, 60%, 65%, 70%, 75%, 80%, 85%, 90% or more.

In another example, the functional effect of administration of an antisense oligonucleotide of the present disclosure is assessed. For example, the number, severity and/or type of seizures can be assessed visually and/or by EEG. Neuronal excitability can also be assessed, such as by excising brain slices from mice administered an antisense oligonucleotide of the present disclosure or a negative control antisense oligonucleotide and assessing whole cell current (e.g. using the whole cell patch clamp technique). Similar neuronal excitability analyses can be performed using neurons isolated from the mice and then cultured. Additionally, mouse behavior, including gait characteristics, can be assessed to determine the functional effect of administration of an antisense oligonucleotide of the present disclosure.

EXAMPLES

Example 1. Design of an ASO Targeting a uORF

Antisense oligonucleotides were designed to target an AUG start codon upstream of the pORF of mRNA transcript 1 (SEQ ID NO: 1). The sequence of the upstream region of the mRNA is shown below.

```
>mRNA transcript 1
                                         (SEQ ID NO: 1)
5'CAUCCAUAGAUCUACCAAAAGAUUCCCAGACUCUGGCCCAAUUUUCU

UGUUUCCUAGACCAUUAUUUCCCAGACAGUGAUUGGAGGAAUACUACUG

UUCUGCUGGACUAAUGAAGUGCCACUCCACAUCCACCAGAAUGGCUACA

ACUUAAAAAGGCUUAUCAUACUGUUUGUGAGAAUCUAGAGCUACAGAAC

CUGUCAGAGACUUCAGCACUUUCUUAUGCAAGGAGCUAAACAGUGAUU

AAAGGAGCAGGAUGAAAAGAUG
```

The pORF AUG and the target AUG are bold and underlined. The target AUG is also italicized. The ORFs are consecutively numbered from the pORF AUG at the 3' end to the uORF at the 5' end. Thus, ORF 1 is the pORF AUG, while ORFs 2-5 go from the 3' end to the 5' end. In this example, the target ORF is ORF 3.

We designed 16mer ASOs around mRNA transcript 1, ORF 3 (2 AUG codons upstream of the pORF AUG). All ASOs are complementary to at least 2 nucleotides within the target AUG start codon. The sequences of each ASO and its corresponding target sequence is shown in Table 20 below.

TABLE 20

16mer ASO constructs targeting mRNA transcript 1 (SEQ ID NO: 1), ORF3

| Name | ASO Sequence | Target Sequence |
|---|---|---|
| mRNA transcript 1, ORF 3, construct 1 | 5'ATAAGAAAGTGCTGAA (SEQ ID NO: 19) | 5'UUCAGCACUUUCUUAU (SEQ ID NO: 276) |
| mRNA transcript 1, ORF 3, construct 2 | 5'CATAAGAAAGTGCTGA (SEQ ID NO: 20) | 5'UCAGCACUUUCUUAUG (SEQ ID NO: 277) |
| mRNA transcript 1, ORF 3, construct 3 | 5'GCATAAGAAAGTGCTG (SEQ ID NO: 21) | 5'CAGCACUUUCUUAUGC (SEQ ID NO: 278) |
| mRNA transcript 1, ORF 3, construct 4 | 5'TGCATAAGAAAGTGCT (SEQ ID NO: 22) | 5'AGCACUUUCUUAUGCA (SEQ ID NO: 279) |
| mRNA transcript 1, ORF 3, construct 5 | 5'TTGCATAAGAAAGTGC (SEQ ID NO: 23) | 5'GCACUUUCUUAUGCAA (SEQ ID NO: 280) |
| mRNA transcript 1, ORF 3, construct 6 | 5'CTTGCATAAGAAACTG (SEQ ID NO: 24) | 5'CACUUUCUUAUGCAAG (SEQ ID NO: 281) |
| mRNA transcript 1, ORF 3, construct 7 | 5'CCTTGCATAAGAAAGT (SEQ ID NO: 25) | 5'ACUUUCUUAUGCAAGG (SEQ ID NO: 282) |
| mRNA transcript 1, ORF 3, construct 8 | 5'TCCTTGCATAAGAAAG (SEQ ID NO: 26) | 5'CUUUCUUAUGCAAGGA (SEQ ID NO: 283) |
| mRNA transcript 1, ORF 3, construct 9 | 5'CTCCTTGCATAAGAAA (SEQ ID NO: 27) | 5'UUUCUUAUGCAAGGAG (SEQ ID NO: 284) |
| mRNA transcript 1, ORF 3, construct 10 | 5'GCTCCTTGCATAAGAA (SEQ ID NO: 28) | 5'UUCUUAUGCAAGGAGC (SEQ ID NO: 285) |
| mRNA transcript 1, ORF 3, construct 11 | 5'AGCTCCTTGCATAAGA (SEQ ID NO: 29) | 5'UCUUAUGCAAGGAGCU (SEQ ID NO: 286) |
| mRNA transcript 1, ORF 3, construct 12 | 5'TAGCTCCTTGCATAAG (SEQ ID NO: 30) | 5'CUUAUGCAAGGAGCUA (SEQ ID NO: 287) |
| mRNA transcript 1, ORF 3, construct 13 | 5'TTAGCTCCTTGCATAA (SEQ ID NO: 31) | 5'UUAUGCAAGGAGCUAA (SEQ ID NO: 288) |
| mRNA transcript 1, ORF 3, construct 14 | 5'TTTAGCTCCTTGCATA (SEQ ID NO: 32) | 5'UAUGCAAGGAGCUAAA (SEQ ID NO: 289) |
| mRNA transcript 1, ORF 3, construct 15 | 5'GTTTAGCTCCTTGCAT (SEQ ID NO: 33) | 5'AUGCAAGGAGCUAAAC (SEQ ID NO: 290) |
| mRNA transcript 1, ORF 3, construct 16 | 5'TGTTTAGCTCCTTGCA (SEQ ID NO: 34) | 5'UGCAAGGAGCUAAACA (SEQ ID NO: 291) |

Example 2. Design of an ASO Targeting a uORF of any of SEQ ID NOs: 1-8

Antisense oligonucleotides were designed to target an AUG start codon upstream of the pORF of any of mRNA transcripts 1-8 (SEQ ID NOs: 1-8). The sequence of the upstream region of the mRNA that is shared by all mRNA transcripts is shown below.

>upstream region of mRNA transcripts 1-8
(SEQ ID NO: 11)
5'CACUUUCUUAUGCAAGGAGCUAAACAGUGAUUAAAGGAGCAGG*AUG*

AAAAG*AUG*

The pORF AUG and the target AUG are bold and underlined. The target AUG is also italicized. The ORFs are consecutively numbered from the pORF AUG at the 3' end to the uORF at the 5' end. Thus, ORF 1 is the pORF AUG, while ORFs 2-5 go from the 3' end to the 5' end. In this example, the target ORF is ORF 2.

We designed 16mer ASOs around the upstream region of mRNA transcripts 1-8, ORF 2 (AUG codon immediately upstream of the pORF AUG). All ASOs are complementary to at least 2 nucleotides within the target AUG start codon. The sequences of each ASO and its corresponding target sequence is shown in Table 21 below.

TABLE 21

16 mer ASO constructs targeting mRNA transcripts 1-8 (SEQ ID NO: 11), ORF 2

| Name | ASO Sequence | Target Sequence |
| --- | --- | --- |
| mRNA transcripts 1-8, ORF 2, construct 1 | 5'ATCCTGCTCCTTTAAT (SEQ ID NO: 12) | 5'AUUAAAGGAGCAGGAU (SEQ ID NO: 269) |
| mRNA transcripts 1-8, ORF 2, construct 2 | 5'CATCCTGCTCCTTTAA (SEQ ID NO: 13) | 5'UUAAAGGAGCAGGAUG (SEQ ID NO: 270) |
| mRNA transcripts 1-8, ORF 2, construct 3 | 5'TCATCCTGCTCCTTTA (SEQ ID NO: 14) | 5'UAAAGGAGCAGGAUGA (SEQ ID NO: 271) |
| mRNA transcripts 1-8, ORF 2, construct 4 | 5'TTCATCCTGCTCCTTT (SEQ ID NO: 15) | 5'AAAGGAGCAGGAUGAA (SEQ ID NO: 272) |
| mRNA transcripts 1-8, ORF 2, construct 5 | 5'TTTCATCCTGCTCCTT (SEQ ID NO: 16) | 5'AAGGAGCAGGAUGAAA (SEQ ID NO: 273) |
| mRNA transcripts 1-8, ORF 2, construct 6 | 5'TTTTCATCCTGCTCCT (SEQ ID NO: 17) | 5'AGGAGCAGGAUGAAAA (SEQ ID NO: 274) |
| mRNA transcripts 1-8, ORF 2, construct 7 | 5'CTTTTCATCCTGCTCC (SEQ ID NO: 18) | 5'GGAGCAGGAUGAAAAG (SEQ ID NO: 275) |

Example 3. In Vitro Increase in Translation of SCN2A with SCN2A ASO

Human SCN2A wild-type or mutated SCN2A cDNA (including regions of the 5'UTR containing the uORF sequences of interest as well as some flanking 5' sequence) is cloned into a vector, through methods one having skill in the art would commonly know. All constructs are verified with sequencing. Human embryonic kidney cells (HEK293) are maintained and incubated in proper cell culture. HEK293 cells are transfected with one type of the prepared constructs at a concentration range of about 0.1 ng/ml to 100 ng/ml plasmid. Transfection is done with methods known to a person having skill in the art. Transfected cells are incubated for 12-36 hours at 37° C. post transfection and then plated for experiments.

Transfected HEK293 cells or human stem cells induced to differentiate into neurons are treated with ASO designed and prepared as illustrated in Example 1 above. RNA and protein levels are measured in separate concentration response and time course experiments. RNA levels can be measured through northern blotting, RT-PCR, and/or quantitative PCR analysis. Protein levels are measured through western blotting analysis.

Example 4. Treatment of SCN2A Encephalopathy by Administration of an ASO

A human patient with an SCN2A encephalopathy is selected for ASO treatment. A 16mer antisense oligonucleotide targeting mRNA uORF 3 is synthesized with phosphorothioate linkages throughout and 2MOE modifications on all sugar moieties. The ASO is dissolved in a suitable excipient compatible with administration to a human. A solution containing the dissolved ASO is injected into the brain of the patient such that the ASO solution interacts with targeted neurons in the brain. The ASO transfects the neurons and alters the translation of SCN2A in the target cells, leading to an increase in SCN2A protein. A quantitative assay is performed to measure the increase in SCN2A protein. The patient undergoes extensive regular testing to measure a reduction of symptoms associated with the SCN2A encephalopathy following administration of the ASO treatment.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of treating an encephalopathy or autism in a subject in need thereof, the method comprising administering to the subject a compound comprising a modified oligonucleotide that is 10-80 nucleosides in length and having a nucleobase sequence comprising a portion of at least 10 contiguous nucleobases complementary to an equal length portion of a target region of an mRNA transcript upstream of a primary open reading frame (pORF) of a human SCN2A gene, wherein the compound (i) does not activate RNaseH or RISC pathways, and (ii) increases expression of the pORF of the human SCN2A gene, in an amount and for a duration sufficient to treat the encephalopathy or autism.

2. The method of claim 1, wherein the encephalopathy is an SCN2A-related encephalopathy.

3. A method of increasing expression of SCN2A in cells of a subject, the method comprising contacting the cells with a compound comprising a modified oligonucleotide that is 10-80 nucleosides in length and having a nucleobase sequence comprising a portion of at least 10 contiguous nucleobases complementary to an equal length portion of a target region of an mRNA transcript upstream of a primary open reading frame (pORF) of a human SCN2A gene, wherein the compound (i) does not activate RNaseH or RISC pathways, and (ii) increases expression of the pORF of the human SCN2A gene, in an amount and for a duration sufficient to increase expression of SCN2A.

4. The method of claim 1, wherein the subject has a mutation in the SCN2A gene that reduces SCN2A activity.

5. The method of claim 3, wherein the subject has a mutation in the SCN2A gene that reduces SCN2A activity and/or transcription.

6. The method of claim 1, wherein the oligonucleotide has the sequence of any one of SEQ ID NOs: 12-268.

7. The method of claim 3, wherein the oligonucleotide has the sequence of any one of SEQ ID NOs: 12-268.

* * * * *

SEQUENCE LISTING

<160> NUMBER OF SEQ ID NOS: 525

<210> SEQ ID NO 1
<211> LENGTH: 264
<212> TYPE: RNA
<213> ORGANISM: Homo sapiens

<400> SEQUENCE: 1
cauccauaga ucuaccaaaa gauucccaga cucuggccca auuuucuugu uuccuagacc    60

| | |
|---|---:|
| auuauuuccc agacagugau uggaggaaua cuacuguucu gcuggacuaa ugaagugcca | 120 |
| cuccacaucc accagaaugg cuacaacuua aaaaggcuua ucauacuguu ugugagaauc | 180 |
| uagagcuaca gaagcuguca gagacuucag cacuuucuua ugcaaggagc uaaacaguga | 240 |
| uuaaaggagc aggaugaaaa gaug | 264 |

<210> SEQ ID NO 2
<211> LENGTH: 208
<212> TYPE: RNA
<213> ORGANISM: Homo sapiens

<400> SEQUENCE: 2

| | |
|---|---:|
| cuaccagaag uuccuuuuuu cuccauuucu ucuggcaguu acagaauccu cuuggggcuu | 60 |
| ucuuagagcc aaucccucu aaggugaaug cauuuucuug cauucaccug ucaugaaaug | 120 |
| gcagguggaaa gacuugaaga aggcacaggc guugcacuuu cuuaugcaag gagcuaaaca | 180 |
| gugauuaaag gagcaggaug aaaagaug | 208 |

<210> SEQ ID NO 3
<211> LENGTH: 309
<212> TYPE: RNA
<213> ORGANISM: Homo sapiens

<400> SEQUENCE: 3

| | |
|---|---:|
| auuuuucuaa uuuagcaugc uguuuucuaa cagacauugg guaccaucga augacuguca | 60 |
| gaacagaaag cuaaggcaaa ggagggagga ugcuguggc auccuuucuu guuuuuucu | 120 |
| ucuuuaauga ggauagagca caugugagau uuuacuuucu acuccaguaa aaauucugaa | 180 |
| gaauugcauu ggagacuguu auauucaaca caucgugga uucuguguua ugauuuacau | 240 |
| uuucuuuau uucagcacuu ucuuaugcaa ggagcuaaac agugauuaaa ggagcaggau | 300 |
| gaaaagaug | 309 |

<210> SEQ ID NO 4
<211> LENGTH: 54
<212> TYPE: RNA
<213> ORGANISM: Homo sapiens

<400> SEQUENCE: 4

| | |
|---|---:|
| cacuuucuua ugcaaggagc uaaacaguga uuaaaggagc aggaugaaaa gaug | 54 |

<210> SEQ ID NO 5
<211> LENGTH: 293
<212> TYPE: RNA
<213> ORGANISM: Homo sapiens

<400> SEQUENCE: 5

| | |
|---|---:|
| augcuguuuu cuaacagaca uuggguacca ucgaaugacu gucagaacag aaagcuaagg | 60 |
| caaaggaggg aggaugcugu ggucauccuu ucuguuuuu uucuucuuua augaggauag | 120 |
| agcacaugug agauuuuacu uucuacucca guaaaaauuc ugaagaauug cauuggagac | 180 |
| uguuauauuc aacacauacg uggauucugu guuaugauuu acauuuuucu uuauuucagc | 240 |
| acuuucuuau gcaaggagcu aaacagugau uaaaggagca ggaugaaaag aug | 293 |

<210> SEQ ID NO 6
<211> LENGTH: 359
<212> TYPE: RNA
<213> ORGANISM: Homo sapiens

<400> SEQUENCE: 6

```
ggcugcuuca gacauauguc ugugugguacg cugugaaggu guuucucuuc acaguucccc    60
gcccucuagu gguaguuaca auaaugccau uuuguaguccc cugugcagga aaugccucuu   120
cuuacuucag uuaccagaau ccuuuuacag gaaguuaggu guggucuuug aaggagaauu   180
aaaaaaaaaa aaaaaaaaaa aaaaaaaaga uuuuuuuuuu uuuaaagcau gauggaauuu   240
uagcugcagu cuucuuggug ccagcuuauc aaucccaaac ucuggguguaa aaagauucua   300 cagggcacuu ucuuaugcaa ggagcuaaac agugauuaaa ggagcaggau gaaaagaug    359

<210> SEQ ID NO 7
<211> LENGTH: 161
<212> TYPE: RNA
<213> ORGANISM: Homo sapiens

<400> SEQUENCE: 7
aaaaaaaaaa gauuuuuuuu uuuuuaaagc augauggaau uuagcugca gucuucuugg     60 ugccagcuua ucaaucccaa acucggguga uaaaagauuc uacagggcac uuucuuaugc   120
aaggagcuaa acagugauua aaggagcagg augaaaagau g                      161

<210> SEQ ID NO 8
<211> LENGTH: 286
<212> TYPE: RNA
<213> ORGANISM: Homo sapiens

<400> SEQUENCE: 8
uuucuaacag acauugggua ccaucgaaug acugucagaa cagaaagcua aggcaaagga    60
gggaggaugc uguggucauc cuuucuuguu uuuucuucu uuaaugagga uagagcacau   120
gugagauuuu acuuucuacu ccaguaaaaa uucugaagaa uugcauugga gacuguuaua   180
uucaacacau acgugggauuc uguguuauga uuuacauuuu ucuuuauuuc agcacuuucu   240
uaugcaagga gcuaaacagu gauuaaagga gcaggaugaa aagaug                 286

<210> SEQ ID NO 9
<211> LENGTH: 147
<212> TYPE: RNA
<213> ORGANISM: Homo sapiens

<400> SEQUENCE: 9
aaauacuugc aagggcuuu uguuagaag auuucacauu uuuacgggau ccauggaauu     60
gguuggauuu cacagucauu acuuugcgc cugaagacca uguggggggc ccugauccag   120
ucagugaaga agcuuucuga ugucaug                                     147

<210> SEQ ID NO 10
<211> LENGTH: 1593
<212> TYPE: RNA
<213> ORGANISM: Homo sapiens

<400> SEQUENCE: 10
cgucacaguu acuggugcu uugguaauga ugaaaaaaca cuucauaaau uucauaaaa      60 uacuuccuga cuugauauug uaucauuauu acacauuuua cuaaauaaca guaaaauccg   120
ugcauaacuc auggauucua uuacuuccca cagauuuuuu uuuuauau uuagccucca    180 gaaagcugcu gcaaaaugua gguauauuuu gaacaccacu uucauacauu aaauucuaaa   240
cauugaaacu ugugugcaug acguugaaaa gagguguaaug auaaaugcuu uacuuauga   300 ugaugcuaag ccauuuggau uauauuaacu gcuugagaca caaguuauaa aauccuauga   360
```

| | |
|---|---|
| cuuaaccaga aauauaaauu aaaaauguga auuaggguuu gauauuaacu uccuugaagc | 420 |
| aaaguguuua aaauuuugua guccuacuuu ugccuuucuc ugaccagauu cuuacaauau | 480 |
| aucagcuuuc ucuuuaguug cagauuuuau cugaauaguu aacauaaugu guagcagucu | 540 |
| ggaucucaga augccaaaau aaagacuuug gggacagcuu aaucugugau caauuucugg | 600 |
| cucugccaua uguuaaaugu guuaauuugu gacuugaauu ucagucucc ucaucaguaa | 660 |
| aauguggaug augauguuua ggcauaaggu uguugaaugg auuaaauaag ccuucuuaga | 720 |
| uaaaacacug auguauuugg caugcagaag acaguaaua aauauuauca auauuaguug | 780 |
| uuuuguuguu guuauuuuug uuaauucaca uguuuugcc uuccauacu guaagugaau | 840 |
| ucaaacaacu gucaacuuca acuacuugga aaauauuuc auguaaaaug uauucuaucc | 900 |
| cccuuccuug cccuccuauu cccuccucuc ccuaucucuu acaaaccuu ucccuugua | 960 |
| ccccuucccca gguaugugug ugagugugag ugugucuaga ugugucaagg gagaagagaa | 1020 |
| aaggagaaug aaagcaaaag agagcaagca uacacguccc uuucuauug auaauuagau | 1080 |
| uuucucuuga gauuggauag auuccuggaa uaauucuuuu ccugucugua ugcaaagauc | 1140 |
| ccauaauauu auuaauacca auacgaaaag ccugaaaauc acagccagaa aaaauucaca | 1200 |
| guguagacga cuguguacau cacagacaag ucaguauuac aaaaacccaau uuucauagug | 1260 |
| uccuauuuca guaccuaau gcaauucacu gauuucaauu gaauauuaaa cucuaguacg | 1320 |
| uucuuccca accucgccug cguuagcuug cacucccucu uccccccagc ugccaguagc | 1380 |
| uugcuccucc cuguccucc agguaaaucu uuugaagauu gucuggccuu ccgcuccuug | 1440 |
| ccauagcaaa accacugaga ggaagcugcc agugguucug cuaccgaugu cagcagcaug | 1500 |
| ucugcucccu aaagcaggaa guagagaagg agacaggaac uugaagaauc cagacagaaa | 1560 |
| ugccccaccau gcugguauaa auuugcuaau aug | 1593 |

```
<210> SEQ ID NO 11
<211> LENGTH: 54
<212> TYPE: RNA
<213> ORGANISM: Homo sapiens

<400> SEQUENCE: 11
```

| | |
|---|---|
| cacuuucuua ugcaaggagc uaaacaguga uuaaaggagc aggaugaaaa gaug | 54 |

```
<210> SEQ ID NO 12
<211> LENGTH: 16
<212> TYPE: DNA
<213> ORGANISM: Homo sapiens

<400> SEQUENCE: 12
```

| | |
|---|---|
| atcctgctcc tttaat | 16 |

```
<210> SEQ ID NO 13
<211> LENGTH: 16
<212> TYPE: DNA
<213> ORGANISM: Homo sapiens

<400> SEQUENCE: 13
```

| | |
|---|---|
| catcctgctc ctttaa | 16 |

```
<210> SEQ ID NO 14
<211> LENGTH: 16
<212> TYPE: DNA
<213> ORGANISM: Homo sapiens

<400> SEQUENCE: 14
```

```
tcatcctgct ccttta                                              16

<210> SEQ ID NO 15
<211> LENGTH: 16
<212> TYPE: DNA
<213> ORGANISM: Homo sapiens

<400> SEQUENCE: 15
ttcatcctgc tccttt                                              16

<210> SEQ ID NO 16
<211> LENGTH: 16
<212> TYPE: DNA
<213> ORGANISM: Homo sapiens

<400> SEQUENCE: 16
tttcatcctg ctcctt                                              16

<210> SEQ ID NO 17
<211> LENGTH: 16
<212> TYPE: DNA
<213> ORGANISM: Homo sapiens

<400> SEQUENCE: 17
ttttcatcct gctcct                                              16

<210> SEQ ID NO 18
<211> LENGTH: 16
<212> TYPE: DNA
<213> ORGANISM: Homo sapiens

<400> SEQUENCE: 18
cttttcatcc tgctcc                                              16

<210> SEQ ID NO 19
<211> LENGTH: 16
<212> TYPE: DNA
<213> ORGANISM: Homo sapiens

<400> SEQUENCE: 19
ataagaaagt gctgaa                                              16

<210> SEQ ID NO 20
<211> LENGTH: 16
<212> TYPE: DNA
<213> ORGANISM: Homo sapiens

<400> SEQUENCE: 20
cataagaaag tgctga                                              16

<210> SEQ ID NO 21
<211> LENGTH: 16
<212> TYPE: DNA
<213> ORGANISM: Homo sapiens

<400> SEQUENCE: 21
gcataagaaa gtgctg                                              16

<210> SEQ ID NO 22
<211> LENGTH: 16
<212> TYPE: DNA
<213> ORGANISM: Homo sapiens
```

```
<400> SEQUENCE: 22
tgcataagaa agtgct                                                       16

<210> SEQ ID NO 23
<211> LENGTH: 16
<212> TYPE: DNA
<213> ORGANISM: Homo sapiens

<400> SEQUENCE: 23
ttgcataaga aagtgc                                                       16

<210> SEQ ID NO 24
<211> LENGTH: 16
<212> TYPE: DNA
<213> ORGANISM: Homo sapiens

<400> SEQUENCE: 24
cttgcataag aaagtg                                                       16

<210> SEQ ID NO 25
<211> LENGTH: 16
<212> TYPE: DNA
<213> ORGANISM: Homo sapiens

<400> SEQUENCE: 25
ccttgcataa gaaagt                                                       16

<210> SEQ ID NO 26
<211> LENGTH: 16
<212> TYPE: DNA
<213> ORGANISM: Homo sapiens

<400> SEQUENCE: 26
tccttgcata agaaag                                                       16

<210> SEQ ID NO 27
<211> LENGTH: 16
<212> TYPE: DNA
<213> ORGANISM: Homo sapiens

<400> SEQUENCE: 27
ctccttgcat aagaaa                                                       16

<210> SEQ ID NO 28
<211> LENGTH: 16
<212> TYPE: DNA
<213> ORGANISM: Homo sapiens

<400> SEQUENCE: 28
gctccttgca taagaa                                                       16

<210> SEQ ID NO 29
<211> LENGTH: 16
<212> TYPE: DNA
<213> ORGANISM: Homo sapiens

<400> SEQUENCE: 29
agctccttgc ataaga                                                       16

<210> SEQ ID NO 30
<211> LENGTH: 16
<212> TYPE: DNA
```

```
<400> SEQUENCE: 30
tagctccttg cataag                                               16

<210> SEQ ID NO 31
<211> LENGTH: 16
<212> TYPE: DNA
<213> ORGANISM: Homo sapiens

<400> SEQUENCE: 31
ttagctcctt gcataa                                               16

<210> SEQ ID NO 32
<211> LENGTH: 16
<212> TYPE: DNA
<213> ORGANISM: Homo sapiens

<400> SEQUENCE: 32
tttagctcct tgcata                                               16

<210> SEQ ID NO 33
<211> LENGTH: 16
<212> TYPE: DNA
<213> ORGANISM: Homo sapiens

<400> SEQUENCE: 33
gtttagctcc ttgcat                                               16

<210> SEQ ID NO 34
<211> LENGTH: 16
<212> TYPE: DNA
<213> ORGANISM: Homo sapiens

<400> SEQUENCE: 34
tgtttagctc cttgca                                               16

<210> SEQ ID NO 35
<211> LENGTH: 16
<212> TYPE: DNA
<213> ORGANISM: Homo sapiens

<400> SEQUENCE: 35
ataacacaga atccac                                               16

<210> SEQ ID NO 36
<211> LENGTH: 16
<212> TYPE: DNA
<213> ORGANISM: Homo sapiens

<400> SEQUENCE: 36
cataacacag aatcca                                               16

<210> SEQ ID NO 37
<211> LENGTH: 16
<212> TYPE: DNA
<213> ORGANISM: Homo sapiens

<400> SEQUENCE: 37
tcataacaca gaatcc                                               16

<210> SEQ ID NO 38
<211> LENGTH: 16
<212> TYPE: DNA
```

```
<213> ORGANISM: Homo sapiens

<400> SEQUENCE: 38
atcataacac agaatc                                                       16

<210> SEQ ID NO 39
<211> LENGTH: 16
<212> TYPE: DNA
<213> ORGANISM: Homo sapiens

<400> SEQUENCE: 39
aatcataaca cagaat                                                       16

<210> SEQ ID NO 40
<211> LENGTH: 16
<212> TYPE: DNA
<213> ORGANISM: Homo sapiens

<400> SEQUENCE: 40
aaatcataac acagaa                                                       16

<210> SEQ ID NO 41
<211> LENGTH: 16
<212> TYPE: DNA
<213> ORGANISM: Homo sapiens

<400> SEQUENCE: 41
taaatcataa cacaga                                                       16

<210> SEQ ID NO 42
<211> LENGTH: 16
<212> TYPE: DNA
<213> ORGANISM: Homo sapiens

<400> SEQUENCE: 42
gtaaatcata acacag                                                       16

<210> SEQ ID NO 43
<211> LENGTH: 16
<212> TYPE: DNA
<213> ORGANISM: Homo sapiens

<400> SEQUENCE: 43
tgtaaatcat aacaca                                                       16

<210> SEQ ID NO 44
<211> LENGTH: 16
<212> TYPE: DNA
<213> ORGANISM: Homo sapiens

<400> SEQUENCE: 44
atgtaaatca taacac                                                       16

<210> SEQ ID NO 45
<211> LENGTH: 16
<212> TYPE: DNA
<213> ORGANISM: Homo sapiens

<400> SEQUENCE: 45
aatgtaaatc ataaca                                                       16

<210> SEQ ID NO 46
<211> LENGTH: 16
```

```
<212> TYPE: DNA
<213> ORGANISM: Homo sapiens

<400> SEQUENCE: 46
aaatgtaaat cataac                                                      16

<210> SEQ ID NO 47
<211> LENGTH: 16
<212> TYPE: DNA
<213> ORGANISM: Homo sapiens

<400> SEQUENCE: 47
aaaatgtaaa tcataa                                                      16

<210> SEQ ID NO 48
<211> LENGTH: 16
<212> TYPE: DNA
<213> ORGANISM: Homo sapiens

<400> SEQUENCE: 48
aaaaatgtaa atcata                                                      16

<210> SEQ ID NO 49
<211> LENGTH: 16
<212> TYPE: DNA
<213> ORGANISM: Homo sapiens

<400> SEQUENCE: 49
gaaaaatgta aatcat                                                      16

<210> SEQ ID NO 50
<211> LENGTH: 16
<212> TYPE: DNA
<213> ORGANISM: Homo sapiens

<400> SEQUENCE: 50
agaaaaatgt aaatca                                                      16

<210> SEQ ID NO 51
<211> LENGTH: 16
<212> TYPE: DNA
<213> ORGANISM: Homo sapiens

<400> SEQUENCE: 51
atttcatgac aggtga                                                      16

<210> SEQ ID NO 52
<211> LENGTH: 16
<212> TYPE: DNA
<213> ORGANISM: Homo sapiens

<400> SEQUENCE: 52
catttcatga caggtg                                                      16

<210> SEQ ID NO 53
<211> LENGTH: 16
<212> TYPE: DNA
<213> ORGANISM: Homo sapiens

<400> SEQUENCE: 53
ccatttcatg acaggt                                                      16

<210> SEQ ID NO 54
```

```
<211> LENGTH: 16
<212> TYPE: RNA
<213> ORGANISM: Homo sapiens

<400> SEQUENCE: 54
ccugucauga aauggc                                                         16

<210> SEQ ID NO 55
<211> LENGTH: 16
<212> TYPE: DNA
<213> ORGANISM: Homo sapiens

<400> SEQUENCE: 55
tgccatttca tgacag                                                         16

<210> SEQ ID NO 56
<211> LENGTH: 16
<212> TYPE: DNA
<213> ORGANISM: Homo sapiens

<400> SEQUENCE: 56
ctgccatttc atgaca                                                         16

<210> SEQ ID NO 57
<211> LENGTH: 16
<212> TYPE: DNA
<213> ORGANISM: Homo sapiens

<400> SEQUENCE: 57
actgccattt catgac                                                         16

<210> SEQ ID NO 58
<211> LENGTH: 16
<212> TYPE: DNA
<213> ORGANISM: Homo sapiens

<400> SEQUENCE: 58
cactgccatt tcatga                                                         16

<210> SEQ ID NO 59
<211> LENGTH: 16
<212> TYPE: DNA
<213> ORGANISM: Homo sapiens

<400> SEQUENCE: 59
ccactgccat ttcatg                                                         16

<210> SEQ ID NO 60
<211> LENGTH: 16
<212> TYPE: DNA
<213> ORGANISM: Homo sapiens

<400> SEQUENCE: 60
tccactgcca tttcat                                                         16

<210> SEQ ID NO 61
<211> LENGTH: 16
<212> TYPE: DNA
<213> ORGANISM: Homo sapiens

<400> SEQUENCE: 61
ttccactgcc atttca                                                         16
```

-continued

```
<210> SEQ ID NO 62
<211> LENGTH: 16
<212> TYPE: DNA
<213> ORGANISM: Homo sapiens

<400> SEQUENCE: 62
tttccactgc catttc                                               16

<210> SEQ ID NO 63
<211> LENGTH: 16
<212> TYPE: DNA
<213> ORGANISM: Homo sapiens

<400> SEQUENCE: 63
ctttccactg ccattt                                               16

<210> SEQ ID NO 64
<211> LENGTH: 16
<212> TYPE: DNA
<213> ORGANISM: Homo sapiens

<400> SEQUENCE: 64
tctttccact gccatt                                               16

<210> SEQ ID NO 65
<211> LENGTH: 16
<212> TYPE: DNA
<213> ORGANISM: Homo sapiens

<400> SEQUENCE: 65
gtctttccac tgccat                                               16

<210> SEQ ID NO 66
<211> LENGTH: 16
<212> TYPE: DNA
<213> ORGANISM: Homo sapiens

<400> SEQUENCE: 66
agtctttcca ctgcca                                               16

<210> SEQ ID NO 67
<211> LENGTH: 16
<212> TYPE: DNA
<213> ORGANISM: Homo sapiens

<400> SEQUENCE: 67
atgacaggtg aatgca                                               16

<210> SEQ ID NO 68
<211> LENGTH: 16
<212> TYPE: DNA
<213> ORGANISM: Homo sapiens

<400> SEQUENCE: 68
catgacaggt gaatgc                                               16

<210> SEQ ID NO 69
<211> LENGTH: 16
<212> TYPE: DNA
<213> ORGANISM: Homo sapiens

<400> SEQUENCE: 69
tcatgacagg tgaatg                                               16
```

```
<210> SEQ ID NO 70
<211> LENGTH: 16
<212> TYPE: RNA
<213> ORGANISM: Homo sapiens

<400> SEQUENCE: 70
auucaccugu caugaa                                                    16

<210> SEQ ID NO 71
<211> LENGTH: 16
<212> TYPE: DNA
<213> ORGANISM: Homo sapiens

<400> SEQUENCE: 71
tttcatgaca ggtgaa                                                    16

<210> SEQ ID NO 72
<211> LENGTH: 16
<212> TYPE: DNA
<213> ORGANISM: Homo sapiens

<400> SEQUENCE: 72
attcaccttc gaggag                                                    16

<210> SEQ ID NO 73
<211> LENGTH: 16
<212> TYPE: DNA
<213> ORGANISM: Homo sapiens

<400> SEQUENCE: 73
cattcacctt agagga                                                    16

<210> SEQ ID NO 74
<211> LENGTH: 16
<212> TYPE: DNA
<213> ORGANISM: Homo sapiens

<400> SEQUENCE: 74
gcattcacct tagagg                                                    16

<210> SEQ ID NO 75
<211> LENGTH: 16
<212> TYPE: DNA
<213> ORGANISM: Homo sapiens

<400> SEQUENCE: 75
tgcattcacc ttagag                                                    16

<210> SEQ ID NO 76
<211> LENGTH: 16
<212> TYPE: DNA
<213> ORGANISM: Homo sapiens

<400> SEQUENCE: 76
atgcattcac cttaga                                                    16

<210> SEQ ID NO 77
<211> LENGTH: 16
<212> TYPE: DNA
<213> ORGANISM: Homo sapiens

<400> SEQUENCE: 77
aatgcattca ccttag                                                    16
```

<210> SEQ ID NO 78
<211> LENGTH: 16
<212> TYPE: DNA
<213> ORGANISM: Homo sapiens

<400> SEQUENCE: 78
aaatgcattc acctta                                                     16

<210> SEQ ID NO 79
<211> LENGTH: 16
<212> TYPE: DNA
<213> ORGANISM: Homo sapiens

<400> SEQUENCE: 79
aaaatgcatt cacctt                                                     16

<210> SEQ ID NO 80
<211> LENGTH: 16
<212> TYPE: DNA
<213> ORGANISM: Homo sapiens

<400> SEQUENCE: 80
gaaaatgcat tcacct                                                     16

<210> SEQ ID NO 81
<211> LENGTH: 16
<212> TYPE: DNA
<213> ORGANISM: Homo sapiens

<400> SEQUENCE: 81
agaaaatgca ttcacc                                                     16

<210> SEQ ID NO 82
<211> LENGTH: 16
<212> TYPE: DNA
<213> ORGANISM: Homo sapiens

<400> SEQUENCE: 82
aagaaaatgc attcac                                                     16

<210> SEQ ID NO 83
<211> LENGTH: 16
<212> TYPE: DNA
<213> ORGANISM: Homo sapiens

<400> SEQUENCE: 83
caagaaaatg cattca                                                     16

<210> SEQ ID NO 84
<211> LENGTH: 16
<212> TYPE: DNA
<213> ORGANISM: Homo sapiens

<400> SEQUENCE: 84
gcaagaaaat gcattc                                                     16

<210> SEQ ID NO 85
<211> LENGTH: 16
<212> TYPE: DNA
<213> ORGANISM: Homo sapiens

<400> SEQUENCE: 85

```
tgcaagaaaa tgcatt                                                    16

<210> SEQ ID NO 86
<211> LENGTH: 16
<212> TYPE: DNA
<213> ORGANISM: Homo sapiens

<400> SEQUENCE: 86
atgcaagaaa atgcat                                                    16

<210> SEQ ID NO 87
<211> LENGTH: 16
<212> TYPE: DNA
<213> ORGANISM: Homo sapiens

<400> SEQUENCE: 87
aatgcaagaa aatgca                                                    16

<210> SEQ ID NO 88
<211> LENGTH: 16
<212> TYPE: DNA
<213> ORGANISM: Homo sapiens

<400> SEQUENCE: 88
attctggtgg atgtgg                                                    16

<210> SEQ ID NO 89
<211> LENGTH: 16
<212> TYPE: DNA
<213> ORGANISM: Homo sapiens

<400> SEQUENCE: 89
cattctggtg gatgtg                                                    16

<210> SEQ ID NO 90
<211> LENGTH: 16
<212> TYPE: DNA
<213> ORGANISM: Homo sapiens

<400> SEQUENCE: 90
ccattctggt ggatgt                                                    16

<210> SEQ ID NO 91
<211> LENGTH: 16
<212> TYPE: DNA
<213> ORGANISM: Homo sapiens

<400> SEQUENCE: 91
gccattctgg tggatg                                                    16

<210> SEQ ID NO 92
<211> LENGTH: 16
<212> TYPE: DNA
<213> ORGANISM: Homo sapiens

<400> SEQUENCE: 92
agccattctg gtggat                                                    16

<210> SEQ ID NO 93
<211> LENGTH: 16
<212> TYPE: DNA
<213> ORGANISM: Homo sapiens

<400> SEQUENCE: 93
```
tagccattct ggtgga                                                16

<210> SEQ ID NO 94
<211> LENGTH: 16
<212> TYPE: RNA
<213> ORGANISM: Homo sapiens

<400> SEQUENCE: 94
ccaccagaau ggcuac                                                16

<210> SEQ ID NO 95
<211> LENGTH: 16
<212> TYPE: DNA
<213> ORGANISM: Homo sapiens

<400> SEQUENCE: 95
tgtagccatt ctggtg                                                16

<210> SEQ ID NO 96
<211> LENGTH: 16
<212> TYPE: DNA
<213> ORGANISM: Homo sapiens

<400> SEQUENCE: 96
ttgtagccat tctggt                                                16

<210> SEQ ID NO 97
<211> LENGTH: 16
<212> TYPE: DNA
<213> ORGANISM: Homo sapiens

<400> SEQUENCE: 97
gttgtagcca ttctgg                                                16

<210> SEQ ID NO 98
<211> LENGTH: 16
<212> TYPE: DNA
<213> ORGANISM: Homo sapiens

<400> SEQUENCE: 98
agttgtagcc attctg                                                16

<210> SEQ ID NO 99
<211> LENGTH: 16
<212> TYPE: DNA
<213> ORGANISM: Homo sapiens

<400> SEQUENCE: 99
aagttgtagc cattct                                                16

<210> SEQ ID NO 100
<211> LENGTH: 16
<212> TYPE: DNA
<213> ORGANISM: Homo sapiens

<400> SEQUENCE: 100
taagttgtag ccattc                                                16

<210> SEQ ID NO 101
<211> LENGTH: 16
<212> TYPE: DNA
<213> ORGANISM: Homo sapiens

```
<400> SEQUENCE: 101
ttaagttgta gccatt                                                       16

<210> SEQ ID NO 102
<211> LENGTH: 16
<212> TYPE: DNA
<213> ORGANISM: Homo sapiens

<400> SEQUENCE: 102
tttaagttgt agccat                                                       16

<210> SEQ ID NO 103
<211> LENGTH: 16
<212> TYPE: DNA
<213> ORGANISM: Homo sapiens

<400> SEQUENCE: 103
ttttaagttg tagcca                                                       16

<210> SEQ ID NO 104
<211> LENGTH: 16
<212> TYPE: DNA
<213> ORGANISM: Homo sapiens

<400> SEQUENCE: 104
atcatgcttt aaaaaa                                                       16

<210> SEQ ID NO 105
<211> LENGTH: 16
<212> TYPE: DNA
<213> ORGANISM: Homo sapiens

<400> SEQUENCE: 105
catcatgctt taaaaa                                                       16

<210> SEQ ID NO 106
<211> LENGTH: 16
<212> TYPE: DNA
<213> ORGANISM: Homo sapiens

<400> SEQUENCE: 106
ccatcatgct ttaaaa                                                       16

<210> SEQ ID NO 107
<211> LENGTH: 16
<212> TYPE: DNA
<213> ORGANISM: Homo sapiens

<400> SEQUENCE: 107
tccatcatgc tttaaa                                                       16

<210> SEQ ID NO 108
<211> LENGTH: 16
<212> TYPE: DNA
<213> ORGANISM: Homo sapiens

<400> SEQUENCE: 108
ttccatcatg ctttaa                                                       16

<210> SEQ ID NO 109
<211> LENGTH: 16
<212> TYPE: DNA
<213> ORGANISM: Homo sapiens
```

```
<400> SEQUENCE: 109
attccatcat gcttta                                                    16

<210> SEQ ID NO 110
<211> LENGTH: 16
<212> TYPE: DNA
<213> ORGANISM: Homo sapiens

<400> SEQUENCE: 110
aattccatca tgcttt                                                    16

<210> SEQ ID NO 111
<211> LENGTH: 16
<212> TYPE: DNA
<213> ORGANISM: Homo sapiens

<400> SEQUENCE: 111
aaattccatc atgctt                                                    16

<210> SEQ ID NO 112
<211> LENGTH: 16
<212> TYPE: DNA
<213> ORGANISM: Homo sapiens

<400> SEQUENCE: 112
aaaattccat catgct                                                    16

<210> SEQ ID NO 113
<211> LENGTH: 16
<212> TYPE: DNA
<213> ORGANISM: Homo sapiens

<400> SEQUENCE: 113
taaaattcca tcatgc                                                    16

<210> SEQ ID NO 114
<211> LENGTH: 16
<212> TYPE: DNA
<213> ORGANISM: Homo sapiens

<400> SEQUENCE: 114
ctaaaattcc atcatg                                                    16

<210> SEQ ID NO 115
<211> LENGTH: 16
<212> TYPE: DNA
<213> ORGANISM: Homo sapiens

<400> SEQUENCE: 115
gctaaaattc catcat                                                    16

<210> SEQ ID NO 116
<211> LENGTH: 16
<212> TYPE: DNA
<213> ORGANISM: Homo sapiens

<400> SEQUENCE: 116
agctaaaatt ccatca                                                    16

<210> SEQ ID NO 117
<211> LENGTH: 16
<212> TYPE: DNA
```

<213> ORGANISM: Homo sapiens

<400> SEQUENCE: 117
cagctaaaat tccatc                                              16

<210> SEQ ID NO 118
<211> LENGTH: 16
<212> TYPE: DNA
<213> ORGANISM: Homo sapiens

<400> SEQUENCE: 118
gcagctaaaa ttccat                                              16

<210> SEQ ID NO 119
<211> LENGTH: 16
<212> TYPE: DNA
<213> ORGANISM: Homo sapiens

<400> SEQUENCE: 119
tgcagctaaa attcca                                              16

<210> SEQ ID NO 120
<211> LENGTH: 16
<212> TYPE: DNA
<213> ORGANISM: Homo sapiens

<400> SEQUENCE: 120
atgctttaaa aaaaaa                                              16

<210> SEQ ID NO 121
<211> LENGTH: 16
<212> TYPE: DNA
<213> ORGANISM: Homo sapiens

<400> SEQUENCE: 121
catgctttaa aaaaaa                                              16

<210> SEQ ID NO 122
<211> LENGTH: 16
<212> TYPE: DNA
<213> ORGANISM: Homo sapiens

<400> SEQUENCE: 122
tcatgcttta aaaaaa                                              16

<210> SEQ ID NO 123
<211> LENGTH: 16
<212> TYPE: DNA
<213> ORGANISM: Homo sapiens

<400> SEQUENCE: 123
atcatgcttt aaaaaa                                              16

<210> SEQ ID NO 124
<211> LENGTH: 16
<212> TYPE: DNA
<213> ORGANISM: Homo sapiens

<400> SEQUENCE: 124
attagtccag cagaac                                              16

<210> SEQ ID NO 125
<211> LENGTH: 16

<212> TYPE: DNA
<213> ORGANISM: Homo sapiens

<400> SEQUENCE: 125
cattagtcca gcagaa                                                   16

<210> SEQ ID NO 126
<211> LENGTH: 16
<212> TYPE: DNA
<213> ORGANISM: Homo sapiens

<400> SEQUENCE: 126
tcattagtcc agcaga                                                   16

<210> SEQ ID NO 127
<211> LENGTH: 16
<212> TYPE: DNA
<213> ORGANISM: Homo sapiens

<400> SEQUENCE: 127
ttcattagtc cagcag                                                   16

<210> SEQ ID NO 128
<211> LENGTH: 16
<212> TYPE: DNA
<213> ORGANISM: Homo sapiens

<400> SEQUENCE: 128
cttcattagt ccagca                                                   16

<210> SEQ ID NO 129
<211> LENGTH: 16
<212> TYPE: DNA
<213> ORGANISM: Homo sapiens

<400> SEQUENCE: 129
acttcattag tccagc                                                   16

<210> SEQ ID NO 130
<211> LENGTH: 16
<212> TYPE: DNA
<213> ORGANISM: Homo sapiens

<400> SEQUENCE: 130
cacttcatta gtccag                                                   16

<210> SEQ ID NO 131
<211> LENGTH: 16
<212> TYPE: DNA
<213> ORGANISM: Homo sapiens

<400> SEQUENCE: 131
gcacttcatt agtcca                                                   16

<210> SEQ ID NO 132
<211> LENGTH: 16
<212> TYPE: DNA
<213> ORGANISM: Homo sapiens

<400> SEQUENCE: 132
ggcacttcat tagtcc                                                   16

<210> SEQ ID NO 133

```
<211> LENGTH: 16
<212> TYPE: DNA
<213> ORGANISM: Homo sapiens

<400> SEQUENCE: 133
tggcacttca ttagtc                                                   16

<210> SEQ ID NO 134
<211> LENGTH: 16
<212> TYPE: DNA
<213> ORGANISM: Homo sapiens

<400> SEQUENCE: 134
gtggcacttc attagt                                                   16

<210> SEQ ID NO 135
<211> LENGTH: 16
<212> TYPE: DNA
<213> ORGANISM: Homo sapiens

<400> SEQUENCE: 135
agtggcactt cattag                                                   16

<210> SEQ ID NO 136
<211> LENGTH: 16
<212> TYPE: DNA
<213> ORGANISM: Homo sapiens

<400> SEQUENCE: 136
gagtggcact tcatta                                                   16

<210> SEQ ID NO 137
<211> LENGTH: 16
<212> TYPE: DNA
<213> ORGANISM: Homo sapiens

<400> SEQUENCE: 137
ggagtggcac ttcatt                                                   16

<210> SEQ ID NO 138
<211> LENGTH: 16
<212> TYPE: DNA
<213> ORGANISM: Homo sapiens

<400> SEQUENCE: 138
tggagtggca cttcat                                                   16

<210> SEQ ID NO 139
<211> LENGTH: 16
<212> TYPE: DNA
<213> ORGANISM: Homo sapiens

<400> SEQUENCE: 139
gtggagtggc acttca                                                   16

<210> SEQ ID NO 140
<211> LENGTH: 16
<212> TYPE: DNA
<213> ORGANISM: Homo sapiens

<400> SEQUENCE: 140
atgtgctcta tcctca                                                   16
```

```
<210> SEQ ID NO 141
<211> LENGTH: 16
<212> TYPE: DNA
<213> ORGANISM: Homo sapiens

<400> SEQUENCE: 141
catgtgctct atcctc                                                       16

<210> SEQ ID NO 142
<211> LENGTH: 16
<212> TYPE: DNA
<213> ORGANISM: Homo sapiens

<400> SEQUENCE: 142
acatgtgctc tatcct                                                       16

<210> SEQ ID NO 143
<211> LENGTH: 16
<212> TYPE: RNA
<213> ORGANISM: Homo sapiens

<400> SEQUENCE: 143
ggauagagca caugug                                                       16

<210> SEQ ID NO 144
<211> LENGTH: 16
<212> TYPE: DNA
<213> ORGANISM: Homo sapiens

<400> SEQUENCE: 144
tcacatgtgc tctatc                                                       16

<210> SEQ ID NO 145
<211> LENGTH: 16
<212> TYPE: DNA
<213> ORGANISM: Homo sapiens

<400> SEQUENCE: 145
ctcacatgtg ctctat                                                       16

<210> SEQ ID NO 146
<211> LENGTH: 16
<212> TYPE: RNA
<213> ORGANISM: Homo sapiens

<400> SEQUENCE: 146
uagagcacau gugaga                                                       16

<210> SEQ ID NO 147
<211> LENGTH: 16
<212> TYPE: DNA
<213> ORGANISM: Homo sapiens

<400> SEQUENCE: 147
atctcacatg tgctct                                                       16

<210> SEQ ID NO 148
<211> LENGTH: 16
<212> TYPE: DNA
<213> ORGANISM: Homo sapiens

<400> SEQUENCE: 148
aatctcacat gtgctc                                                       16
```

```
<210> SEQ ID NO 149
<211> LENGTH: 16
<212> TYPE: DNA
<213> ORGANISM: Homo sapiens

<400> SEQUENCE: 149
aaatctcaca tgtgct                                               16

<210> SEQ ID NO 150
<211> LENGTH: 16
<212> TYPE: DNA
<213> ORGANISM: Homo sapiens

<400> SEQUENCE: 150
aaaatctcac atgtgc                                               16

<210> SEQ ID NO 151
<211> LENGTH: 16
<212> TYPE: DNA
<213> ORGANISM: Homo sapiens

<400> SEQUENCE: 151
taaaatctca catgtg                                               16

<210> SEQ ID NO 152
<211> LENGTH: 16
<212> TYPE: DNA
<213> ORGANISM: Homo sapiens

<400> SEQUENCE: 152
gtaaaatctc acatgt                                               16

<210> SEQ ID NO 153
<211> LENGTH: 16
<212> TYPE: DNA
<213> ORGANISM: Homo sapiens

<400> SEQUENCE: 153
agtaaaatct cacatg                                               16

<210> SEQ ID NO 154
<211> LENGTH: 16
<212> TYPE: DNA
<213> ORGANISM: Homo sapiens

<400> SEQUENCE: 154
aagtaaaatc tcacat                                               16

<210> SEQ ID NO 155
<211> LENGTH: 16
<212> TYPE: DNA
<213> ORGANISM: Homo sapiens

<400> SEQUENCE: 155
aaagtaaaat ctcaca                                               16

<210> SEQ ID NO 156
<211> LENGTH: 16
<212> TYPE: DNA
<213> ORGANISM: Homo sapiens

<400> SEQUENCE: 156
attaaagaag aaaaaa                                               16
```

<210> SEQ ID NO 157
<211> LENGTH: 16
<212> TYPE: DNA
<213> ORGANISM: Homo sapiens

<400> SEQUENCE: 157
cattaaagaa gaaaaa                                                         16

<210> SEQ ID NO 158
<211> LENGTH: 16
<212> TYPE: DNA
<213> ORGANISM: Homo sapiens

<400> SEQUENCE: 158
tcattaaaga agaaaa                                                         16

<210> SEQ ID NO 159
<211> LENGTH: 16
<212> TYPE: DNA
<213> ORGANISM: Homo sapiens

<400> SEQUENCE: 159
ctcattaaag aagaaa                                                         16

<210> SEQ ID NO 160
<211> LENGTH: 16
<212> TYPE: DNA
<213> ORGANISM: Homo sapiens

<400> SEQUENCE: 160
cctcattaaa gaagaa                                                         16

<210> SEQ ID NO 161
<211> LENGTH: 16
<212> TYPE: DNA
<213> ORGANISM: Homo sapiens

<400> SEQUENCE: 161
tcctcattaa agaaga                                                         16

<210> SEQ ID NO 162
<211> LENGTH: 16
<212> TYPE: DNA
<213> ORGANISM: Homo sapiens

<400> SEQUENCE: 162
atcctcatta aagaag                                                         16

<210> SEQ ID NO 163
<211> LENGTH: 16
<212> TYPE: DNA
<213> ORGANISM: Homo sapiens

<400> SEQUENCE: 163
tatcctcatt aaagaa                                                         16

<210> SEQ ID NO 164
<211> LENGTH: 16
<212> TYPE: DNA
<213> ORGANISM: Homo sapiens

<400> SEQUENCE: 164
ctatcctcat taaaga                                                    16

<210> SEQ ID NO 165
<211> LENGTH: 16
<212> TYPE: DNA
<213> ORGANISM: Homo sapiens

<400> SEQUENCE: 165
tctatcctca ttaaag                                                    16

<210> SEQ ID NO 166
<211> LENGTH: 16
<212> TYPE: DNA
<213> ORGANISM: Homo sapiens

<400> SEQUENCE: 166
ctctatcctc attaaa                                                    16

<210> SEQ ID NO 167
<211> LENGTH: 16
<212> TYPE: DNA
<213> ORGANISM: Homo sapiens

<400> SEQUENCE: 167
gctctatcct cattaa                                                    16

<210> SEQ ID NO 168
<211> LENGTH: 16
<212> TYPE: DNA
<213> ORGANISM: Homo sapiens

<400> SEQUENCE: 168
tgctctatcc tcatta                                                    16

<210> SEQ ID NO 169
<211> LENGTH: 16
<212> TYPE: DNA
<213> ORGANISM: Homo sapiens

<400> SEQUENCE: 169
gtgctctatc ctcatt                                                    16

<210> SEQ ID NO 170
<211> LENGTH: 16
<212> TYPE: RNA
<213> ORGANISM: Homo sapiens

<400> SEQUENCE: 170
augaggauag agcaca                                                    16

<210> SEQ ID NO 171
<211> LENGTH: 16
<212> TYPE: DNA
<213> ORGANISM: Homo sapiens

<400> SEQUENCE: 171
atcctccctc ctttgc                                                    16

<210> SEQ ID NO 172
<211> LENGTH: 16
<212> TYPE: DNA
<213> ORGANISM: Homo sapiens

<400> SEQUENCE: 172

```
catcctccct cctttg                                                  16

<210> SEQ ID NO 173
<211> LENGTH: 16
<212> TYPE: DNA
<213> ORGANISM: Homo sapiens

<400> SEQUENCE: 173
gcatcctccc tccttt                                                  16

<210> SEQ ID NO 174
<211> LENGTH: 16
<212> TYPE: DNA
<213> ORGANISM: Homo sapiens

<400> SEQUENCE: 174
agcatcctcc ctcctt                                                  16

<210> SEQ ID NO 175
<211> LENGTH: 16
<212> TYPE: DNA
<213> ORGANISM: Homo sapiens

<400> SEQUENCE: 175
cagcatcctc cctcct                                                  16

<210> SEQ ID NO 176
<211> LENGTH: 16
<212> TYPE: DNA
<213> ORGANISM: Homo sapiens

<400> SEQUENCE: 176
acagcatcct ccctcc                                                  16

<210> SEQ ID NO 177
<211> LENGTH: 16
<212> TYPE: DNA
<213> ORGANISM: Homo sapiens

<400> SEQUENCE: 177
cacagcatcc tccctc                                                  16

<210> SEQ ID NO 178
<211> LENGTH: 16
<212> TYPE: DNA
<213> ORGANISM: Homo sapiens

<400> SEQUENCE: 178
ccacagcatc ctccct                                                  16

<210> SEQ ID NO 179
<211> LENGTH: 16
<212> TYPE: DNA
<213> ORGANISM: Homo sapiens

<400> SEQUENCE: 179
accacagcat cctccc                                                  16

<210> SEQ ID NO 180
<211> LENGTH: 16
<212> TYPE: RNA
<213> ORGANISM: Homo sapiens
```

```
<400> SEQUENCE: 180
ggaggaugcu gugguc                                                       16

<210> SEQ ID NO 181
<211> LENGTH: 16
<212> TYPE: DNA
<213> ORGANISM: Homo sapiens

<400> SEQUENCE: 181
tgaccacagc atcctc                                                       16

<210> SEQ ID NO 182
<211> LENGTH: 16
<212> TYPE: DNA
<213> ORGANISM: Homo sapiens

<400> SEQUENCE: 182
atgaccacag catcct                                                       16

<210> SEQ ID NO 183
<211> LENGTH: 16
<212> TYPE: DNA
<213> ORGANISM: Homo sapiens

<400> SEQUENCE: 183
gatgaccaca gcatcc                                                       16

<210> SEQ ID NO 184
<211> LENGTH: 16
<212> TYPE: DNA
<213> ORGANISM: Homo sapiens

<400> SEQUENCE: 184
ggatgaccac agcatc                                                       16

<210> SEQ ID NO 185
<211> LENGTH: 16
<212> TYPE: DNA
<213> ORGANISM: Homo sapiens

<400> SEQUENCE: 185
aggatgacca cagcat                                                       16

<210> SEQ ID NO 186
<211> LENGTH: 16
<212> TYPE: DNA
<213> ORGANISM: Homo sapiens

<400> SEQUENCE: 186
aaggatgacc acagca                                                       16

<210> SEQ ID NO 187
<211> LENGTH: 16
<212> TYPE: DNA
<213> ORGANISM: Homo sapiens

<400> SEQUENCE: 187
atttcctgta caggga                                                       16

<210> SEQ ID NO 188
<211> LENGTH: 16
<212> TYPE: DNA
<213> ORGANISM: Homo sapiens
```

-continued

<400> SEQUENCE: 188
catttcctgt acaggg                                                     16

<210> SEQ ID NO 189
<211> LENGTH: 16
<212> TYPE: DNA
<213> ORGANISM: Homo sapiens

<400> SEQUENCE: 189
gcatttcctg tacagg                                                     16

<210> SEQ ID NO 190
<211> LENGTH: 16
<212> TYPE: DNA
<213> ORGANISM: Homo sapiens

<400> SEQUENCE: 190
ggcatttcct gtacag                                                     16

<210> SEQ ID NO 191
<211> LENGTH: 16
<212> TYPE: DNA
<213> ORGANISM: Homo sapiens

<400> SEQUENCE: 191
aggcatttcc tgtaca                                                     16

<210> SEQ ID NO 192
<211> LENGTH: 16
<212> TYPE: DNA
<213> ORGANISM: Homo sapiens

<400> SEQUENCE: 192
gaggcatttc ctgtac                                                     16

<210> SEQ ID NO 193
<211> LENGTH: 16
<212> TYPE: DNA
<213> ORGANISM: Homo sapiens

<400> SEQUENCE: 193
agaggcattt cctgta                                                     16

<210> SEQ ID NO 194
<211> LENGTH: 16
<212> TYPE: DNA
<213> ORGANISM: Homo sapiens

<400> SEQUENCE: 194
aagaggcatt tcctgt                                                     16

<210> SEQ ID NO 195
<211> LENGTH: 16
<212> TYPE: DNA
<213> ORGANISM: Homo sapiens

<400> SEQUENCE: 195
gaagaggcat ttcctg                                                     16

<210> SEQ ID NO 196
<211> LENGTH: 16
<212> TYPE: DNA

```
<213> ORGANISM: Homo sapiens

<400> SEQUENCE: 196
agaagaggca tttcct                                              16

<210> SEQ ID NO 197
<211> LENGTH: 16
<212> TYPE: DNA
<213> ORGANISM: Homo sapiens

<400> SEQUENCE: 197
aagaagaggc atttcc                                              16

<210> SEQ ID NO 198
<211> LENGTH: 16
<212> TYPE: DNA
<213> ORGANISM: Homo sapiens

<400> SEQUENCE: 198
taagaagagg catttc                                              16

<210> SEQ ID NO 199
<211> LENGTH: 16
<212> TYPE: DNA
<213> ORGANISM: Homo sapiens

<400> SEQUENCE: 199
gtaagaagag gcattt                                              16

<210> SEQ ID NO 200
<211> LENGTH: 16
<212> TYPE: DNA
<213> ORGANISM: Homo sapiens

<400> SEQUENCE: 200
agtaagaaga ggcatt                                              16

<210> SEQ ID NO 201
<211> LENGTH: 16
<212> TYPE: DNA
<213> ORGANISM: Homo sapiens

<400> SEQUENCE: 201
aagtaagaag aggcat                                              16

<210> SEQ ID NO 202
<211> LENGTH: 16
<212> TYPE: DNA
<213> ORGANISM: Homo sapiens

<400> SEQUENCE: 202
gaagtaagaa gaggca                                              16

<210> SEQ ID NO 203
<211> LENGTH: 16
<212> TYPE: DNA
<213> ORGANISM: Homo sapiens

<400> SEQUENCE: 203
attcgatggt acccaa                                              16

<210> SEQ ID NO 204
<211> LENGTH: 16
```

```
<212> TYPE: DNA
<213> ORGANISM: Homo sapiens

<400> SEQUENCE: 204
cattcgatgg tacccca                                                     16

<210> SEQ ID NO 205
<211> LENGTH: 16
<212> TYPE: DNA
<213> ORGANISM: Homo sapiens

<400> SEQUENCE: 205
tcattcgatg gtaccc                                                      16

<210> SEQ ID NO 206
<211> LENGTH: 16
<212> TYPE: DNA
<213> ORGANISM: Homo sapiens

<400> SEQUENCE: 206
gtcattcgat ggtacc                                                      16

<210> SEQ ID NO 207
<211> LENGTH: 16
<212> TYPE: DNA
<213> ORGANISM: Homo sapiens

<400> SEQUENCE: 207
agtcattcga tggtac                                                      16

<210> SEQ ID NO 208
<211> LENGTH: 16
<212> TYPE: DNA
<213> ORGANISM: Homo sapiens

<400> SEQUENCE: 208
cagtcattcg atggta                                                      16

<210> SEQ ID NO 209
<211> LENGTH: 16
<212> TYPE: DNA
<213> ORGANISM: Homo sapiens

<400> SEQUENCE: 209
acagtcattc gatggt                                                      16

<210> SEQ ID NO 210
<211> LENGTH: 16
<212> TYPE: DNA
<213> ORGANISM: Homo sapiens

<400> SEQUENCE: 210
gacagtcatt cgatgg                                                      16

<210> SEQ ID NO 211
<211> LENGTH: 16
<212> TYPE: DNA
<213> ORGANISM: Homo sapiens

<400> SEQUENCE: 211
tgacagtcat tcgatg                                                      16

<210> SEQ ID NO 212
```

```
<211> LENGTH: 16
<212> TYPE: DNA
<213> ORGANISM: Homo sapiens

<400> SEQUENCE: 212
ctgacagtca ttcgat                                                    16

<210> SEQ ID NO 213
<211> LENGTH: 16
<212> TYPE: DNA
<213> ORGANISM: Homo sapiens

<400> SEQUENCE: 213
tctgacagtc attcga                                                    16

<210> SEQ ID NO 214
<211> LENGTH: 16
<212> TYPE: DNA
<213> ORGANISM: Homo sapiens

<400> SEQUENCE: 214
ttctgacagt cattcg                                                    16

<210> SEQ ID NO 215
<211> LENGTH: 16
<212> TYPE: DNA
<213> ORGANISM: Homo sapiens

<400> SEQUENCE: 215
gttctgacag tcattc                                                    16

<210> SEQ ID NO 216
<211> LENGTH: 16
<212> TYPE: DNA
<213> ORGANISM: Homo sapiens

<400> SEQUENCE: 216
tgttctgaca gtcatt                                                    16

<210> SEQ ID NO 217
<211> LENGTH: 16
<212> TYPE: DNA
<213> ORGANISM: Homo sapiens

<400> SEQUENCE: 217
ctgttctgac agtcat                                                    16

<210> SEQ ID NO 218
<211> LENGTH: 16
<212> TYPE: DNA
<213> ORGANISM: Homo sapiens

<400> SEQUENCE: 218
tctgttctga cagtca                                                    16

<210> SEQ ID NO 219
<211> LENGTH: 16
<212> TYPE: DNA
<213> ORGANISM: Homo sapiens

<400> SEQUENCE: 219
attattgtaa ctacca                                                    16
```

```
<210> SEQ ID NO 220
<211> LENGTH: 16
<212> TYPE: DNA
<213> ORGANISM: Homo sapiens

<400> SEQUENCE: 220
cattattgta actacc                                                     16

<210> SEQ ID NO 221
<211> LENGTH: 16
<212> TYPE: RNA
<213> ORGANISM: Homo sapiens

<400> SEQUENCE: 221
guaguuacaa uaaugc                                                     16

<210> SEQ ID NO 222
<211> LENGTH: 16
<212> TYPE: DNA
<213> ORGANISM: Homo sapiens

<400> SEQUENCE: 222
ggcattattg taacta                                                     16

<210> SEQ ID NO 223
<211> LENGTH: 16
<212> TYPE: DNA
<213> ORGANISM: Homo sapiens

<400> SEQUENCE: 223
tggcattatt gtaact                                                     16

<210> SEQ ID NO 224
<211> LENGTH: 16
<212> TYPE: DNA
<213> ORGANISM: Homo sapiens

<400> SEQUENCE: 224
atggcattat tgtaac                                                     16

<210> SEQ ID NO 225
<211> LENGTH: 16
<212> TYPE: DNA
<213> ORGANISM: Homo sapiens

<400> SEQUENCE: 225
aatggcatta ttgtaa                                                     16

<210> SEQ ID NO 226
<211> LENGTH: 16
<212> TYPE: DNA
<213> ORGANISM: Homo sapiens

<400> SEQUENCE: 226
aaatggcatt attgta                                                     16

<210> SEQ ID NO 227
<211> LENGTH: 16
<212> TYPE: DNA
<213> ORGANISM: Homo sapiens

<400> SEQUENCE: 227
aaaatggcat tattgt                                                     16
```

```
<210> SEQ ID NO 228
<211> LENGTH: 16
<212> TYPE: DNA
<213> ORGANISM: Homo sapiens

<400> SEQUENCE: 228
caaaatggca ttattg                                                        16

<210> SEQ ID NO 229
<211> LENGTH: 16
<212> TYPE: DNA
<213> ORGANISM: Homo sapiens

<400> SEQUENCE: 229
acaaaatggc attatt                                                        16

<210> SEQ ID NO 230
<211> LENGTH: 16
<212> TYPE: DNA
<213> ORGANISM: Homo sapiens

<400> SEQUENCE: 230
tacaaaatgg cattat                                                        16

<210> SEQ ID NO 231
<211> LENGTH: 16
<212> TYPE: DNA
<213> ORGANISM: Homo sapiens

<400> SEQUENCE: 231
ctacaaaatg gcatta                                                        16

<210> SEQ ID NO 232
<211> LENGTH: 16
<212> TYPE: DNA
<213> ORGANISM: Homo sapiens

<400> SEQUENCE: 232
actacaaaat ggcatt                                                        16

<210> SEQ ID NO 233
<211> LENGTH: 16
<212> TYPE: DNA
<213> ORGANISM: Homo sapiens

<400> SEQUENCE: 233
gactacaaaa tggcat                                                        16

<210> SEQ ID NO 234
<211> LENGTH: 16
<212> TYPE: DNA
<213> ORGANISM: Homo sapiens

<400> SEQUENCE: 234
ggactacaaa atggca                                                        16

<210> SEQ ID NO 235
<211> LENGTH: 16
<212> TYPE: DNA
<213> ORGANISM: Homo sapiens

<400> SEQUENCE: 235
tgttagaaaa cagcat                                                        16
```

```
<210> SEQ ID NO 236
<211> LENGTH: 16
<212> TYPE: DNA
<213> ORGANISM: Homo sapiens

<400> SEQUENCE: 236
ctgttagaaa acagca                                                       16

<210> SEQ ID NO 237
<211> LENGTH: 16
<212> TYPE: DNA
<213> ORGANISM: Homo sapiens

<400> SEQUENCE: 237
atatgtctga agcagc                                                       16

<210> SEQ ID NO 238
<211> LENGTH: 16
<212> TYPE: DNA
<213> ORGANISM: Homo sapiens

<400> SEQUENCE: 238
catatgtctg aagcag                                                       16

<210> SEQ ID NO 239
<211> LENGTH: 16
<212> TYPE: DNA
<213> ORGANISM: Homo sapiens

<400> SEQUENCE: 239
acatatgtct gaagca                                                       16

<210> SEQ ID NO 240
<211> LENGTH: 16
<212> TYPE: DNA
<213> ORGANISM: Homo sapiens

<400> SEQUENCE: 240
gacatatgtc tgaagc                                                       16

<210> SEQ ID NO 241
<211> LENGTH: 16
<212> TYPE: DNA
<213> ORGANISM: Homo sapiens

<400> SEQUENCE: 241
agacatatgt ctgaag                                                       16

<210> SEQ ID NO 242
<211> LENGTH: 16
<212> TYPE: DNA
<213> ORGANISM: Homo sapiens

<400> SEQUENCE: 242
cagacatatg tctgaa                                                       16

<210> SEQ ID NO 243
<211> LENGTH: 16
<212> TYPE: DNA
<213> ORGANISM: Homo sapiens

<400> SEQUENCE: 243
```

```
acagacatat gtctga                                                    16

<210> SEQ ID NO 244
<211> LENGTH: 16
<212> TYPE: DNA
<213> ORGANISM: Homo sapiens

<400> SEQUENCE: 244
cacagacata tgtctg                                                    16

<210> SEQ ID NO 245
<211> LENGTH: 16
<212> TYPE: DNA
<213> ORGANISM: Homo sapiens

<400> SEQUENCE: 245
acacagacat atgtct                                                    16

<210> SEQ ID NO 246
<211> LENGTH: 16
<212> TYPE: DNA
<213> ORGANISM: Homo sapiens

<400> SEQUENCE: 246
cacacagaca tatgtc                                                    16

<210> SEQ ID NO 247
<211> LENGTH: 16
<212> TYPE: DNA
<213> ORGANISM: Homo sapiens

<400> SEQUENCE: 247
acacacagac atatgt                                                    16

<210> SEQ ID NO 248
<211> LENGTH: 16
<212> TYPE: DNA
<213> ORGANISM: Homo sapiens

<400> SEQUENCE: 248
tacacacaga catatg                                                    16

<210> SEQ ID NO 249
<211> LENGTH: 16
<212> TYPE: DNA
<213> ORGANISM: Homo sapiens

<400> SEQUENCE: 249
gtacacacag acatat                                                    16

<210> SEQ ID NO 250
<211> LENGTH: 16
<212> TYPE: DNA
<213> ORGANISM: Homo sapiens

<400> SEQUENCE: 250
cgtacacaca gacata                                                    16

<210> SEQ ID NO 251
<211> LENGTH: 16
<212> TYPE: DNA
<213> ORGANISM: Homo sapiens

<400> SEQUENCE: 251
```

```
gcgtacacac agacat                                                       16

<210> SEQ ID NO 252
<211> LENGTH: 16
<212> TYPE: DNA
<213> ORGANISM: Homo sapiens

<400> SEQUENCE: 252
agcgtacaca cagaca                                                       16

<210> SEQ ID NO 253
<211> LENGTH: 16
<212> TYPE: DNA
<213> ORGANISM: Homo sapiens

<400> SEQUENCE: 253
atggatcccg taaaaa                                                       16

<210> SEQ ID NO 254
<211> LENGTH: 16
<212> TYPE: DNA
<213> ORGANISM: Homo sapiens

<400> SEQUENCE: 254
catggatccc gtaaaa                                                       16

<210> SEQ ID NO 255
<211> LENGTH: 16
<212> TYPE: DNA
<213> ORGANISM: Homo sapiens

<400> SEQUENCE: 255
ccatggatcc cgtaaa                                                       16

<210> SEQ ID NO 256
<211> LENGTH: 16
<212> TYPE: DNA
<213> ORGANISM: Homo sapiens

<400> SEQUENCE: 256
tccatggatc ccgtaa                                                       16

<210> SEQ ID NO 257
<211> LENGTH: 16
<212> TYPE: DNA
<213> ORGANISM: Homo sapiens

<400> SEQUENCE: 257
ttccatggat cccgta                                                       16

<210> SEQ ID NO 258
<211> LENGTH: 16
<212> TYPE: DNA
<213> ORGANISM: Homo sapiens

<400> SEQUENCE: 258
attccatgga tcccgt                                                       16

<210> SEQ ID NO 259
<211> LENGTH: 16
<212> TYPE: DNA
<213> ORGANISM: Homo sapiens
```

```
<400> SEQUENCE: 259
aattccatgg atcccg                                                    16

<210> SEQ ID NO 260
<211> LENGTH: 16
<212> TYPE: DNA
<213> ORGANISM: Homo sapiens

<400> SEQUENCE: 260
caattccatg gatccc                                                    16

<210> SEQ ID NO 261
<211> LENGTH: 16
<212> TYPE: DNA
<213> ORGANISM: Homo sapiens

<400> SEQUENCE: 261
ccaattccat ggatcc                                                    16

<210> SEQ ID NO 262
<211> LENGTH: 16
<212> TYPE: DNA
<213> ORGANISM: Homo sapiens

<400> SEQUENCE: 262
accaattcca tggatc                                                    16

<210> SEQ ID NO 263
<211> LENGTH: 16
<212> TYPE: DNA
<213> ORGANISM: Homo sapiens

<400> SEQUENCE: 263
aaccaattcc atggat                                                    16

<210> SEQ ID NO 264
<211> LENGTH: 16
<212> TYPE: DNA
<213> ORGANISM: Homo sapiens

<400> SEQUENCE: 264
caaccaattc catgga                                                    16

<210> SEQ ID NO 265
<211> LENGTH: 16
<212> TYPE: DNA
<213> ORGANISM: Homo sapiens

<400> SEQUENCE: 265
ccaaccaatt ccatgg                                                    16

<210> SEQ ID NO 266
<211> LENGTH: 16
<212> TYPE: DNA
<213> ORGANISM: Homo sapiens

<400> SEQUENCE: 266
tccaaccaat tccatg                                                    16

<210> SEQ ID NO 267
<211> LENGTH: 16
<212> TYPE: DNA
<213> ORGANISM: Homo sapiens
```

```
<400> SEQUENCE: 267
atccaaccaa ttccat                                                   16

<210> SEQ ID NO 268
<211> LENGTH: 16
<212> TYPE: DNA
<213> ORGANISM: Homo sapiens

<400> SEQUENCE: 268
aatccaacca attcca                                                   16

<210> SEQ ID NO 269
<211> LENGTH: 16
<212> TYPE: RNA
<213> ORGANISM: Homo sapiens

<400> SEQUENCE: 269
auuaaaggag caggau                                                   16

<210> SEQ ID NO 270
<211> LENGTH: 16
<212> TYPE: RNA
<213> ORGANISM: Homo sapiens

<400> SEQUENCE: 270
uuaaaggagc aggaug                                                   16

<210> SEQ ID NO 271
<211> LENGTH: 16
<212> TYPE: RNA
<213> ORGANISM: Homo sapiens

<400> SEQUENCE: 271
uaaaggagca ggauga                                                   16

<210> SEQ ID NO 272
<211> LENGTH: 16
<212> TYPE: RNA
<213> ORGANISM: Homo sapiens

<400> SEQUENCE: 272
aaaggagcag gaugaa                                                   16

<210> SEQ ID NO 273
<211> LENGTH: 16
<212> TYPE: RNA
<213> ORGANISM: Homo sapiens

<400> SEQUENCE: 273
aaggagcagg augaaa                                                   16

<210> SEQ ID NO 274
<211> LENGTH: 16
<212> TYPE: RNA
<213> ORGANISM: Homo sapiens

<400> SEQUENCE: 274
aggagcagga ugaaaa                                                   16

<210> SEQ ID NO 275
<211> LENGTH: 16
<212> TYPE: RNA
```

<213> ORGANISM: Homo sapiens

<400> SEQUENCE: 275
ggagcaggau gaaaag                                                    16

<210> SEQ ID NO 276
<211> LENGTH: 16
<212> TYPE: RNA
<213> ORGANISM: Homo sapiens

<400> SEQUENCE: 276
uucagcacuu ucuuau                                                    16

<210> SEQ ID NO 277
<211> LENGTH: 16
<212> TYPE: RNA
<213> ORGANISM: Homo sapiens

<400> SEQUENCE: 277
ucagcacuuu cuuaug                                                    16

<210> SEQ ID NO 278
<211> LENGTH: 16
<212> TYPE: RNA
<213> ORGANISM: Homo sapiens

<400> SEQUENCE: 278
cagcacuuuc uuaugc                                                    16

<210> SEQ ID NO 279
<211> LENGTH: 16
<212> TYPE: RNA
<213> ORGANISM: Homo sapiens

<400> SEQUENCE: 279
agcacuuucu uaugca                                                    16

<210> SEQ ID NO 280
<211> LENGTH: 16
<212> TYPE: RNA
<213> ORGANISM: Homo sapiens

<400> SEQUENCE: 280
gcacuuucuu augcaa                                                    16

<210> SEQ ID NO 281
<211> LENGTH: 16
<212> TYPE: RNA
<213> ORGANISM: Homo sapiens

<400> SEQUENCE: 281 cacuucuua ugcaag                                                     16

<210> SEQ ID NO 282
<211> LENGTH: 16
<212> TYPE: RNA
<213> ORGANISM: Homo sapiens

<400> SEQUENCE: 282 acuucuuau gcaagg                                                     16

<210> SEQ ID NO 283
<211> LENGTH: 16

```
<212> TYPE: RNA
<213> ORGANISM: Homo sapiens

<400> SEQUENCE: 283
cuuucuuaug caagga                                                   16

<210> SEQ ID NO 284
<211> LENGTH: 16
<212> TYPE: RNA
<213> ORGANISM: Homo sapiens

<400> SEQUENCE: 284
uuucuuaugc aaggag                                                   16

<210> SEQ ID NO 285
<211> LENGTH: 16
<212> TYPE: RNA
<213> ORGANISM: Homo sapiens

<400> SEQUENCE: 285
uucuuaugca aggagc                                                   16

<210> SEQ ID NO 286
<211> LENGTH: 16
<212> TYPE: RNA
<213> ORGANISM: Homo sapiens

<400> SEQUENCE: 286
ucuuaugcaa ggagcu                                                   16

<210> SEQ ID NO 287
<211> LENGTH: 16
<212> TYPE: RNA
<213> ORGANISM: Homo sapiens

<400> SEQUENCE: 287
cuuaugcaag gagcua                                                   16

<210> SEQ ID NO 288
<211> LENGTH: 16
<212> TYPE: RNA
<213> ORGANISM: Homo sapiens

<400> SEQUENCE: 288
uuaugcaagg agcuaa                                                   16

<210> SEQ ID NO 289
<211> LENGTH: 16
<212> TYPE: RNA
<213> ORGANISM: Homo sapiens

<400> SEQUENCE: 289
uaugcaagga gcuaaa                                                   16

<210> SEQ ID NO 290
<211> LENGTH: 16
<212> TYPE: RNA
<213> ORGANISM: Homo sapiens

<400> SEQUENCE: 290
augcaaggag cuaaac                                                   16

<210> SEQ ID NO 291
```

```
<211> LENGTH: 16
<212> TYPE: RNA
<213> ORGANISM: Homo sapiens

<400> SEQUENCE: 291
ugcaaggagc uaaaca                                                     16

<210> SEQ ID NO 292
<211> LENGTH: 16
<212> TYPE: RNA
<213> ORGANISM: Homo sapiens

<400> SEQUENCE: 292
guggauucug uguuau                                                     16

<210> SEQ ID NO 293
<211> LENGTH: 16
<212> TYPE: RNA
<213> ORGANISM: Homo sapiens

<400> SEQUENCE: 293
uggauucugu guuaug                                                     16

<210> SEQ ID NO 294
<211> LENGTH: 16
<212> TYPE: RNA
<213> ORGANISM: Homo sapiens

<400> SEQUENCE: 294
ggauucugug uuauga                                                     16

<210> SEQ ID NO 295
<211> LENGTH: 16
<212> TYPE: RNA
<213> ORGANISM: Homo sapiens

<400> SEQUENCE: 295
gauucugugu uaugau                                                     16

<210> SEQ ID NO 296
<211> LENGTH: 16
<212> TYPE: RNA
<213> ORGANISM: Homo sapiens

<400> SEQUENCE: 296
auucuguguu augauu                                                     16

<210> SEQ ID NO 297
<211> LENGTH: 16
<212> TYPE: RNA
<213> ORGANISM: Homo sapiens

<400> SEQUENCE: 297
uucuguguua ugauuu                                                     16

<210> SEQ ID NO 298
<211> LENGTH: 16
<212> TYPE: RNA
<213> ORGANISM: Homo sapiens

<400> SEQUENCE: 298
ucuguguuau gauuua                                                     16
```

```
<210> SEQ ID NO 299
<211> LENGTH: 16
<212> TYPE: RNA
<213> ORGANISM: Homo sapiens

<400> SEQUENCE: 299
cuguguuaug auuuac                                                   16

<210> SEQ ID NO 300
<211> LENGTH: 16
<212> TYPE: RNA
<213> ORGANISM: Homo sapiens

<400> SEQUENCE: 300
uguguuauga uuuaca                                                   16

<210> SEQ ID NO 301
<211> LENGTH: 16
<212> TYPE: RNA
<213> ORGANISM: Homo sapiens

<400> SEQUENCE: 301
guguuaugau uuacau                                                   16

<210> SEQ ID NO 302
<211> LENGTH: 16
<212> TYPE: RNA
<213> ORGANISM: Homo sapiens

<400> SEQUENCE: 302
uguuaugauu uacauu                                                   16

<210> SEQ ID NO 303
<211> LENGTH: 16
<212> TYPE: RNA
<213> ORGANISM: Homo sapiens

<400> SEQUENCE: 303
guuaugauuu acauuu                                                   16

<210> SEQ ID NO 304
<211> LENGTH: 16
<212> TYPE: RNA
<213> ORGANISM: Homo sapiens

<400> SEQUENCE: 304
uuaugauuua cauuuu                                                   16

<210> SEQ ID NO 305
<211> LENGTH: 16
<212> TYPE: RNA
<213> ORGANISM: Homo sapiens

<400> SEQUENCE: 305
uaugauuuac auuuuu                                                   16

<210> SEQ ID NO 306
<211> LENGTH: 16
<212> TYPE: RNA
<213> ORGANISM: Homo sapiens

<400> SEQUENCE: 306
augauuuaca uuuuuc                                                   16
```

<210> SEQ ID NO 307
<211> LENGTH: 16
<212> TYPE: RNA
<213> ORGANISM: Homo sapiens

<400> SEQUENCE: 307
ugauuuacau uuuucu                                                     16

<210> SEQ ID NO 308
<211> LENGTH: 16
<212> TYPE: RNA
<213> ORGANISM: Homo sapiens

<400> SEQUENCE: 308
ucaccuguca ugaaau                                                     16

<210> SEQ ID NO 309
<211> LENGTH: 16
<212> TYPE: RNA
<213> ORGANISM: Homo sapiens

<400> SEQUENCE: 309
caccugucau gaaaug                                                     16

<210> SEQ ID NO 310
<211> LENGTH: 16
<212> TYPE: RNA
<213> ORGANISM: Homo sapiens

<400> SEQUENCE: 310
accugucaug aaaugg                                                     16

<210> SEQ ID NO 311
<211> LENGTH: 16
<212> TYPE: RNA
<213> ORGANISM: Homo sapiens

<400> SEQUENCE: 311
ccugucauga aauggc                                                     16

<210> SEQ ID NO 312
<211> LENGTH: 16
<212> TYPE: RNA
<213> ORGANISM: Homo sapiens

<400> SEQUENCE: 312
cugucaugaa auggca                                                     16

<210> SEQ ID NO 313
<211> LENGTH: 16
<212> TYPE: RNA
<213> ORGANISM: Homo sapiens

<400> SEQUENCE: 313
ugucaugaaa uggcag                                                     16

<210> SEQ ID NO 314
<211> LENGTH: 16
<212> TYPE: RNA
<213> ORGANISM: Homo sapiens

<400> SEQUENCE: 314
gucaugaaau ggcagu                                                     16

```
<210> SEQ ID NO 315
<211> LENGTH: 16
<212> TYPE: RNA
<213> ORGANISM: Homo sapiens

<400> SEQUENCE: 315
ucaugaaaug gcagug                                                        16

<210> SEQ ID NO 316
<211> LENGTH: 16
<212> TYPE: RNA
<213> ORGANISM: Homo sapiens

<400> SEQUENCE: 316
caugaaaugg cagugg                                                        16

<210> SEQ ID NO 317
<211> LENGTH: 16
<212> TYPE: RNA
<213> ORGANISM: Homo sapiens

<400> SEQUENCE: 317
augaaauggc agugga                                                        16

<210> SEQ ID NO 318
<211> LENGTH: 16
<212> TYPE: RNA
<213> ORGANISM: Homo sapiens

<400> SEQUENCE: 318
ugaaauggca guggaa                                                        16

<210> SEQ ID NO 319
<211> LENGTH: 16
<212> TYPE: RNA
<213> ORGANISM: Homo sapiens

<400> SEQUENCE: 319
gaaauggcag uggaaa                                                        16

<210> SEQ ID NO 320
<211> LENGTH: 16
<212> TYPE: RNA
<213> ORGANISM: Homo sapiens

<400> SEQUENCE: 320
aaauggcagu ggaaag                                                        16

<210> SEQ ID NO 321
<211> LENGTH: 16
<212> TYPE: RNA
<213> ORGANISM: Homo sapiens

<400> SEQUENCE: 321
aauggcagug gaaaga                                                        16

<210> SEQ ID NO 322
<211> LENGTH: 16
<212> TYPE: RNA
<213> ORGANISM: Homo sapiens

<400> SEQUENCE: 322
```

```
auggcagugg aaagac                                                    16

<210> SEQ ID NO 323
<211> LENGTH: 16
<212> TYPE: RNA
<213> ORGANISM: Homo sapiens

<400> SEQUENCE: 323
uggcagugga aagacu                                                    16

<210> SEQ ID NO 324
<211> LENGTH: 16
<212> TYPE: RNA
<213> ORGANISM: Homo sapiens

<400> SEQUENCE: 324
ugcauucacc ugucau                                                    16

<210> SEQ ID NO 325
<211> LENGTH: 16
<212> TYPE: RNA
<213> ORGANISM: Homo sapiens

<400> SEQUENCE: 325
gcauucaccu gucaug                                                    16

<210> SEQ ID NO 326
<211> LENGTH: 16
<212> TYPE: RNA
<213> ORGANISM: Homo sapiens

<400> SEQUENCE: 326
cauucaccug ucauga                                                    16

<210> SEQ ID NO 327
<211> LENGTH: 16
<212> TYPE: RNA
<213> ORGANISM: Homo sapiens

<400> SEQUENCE: 327
auucaccugu caugaa                                                    16

<210> SEQ ID NO 328
<211> LENGTH: 16
<212> TYPE: RNA
<213> ORGANISM: Homo sapiens

<400> SEQUENCE: 328
uucaccuguc augaaa                                                    16

<210> SEQ ID NO 329
<211> LENGTH: 16
<212> TYPE: RNA
<213> ORGANISM: Homo sapiens

<400> SEQUENCE: 329
cuccucuaag gugaau                                                    16

<210> SEQ ID NO 330
<211> LENGTH: 16
<212> TYPE: RNA
<213> ORGANISM: Homo sapiens

<400> SEQUENCE: 330
```

| | |
|---|---|
| uccucuaagg ugaaug | 16 |

<210> SEQ ID NO 331
<211> LENGTH: 16
<212> TYPE: RNA
<213> ORGANISM: Homo sapiens

<400> SEQUENCE: 331

| | |
|---|---|
| ccucuaaggu gaaugc | 16 |

<210> SEQ ID NO 332
<211> LENGTH: 16
<212> TYPE: RNA
<213> ORGANISM: Homo sapiens

<400> SEQUENCE: 332

| | |
|---|---|
| cucuaaggug aaugca | 16 |

<210> SEQ ID NO 333
<211> LENGTH: 16
<212> TYPE: RNA
<213> ORGANISM: Homo sapiens

<400> SEQUENCE: 333

| | |
|---|---|
| ucuaagguga augcau | 16 |

<210> SEQ ID NO 334
<211> LENGTH: 16
<212> TYPE: RNA
<213> ORGANISM: Homo sapiens

<400> SEQUENCE: 334

| | |
|---|---|
| cuaaggugaa ugcauu | 16 |

<210> SEQ ID NO 335
<211> LENGTH: 16
<212> TYPE: RNA
<213> ORGANISM: Homo sapiens

<400> SEQUENCE: 335

| | |
|---|---|
| uaaggugaau gcauuu | 16 |

<210> SEQ ID NO 336
<211> LENGTH: 16
<212> TYPE: RNA
<213> ORGANISM: Homo sapiens

<400> SEQUENCE: 336

| | |
|---|---|
| aaggugaaug cauuuu | 16 |

<210> SEQ ID NO 337
<211> LENGTH: 16
<212> TYPE: RNA
<213> ORGANISM: Homo sapiens

<400> SEQUENCE: 337

| | |
|---|---|
| aggugaaugc auuuc | 16 |

<210> SEQ ID NO 338
<211> LENGTH: 16
<212> TYPE: RNA
<213> ORGANISM: Homo sapiens

```
<400> SEQUENCE: 338
ggugaaugca uuuucu                                                    16

<210> SEQ ID NO 339
<211> LENGTH: 16
<212> TYPE: RNA
<213> ORGANISM: Homo sapiens

<400> SEQUENCE: 339
gugaaugcau uuucuu                                                    16

<210> SEQ ID NO 340
<211> LENGTH: 16
<212> TYPE: RNA
<213> ORGANISM: Homo sapiens

<400> SEQUENCE: 340
ugaaugcauu uucuug                                                    16

<210> SEQ ID NO 341
<211> LENGTH: 16
<212> TYPE: RNA
<213> ORGANISM: Homo sapiens

<400> SEQUENCE: 341
gaaugcauuu ucuugc                                                    16

<210> SEQ ID NO 342
<211> LENGTH: 16
<212> TYPE: RNA
<213> ORGANISM: Homo sapiens

<400> SEQUENCE: 342
aaugcauuuu cuugca                                                    16

<210> SEQ ID NO 343
<211> LENGTH: 16
<212> TYPE: RNA
<213> ORGANISM: Homo sapiens

<400> SEQUENCE: 343
augcauuuuc uugcau                                                    16

<210> SEQ ID NO 344
<211> LENGTH: 16
<212> TYPE: RNA
<213> ORGANISM: Homo sapiens

<400> SEQUENCE: 344
ugcauuuucu ugcauu                                                    16

<210> SEQ ID NO 345
<211> LENGTH: 16
<212> TYPE: RNA
<213> ORGANISM: Homo sapiens

<400> SEQUENCE: 345
ccacauccac cagaau                                                    16

<210> SEQ ID NO 346
<211> LENGTH: 16
<212> TYPE: RNA
<213> ORGANISM: Homo sapiens
```

```
<400> SEQUENCE: 346
cacauccacc agaaug                                              16

<210> SEQ ID NO 347
<211> LENGTH: 16
<212> TYPE: RNA
<213> ORGANISM: Homo sapiens

<400> SEQUENCE: 347
acauccacca gaaugg                                              16

<210> SEQ ID NO 348
<211> LENGTH: 16
<212> TYPE: RNA
<213> ORGANISM: Homo sapiens

<400> SEQUENCE: 348
cauccaccag aauggc                                              16

<210> SEQ ID NO 349
<211> LENGTH: 16
<212> TYPE: RNA
<213> ORGANISM: Homo sapiens

<400> SEQUENCE: 349
auccaccaga auggcu                                              16

<210> SEQ ID NO 350
<211> LENGTH: 16
<212> TYPE: RNA
<213> ORGANISM: Homo sapiens

<400> SEQUENCE: 350
uccaccagaa uggcua                                              16

<210> SEQ ID NO 351
<211> LENGTH: 16
<212> TYPE: RNA
<213> ORGANISM: Homo sapiens

<400> SEQUENCE: 351
ccaccagaau ggcuac                                              16

<210> SEQ ID NO 352
<211> LENGTH: 16
<212> TYPE: RNA
<213> ORGANISM: Homo sapiens

<400> SEQUENCE: 352
caccagaaug gcuaca                                              16

<210> SEQ ID NO 353
<211> LENGTH: 16
<212> TYPE: RNA
<213> ORGANISM: Homo sapiens

<400> SEQUENCE: 353
accagaaugg cuacaa                                              16

<210> SEQ ID NO 354
<211> LENGTH: 16
<212> TYPE: RNA
```

```
<213> ORGANISM: Homo sapiens

<400> SEQUENCE: 354
ccagaauggc uacaac                                                     16

<210> SEQ ID NO 355
<211> LENGTH: 16
<212> TYPE: RNA
<213> ORGANISM: Homo sapiens

<400> SEQUENCE: 355
cagaauggcu acaacu                                                     16

<210> SEQ ID NO 356
<211> LENGTH: 16
<212> TYPE: RNA
<213> ORGANISM: Homo sapiens

<400> SEQUENCE: 356
agaauggcua caacuu                                                     16

<210> SEQ ID NO 357
<211> LENGTH: 16
<212> TYPE: RNA
<213> ORGANISM: Homo sapiens

<400> SEQUENCE: 357
gaauggcuac aacuua                                                     16

<210> SEQ ID NO 358
<211> LENGTH: 16
<212> TYPE: RNA
<213> ORGANISM: Homo sapiens

<400> SEQUENCE: 358
aauggcuaca acuuaa                                                     16

<210> SEQ ID NO 359
<211> LENGTH: 16
<212> TYPE: RNA
<213> ORGANISM: Homo sapiens

<400> SEQUENCE: 359
auggcuacaa cuuaaa                                                     16

<210> SEQ ID NO 360
<211> LENGTH: 16
<212> TYPE: RNA
<213> ORGANISM: Homo sapiens

<400> SEQUENCE: 360
uggcuacaac uuaaaa                                                     16

<210> SEQ ID NO 361
<211> LENGTH: 16
<212> TYPE: RNA
<213> ORGANISM: Homo sapiens

<400> SEQUENCE: 361
uuuuuuaaag caugau                                                     16

<210> SEQ ID NO 362
<211> LENGTH: 16
```

```
<212> TYPE: RNA
<213> ORGANISM: Homo sapiens

<400> SEQUENCE: 362
uuuuuaaagc augaug                                                    16

<210> SEQ ID NO 363
<211> LENGTH: 16
<212> TYPE: RNA
<213> ORGANISM: Homo sapiens

<400> SEQUENCE: 363
uuuuaaagca ugaugg                                                    16

<210> SEQ ID NO 364
<211> LENGTH: 16
<212> TYPE: RNA
<213> ORGANISM: Homo sapiens

<400> SEQUENCE: 364
uuuaaagcau gaugga                                                    16

<210> SEQ ID NO 365
<211> LENGTH: 16
<212> TYPE: RNA
<213> ORGANISM: Homo sapiens

<400> SEQUENCE: 365
uuaaagcaug auggaa                                                    16

<210> SEQ ID NO 366
<211> LENGTH: 16
<212> TYPE: RNA
<213> ORGANISM: Homo sapiens

<400> SEQUENCE: 366
uaaagcauga uggaau                                                    16

<210> SEQ ID NO 367
<211> LENGTH: 16
<212> TYPE: RNA
<213> ORGANISM: Homo sapiens

<400> SEQUENCE: 367
aaagcaugau ggaauu                                                    16

<210> SEQ ID NO 368
<211> LENGTH: 16
<212> TYPE: RNA
<213> ORGANISM: Homo sapiens

<400> SEQUENCE: 368
aagcaugaug gaauuu                                                    16

<210> SEQ ID NO 369
<211> LENGTH: 16
<212> TYPE: RNA
<213> ORGANISM: Homo sapiens

<400> SEQUENCE: 369
agcaugaugg aauuuu                                                    16

<210> SEQ ID NO 370
```

```
<211> LENGTH: 16
<212> TYPE: RNA
<213> ORGANISM: Homo sapiens

<400> SEQUENCE: 370
gcaugaugga auuuua                                                    16

<210> SEQ ID NO 371
<211> LENGTH: 16
<212> TYPE: RNA
<213> ORGANISM: Homo sapiens

<400> SEQUENCE: 371
caugauggaa uuuuag                                                    16

<210> SEQ ID NO 372
<211> LENGTH: 16
<212> TYPE: RNA
<213> ORGANISM: Homo sapiens

<400> SEQUENCE: 372
augauggaau uuuagc                                                    16

<210> SEQ ID NO 373
<211> LENGTH: 16
<212> TYPE: RNA
<213> ORGANISM: Homo sapiens

<400> SEQUENCE: 373
ugauggaauu uuagcu                                                    16

<210> SEQ ID NO 374
<211> LENGTH: 16
<212> TYPE: RNA
<213> ORGANISM: Homo sapiens

<400> SEQUENCE: 374
gauggaauuu uagcug                                                    16

<210> SEQ ID NO 375
<211> LENGTH: 16
<212> TYPE: RNA
<213> ORGANISM: Homo sapiens

<400> SEQUENCE: 375
auggaauuuu agcugc                                                    16

<210> SEQ ID NO 376
<211> LENGTH: 16
<212> TYPE: RNA
<213> ORGANISM: Homo sapiens

<400> SEQUENCE: 376
uggaauuuua gcugca                                                    16

<210> SEQ ID NO 377
<211> LENGTH: 16
<212> TYPE: RNA
<213> ORGANISM: Homo sapiens

<400> SEQUENCE: 377 uuuuuuuua aagcau                                                     16
```

```
<210> SEQ ID NO 378
<211> LENGTH: 16
<212> TYPE: RNA
<213> ORGANISM: Homo sapiens

<400> SEQUENCE: 378
uuuuuuuuaa agcaug                                                       16

<210> SEQ ID NO 379
<211> LENGTH: 16
<212> TYPE: RNA
<213> ORGANISM: Homo sapiens

<400> SEQUENCE: 379
uuuuuuuaaa gcauga                                                       16

<210> SEQ ID NO 380
<211> LENGTH: 16
<212> TYPE: RNA
<213> ORGANISM: Homo sapiens

<400> SEQUENCE: 380
uuuuuuaaag caugau                                                       16

<210> SEQ ID NO 381
<211> LENGTH: 16
<212> TYPE: RNA
<213> ORGANISM: Homo sapiens

<400> SEQUENCE: 381
guucugcugg acuaau                                                       16

<210> SEQ ID NO 382
<211> LENGTH: 16
<212> TYPE: RNA
<213> ORGANISM: Homo sapiens

<400> SEQUENCE: 382
uucugcugga cuaaug                                                       16

<210> SEQ ID NO 383
<211> LENGTH: 16
<212> TYPE: RNA
<213> ORGANISM: Homo sapiens

<400> SEQUENCE: 383
ucugcuggac uaauga                                                       16

<210> SEQ ID NO 384
<211> LENGTH: 16
<212> TYPE: RNA
<213> ORGANISM: Homo sapiens

<400> SEQUENCE: 384
cugcuggacu aaugaa                                                       16

<210> SEQ ID NO 385
<211> LENGTH: 16
<212> TYPE: RNA
<213> ORGANISM: Homo sapiens

<400> SEQUENCE: 385
ugcuggacua augaag                                                       16
```

```
<210> SEQ ID NO 386
<211> LENGTH: 16
<212> TYPE: RNA
<213> ORGANISM: Homo sapiens

<400> SEQUENCE: 386
gcuggacuaa ugaagu                                                   16

<210> SEQ ID NO 387
<211> LENGTH: 16
<212> TYPE: RNA
<213> ORGANISM: Homo sapiens

<400> SEQUENCE: 387
cuggacuaau gaagug                                                   16

<210> SEQ ID NO 388
<211> LENGTH: 16
<212> TYPE: RNA
<213> ORGANISM: Homo sapiens

<400> SEQUENCE: 388
uggacuaaug aagugc                                                   16

<210> SEQ ID NO 389
<211> LENGTH: 16
<212> TYPE: RNA
<213> ORGANISM: Homo sapiens

<400> SEQUENCE: 389
ggacuaauga agugcc                                                   16

<210> SEQ ID NO 390
<211> LENGTH: 16
<212> TYPE: RNA
<213> ORGANISM: Homo sapiens

<400> SEQUENCE: 390
gacuaaugaa gugcca                                                   16

<210> SEQ ID NO 391
<211> LENGTH: 16
<212> TYPE: RNA
<213> ORGANISM: Homo sapiens

<400> SEQUENCE: 391
acuaaugaag ugccac                                                   16

<210> SEQ ID NO 392
<211> LENGTH: 16
<212> TYPE: RNA
<213> ORGANISM: Homo sapiens

<400> SEQUENCE: 392
cuaaugaagu gccacu                                                   16

<210> SEQ ID NO 393
<211> LENGTH: 16
<212> TYPE: RNA
<213> ORGANISM: Homo sapiens

<400> SEQUENCE: 393
uaaugaagug ccacuc                                                   16
```

```
<210> SEQ ID NO 394
<211> LENGTH: 16
<212> TYPE: RNA
<213> ORGANISM: Homo sapiens

<400> SEQUENCE: 394
aaugaagugc cacucc                                                    16

<210> SEQ ID NO 395
<211> LENGTH: 16
<212> TYPE: RNA
<213> ORGANISM: Homo sapiens

<400> SEQUENCE: 395
augaagugcc acucca                                                    16

<210> SEQ ID NO 396
<211> LENGTH: 16
<212> TYPE: RNA
<213> ORGANISM: Homo sapiens

<400> SEQUENCE: 396
ugaagugcca cuccac                                                    16

<210> SEQ ID NO 397
<211> LENGTH: 16
<212> TYPE: RNA
<213> ORGANISM: Homo sapiens

<400> SEQUENCE: 397
ugaggauaga gcacau                                                    16

<210> SEQ ID NO 398
<211> LENGTH: 16
<212> TYPE: RNA
<213> ORGANISM: Homo sapiens

<400> SEQUENCE: 398
gaggauagag cacaug                                                    16

<210> SEQ ID NO 399
<211> LENGTH: 16
<212> TYPE: RNA
<213> ORGANISM: Homo sapiens

<400> SEQUENCE: 399
aggauagagc acaugu                                                    16

<210> SEQ ID NO 400
<211> LENGTH: 16
<212> TYPE: RNA
<213> ORGANISM: Homo sapiens

<400> SEQUENCE: 400
ggauagagca caugug                                                    16

<210> SEQ ID NO 401
<211> LENGTH: 16
<212> TYPE: RNA
<213> ORGANISM: Homo sapiens

<400> SEQUENCE: 401
```

-continued gauagagcac auguga 16

<210> SEQ ID NO 402
<211> LENGTH: 16
<212> TYPE: RNA
<213> ORGANISM: Homo sapiens

<400> SEQUENCE: 402
auagagcaca ugugag 16

<210> SEQ ID NO 403
<211> LENGTH: 16
<212> TYPE: RNA
<213> ORGANISM: Homo sapiens

<400> SEQUENCE: 403
uagagcacau gugaga 16

<210> SEQ ID NO 404
<211> LENGTH: 16
<212> TYPE: RNA
<213> ORGANISM: Homo sapiens

<400> SEQUENCE: 404
agagcacaug ugagau 16

<210> SEQ ID NO 405
<211> LENGTH: 16
<212> TYPE: RNA
<213> ORGANISM: Homo sapiens

<400> SEQUENCE: 405
gagcacaugu gagauu 16

<210> SEQ ID NO 406
<211> LENGTH: 16
<212> TYPE: RNA
<213> ORGANISM: Homo sapiens

<400> SEQUENCE: 406
agcacaugug agauuu 16

<210> SEQ ID NO 407
<211> LENGTH: 16
<212> TYPE: RNA
<213> ORGANISM: Homo sapiens

<400> SEQUENCE: 407
gcacauguga gauuuu 16

<210> SEQ ID NO 408
<211> LENGTH: 16
<212> TYPE: RNA
<213> ORGANISM: Homo sapiens

<400> SEQUENCE: 408
cacaugugag auuuua 16

<210> SEQ ID NO 409
<211> LENGTH: 16
<212> TYPE: RNA
<213> ORGANISM: Homo sapiens

<400> SEQUENCE: 409

-continued acaugugaga uuuuac                                          16

<210> SEQ ID NO 410
<211> LENGTH: 16
<212> TYPE: RNA
<213> ORGANISM: Homo sapiens

<400> SEQUENCE: 410
caugugagau uuuacu                                          16

<210> SEQ ID NO 411
<211> LENGTH: 16
<212> TYPE: RNA
<213> ORGANISM: Homo sapiens

<400> SEQUENCE: 411
augugagauu uuacuu                                          16

<210> SEQ ID NO 412
<211> LENGTH: 16
<212> TYPE: RNA
<213> ORGANISM: Homo sapiens

<400> SEQUENCE: 412
ugugagauuu uacuuu                                          16

<210> SEQ ID NO 413
<211> LENGTH: 16
<212> TYPE: RNA
<213> ORGANISM: Homo sapiens

<400> SEQUENCE: 413
uuuuuucuuc uuuaau                                          16

<210> SEQ ID NO 414
<211> LENGTH: 16
<212> TYPE: RNA
<213> ORGANISM: Homo sapiens

<400> SEQUENCE: 414
uuuuucuucu uuaaug                                          16

<210> SEQ ID NO 415
<211> LENGTH: 16
<212> TYPE: RNA
<213> ORGANISM: Homo sapiens

<400> SEQUENCE: 415
uuuucuucuu uaauga                                          16

<210> SEQ ID NO 416
<211> LENGTH: 16
<212> TYPE: RNA
<213> ORGANISM: Homo sapiens

<400> SEQUENCE: 416
uuucuucuuu aaugag                                          16

<210> SEQ ID NO 417
<211> LENGTH: 16
<212> TYPE: RNA
<213> ORGANISM: Homo sapiens

```
<400> SEQUENCE: 417
uucuucuuua augagg                                           16

<210> SEQ ID NO 418
<211> LENGTH: 16
<212> TYPE: RNA
<213> ORGANISM: Homo sapiens

<400> SEQUENCE: 418
ucuucuuuaa ugagga                                           16

<210> SEQ ID NO 419
<211> LENGTH: 16
<212> TYPE: RNA
<213> ORGANISM: Homo sapiens

<400> SEQUENCE: 419
cuucuuuaau gaggau                                           16

<210> SEQ ID NO 420
<211> LENGTH: 16
<212> TYPE: RNA
<213> ORGANISM: Homo sapiens

<400> SEQUENCE: 420
uucuuuaaug aggaua                                           16

<210> SEQ ID NO 421
<211> LENGTH: 16
<212> TYPE: RNA
<213> ORGANISM: Homo sapiens

<400> SEQUENCE: 421
ucuuuaauga ggauag                                           16

<210> SEQ ID NO 422
<211> LENGTH: 16
<212> TYPE: RNA
<213> ORGANISM: Homo sapiens

<400> SEQUENCE: 422
cuuuaaugag gauaga                                           16

<210> SEQ ID NO 423
<211> LENGTH: 16
<212> TYPE: RNA
<213> ORGANISM: Homo sapiens

<400> SEQUENCE: 423
uuuaaugagg auagag                                           16

<210> SEQ ID NO 424
<211> LENGTH: 16
<212> TYPE: RNA
<213> ORGANISM: Homo sapiens

<400> SEQUENCE: 424
uuaaugagga uagagc                                           16

<210> SEQ ID NO 425
<211> LENGTH: 16
<212> TYPE: RNA
<213> ORGANISM: Homo sapiens
```

```
<400> SEQUENCE: 425
uaaugaggau agagca                                                          16

<210> SEQ ID NO 426
<211> LENGTH: 16
<212> TYPE: RNA
<213> ORGANISM: Homo sapiens

<400> SEQUENCE: 426
aaugaggaua gagcac                                                          16

<210> SEQ ID NO 427
<211> LENGTH: 16
<212> TYPE: RNA
<213> ORGANISM: Homo sapiens

<400> SEQUENCE: 427
augaggauag agcaca                                                          16

<210> SEQ ID NO 428
<211> LENGTH: 16
<212> TYPE: RNA
<213> ORGANISM: Homo sapiens

<400> SEQUENCE: 428
gcaaaggagg gaggau                                                          16

<210> SEQ ID NO 429
<211> LENGTH: 16
<212> TYPE: RNA
<213> ORGANISM: Homo sapiens

<400> SEQUENCE: 429
caaaggaggg aggaug                                                          16

<210> SEQ ID NO 430
<211> LENGTH: 16
<212> TYPE: RNA
<213> ORGANISM: Homo sapiens

<400> SEQUENCE: 430
aaaggaggga ggaugc                                                          16

<210> SEQ ID NO 431
<211> LENGTH: 16
<212> TYPE: RNA
<213> ORGANISM: Homo sapiens

<400> SEQUENCE: 431
aaggagggag gaugcu                                                          16

<210> SEQ ID NO 432
<211> LENGTH: 16
<212> TYPE: RNA
<213> ORGANISM: Homo sapiens

<400> SEQUENCE: 432
aggagggagg augcug                                                          16

<210> SEQ ID NO 433
<211> LENGTH: 16
<212> TYPE: RNA
```

```
<213> ORGANISM: Homo sapiens

<400> SEQUENCE: 433
ggagggagga ugcugu                                                    16

<210> SEQ ID NO 434
<211> LENGTH: 16
<212> TYPE: RNA
<213> ORGANISM: Homo sapiens

<400> SEQUENCE: 434
gagggaggau gcugug                                                    16

<210> SEQ ID NO 435
<211> LENGTH: 16
<212> TYPE: RNA
<213> ORGANISM: Homo sapiens

<400> SEQUENCE: 435
agggaggaug cugugg                                                    16

<210> SEQ ID NO 436
<211> LENGTH: 16
<212> TYPE: RNA
<213> ORGANISM: Homo sapiens

<400> SEQUENCE: 436
gggaggaugc uguggu                                                    16

<210> SEQ ID NO 437
<211> LENGTH: 16
<212> TYPE: RNA
<213> ORGANISM: Homo sapiens

<400> SEQUENCE: 437
ggaggaugcu gugguc                                                    16

<210> SEQ ID NO 438
<211> LENGTH: 16
<212> TYPE: RNA
<213> ORGANISM: Homo sapiens

<400> SEQUENCE: 438
gaggaugcug ugguca                                                    16

<210> SEQ ID NO 439
<211> LENGTH: 16
<212> TYPE: RNA
<213> ORGANISM: Homo sapiens

<400> SEQUENCE: 439
aggaugcugu ggucau                                                    16

<210> SEQ ID NO 440
<211> LENGTH: 16
<212> TYPE: RNA
<213> ORGANISM: Homo sapiens

<400> SEQUENCE: 440
ggaugcugug gucauc                                                    16

<210> SEQ ID NO 441
<211> LENGTH: 16
```

```
<212> TYPE: RNA
<213> ORGANISM: Homo sapiens

<400> SEQUENCE: 441
gaugcugugg ucaucc                                               16

<210> SEQ ID NO 442
<211> LENGTH: 16
<212> TYPE: RNA
<213> ORGANISM: Homo sapiens

<400> SEQUENCE: 442
augcuguggu cauccu                                               16

<210> SEQ ID NO 443
<211> LENGTH: 16
<212> TYPE: RNA
<213> ORGANISM: Homo sapiens

<400> SEQUENCE: 443
ugcugugguc auccuu                                               16

<210> SEQ ID NO 444
<211> LENGTH: 16
<212> TYPE: RNA
<213> ORGANISM: Homo sapiens

<400> SEQUENCE: 444
ucccuguaca ggaaau                                               16

<210> SEQ ID NO 445
<211> LENGTH: 16
<212> TYPE: RNA
<213> ORGANISM: Homo sapiens

<400> SEQUENCE: 445
cccuguacag gaaaug                                               16

<210> SEQ ID NO 446
<211> LENGTH: 16
<212> TYPE: RNA
<213> ORGANISM: Homo sapiens

<400> SEQUENCE: 446
ccuguacagg aaaugc                                               16

<210> SEQ ID NO 447
<211> LENGTH: 16
<212> TYPE: RNA
<213> ORGANISM: Homo sapiens

<400> SEQUENCE: 447
cuguacagga aaugcc                                               16

<210> SEQ ID NO 448
<211> LENGTH: 16
<212> TYPE: RNA
<213> ORGANISM: Homo sapiens

<400> SEQUENCE: 448
uguacaggaa augccu                                               16

<210> SEQ ID NO 449
```

```
<211> LENGTH: 16
<212> TYPE: RNA
<213> ORGANISM: Homo sapiens

<400> SEQUENCE: 449
guacaggaaa ugccuc                                                  16

<210> SEQ ID NO 450
<211> LENGTH: 16
<212> TYPE: RNA
<213> ORGANISM: Homo sapiens

<400> SEQUENCE: 450
uacaggaaau gccucu                                                  16

<210> SEQ ID NO 451
<211> LENGTH: 16
<212> TYPE: RNA
<213> ORGANISM: Homo sapiens

<400> SEQUENCE: 451
acaggaaaug ccucuu                                                  16

<210> SEQ ID NO 452
<211> LENGTH: 16
<212> TYPE: RNA
<213> ORGANISM: Homo sapiens

<400> SEQUENCE: 452
caggaaaugc cucuuc                                                  16

<210> SEQ ID NO 453
<211> LENGTH: 16
<212> TYPE: RNA
<213> ORGANISM: Homo sapiens

<400> SEQUENCE: 453
aggaaaugcc ucuucu                                                  16

<210> SEQ ID NO 454
<211> LENGTH: 16
<212> TYPE: RNA
<213> ORGANISM: Homo sapiens

<400> SEQUENCE: 454
ggaaaugccu cuucuu                                                  16

<210> SEQ ID NO 455
<211> LENGTH: 16
<212> TYPE: RNA
<213> ORGANISM: Homo sapiens

<400> SEQUENCE: 455
gaaaugccuc uucuua                                                  16

<210> SEQ ID NO 456
<211> LENGTH: 16
<212> TYPE: RNA
<213> ORGANISM: Homo sapiens

<400> SEQUENCE: 456
aaaugccucu ucuuac                                                  16
```

```
<210> SEQ ID NO 457
<211> LENGTH: 16
<212> TYPE: RNA
<213> ORGANISM: Homo sapiens

<400> SEQUENCE: 457
aaugccucuu cuuacu                                                   16

<210> SEQ ID NO 458
<211> LENGTH: 16
<212> TYPE: RNA
<213> ORGANISM: Homo sapiens

<400> SEQUENCE: 458
augccucuuc uuacuu                                                   16

<210> SEQ ID NO 459
<211> LENGTH: 16
<212> TYPE: RNA
<213> ORGANISM: Homo sapiens

<400> SEQUENCE: 459
ugccucuucu uacuuc                                                   16

<210> SEQ ID NO 460
<211> LENGTH: 16
<212> TYPE: RNA
<213> ORGANISM: Homo sapiens

<400> SEQUENCE: 460
uuggguacca ucgaau                                                   16

<210> SEQ ID NO 461
<211> LENGTH: 16
<212> TYPE: RNA
<213> ORGANISM: Homo sapiens

<400> SEQUENCE: 461
uggguaccau cgaaug                                                   16

<210> SEQ ID NO 462
<211> LENGTH: 16
<212> TYPE: RNA
<213> ORGANISM: Homo sapiens

<400> SEQUENCE: 462
ggguaccauc gaauga                                                   16

<210> SEQ ID NO 463
<211> LENGTH: 16
<212> TYPE: RNA
<213> ORGANISM: Homo sapiens

<400> SEQUENCE: 463
gguaccaucg aaugac                                                   16

<210> SEQ ID NO 464
<211> LENGTH: 16
<212> TYPE: RNA
<213> ORGANISM: Homo sapiens

<400> SEQUENCE: 464
guaccaucga augacu                                                   16
```

-continued

```
<210> SEQ ID NO 465
<211> LENGTH: 16
<212> TYPE: RNA
<213> ORGANISM: Homo sapiens

<400> SEQUENCE: 465
uaccaucgaa ugacug                                                   16

<210> SEQ ID NO 466
<211> LENGTH: 16
<212> TYPE: RNA
<213> ORGANISM: Homo sapiens

<400> SEQUENCE: 466
accaucgaau gacugu                                                   16

<210> SEQ ID NO 467
<211> LENGTH: 16
<212> TYPE: RNA
<213> ORGANISM: Homo sapiens

<400> SEQUENCE: 467
ccaucgaaug acuguc                                                   16

<210> SEQ ID NO 468
<211> LENGTH: 16
<212> TYPE: RNA
<213> ORGANISM: Homo sapiens

<400> SEQUENCE: 468
caucgaauga cuguca                                                   16

<210> SEQ ID NO 469
<211> LENGTH: 16
<212> TYPE: RNA
<213> ORGANISM: Homo sapiens

<400> SEQUENCE: 469
aucgaaugac ugucag                                                   16

<210> SEQ ID NO 470
<211> LENGTH: 16
<212> TYPE: RNA
<213> ORGANISM: Homo sapiens

<400> SEQUENCE: 470
ucgaaugacu gucaga                                                   16

<210> SEQ ID NO 471
<211> LENGTH: 16
<212> TYPE: RNA
<213> ORGANISM: Homo sapiens

<400> SEQUENCE: 471
cgaaugacug ucagaa                                                   16

<210> SEQ ID NO 472
<211> LENGTH: 16
<212> TYPE: RNA
<213> ORGANISM: Homo sapiens

<400> SEQUENCE: 472
gaaugacugu cagaac                                                   16
```

<210> SEQ ID NO 473
<211> LENGTH: 16
<212> TYPE: RNA
<213> ORGANISM: Homo sapiens

<400> SEQUENCE: 473
aaugacuguc agaaca                                                   16

<210> SEQ ID NO 474
<211> LENGTH: 16
<212> TYPE: RNA
<213> ORGANISM: Homo sapiens

<400> SEQUENCE: 474
augacuguca gaacag                                                   16

<210> SEQ ID NO 475
<211> LENGTH: 16
<212> TYPE: RNA
<213> ORGANISM: Homo sapiens

<400> SEQUENCE: 475
ugacugucag aacaga                                                   16

<210> SEQ ID NO 476
<211> LENGTH: 16
<212> TYPE: RNA
<213> ORGANISM: Homo sapiens

<400> SEQUENCE: 476
ugguaguuac aauaau                                                   16

<210> SEQ ID NO 477
<211> LENGTH: 16
<212> TYPE: RNA
<213> ORGANISM: Homo sapiens

<400> SEQUENCE: 477
gguaguuaca auaaug                                                   16

<210> SEQ ID NO 478
<211> LENGTH: 16
<212> TYPE: RNA
<213> ORGANISM: Homo sapiens

<400> SEQUENCE: 478
guaguuacaa uaaugc                                                   16

<210> SEQ ID NO 479
<211> LENGTH: 16
<212> TYPE: RNA
<213> ORGANISM: Homo sapiens

<400> SEQUENCE: 479
uaguuacaau aaugcc                                                   16

<210> SEQ ID NO 480
<211> LENGTH: 16
<212> TYPE: RNA
<213> ORGANISM: Homo sapiens

<400> SEQUENCE: 480
aguuacaaua augcca                                          16

<210> SEQ ID NO 481
<211> LENGTH: 16
<212> TYPE: RNA
<213> ORGANISM: Homo sapiens

<400> SEQUENCE: 481
guuacaauaa ugccau                                          16

<210> SEQ ID NO 482
<211> LENGTH: 16
<212> TYPE: RNA
<213> ORGANISM: Homo sapiens

<400> SEQUENCE: 482
uuacaauaau gccauu                                          16

<210> SEQ ID NO 483
<211> LENGTH: 16
<212> TYPE: RNA
<213> ORGANISM: Homo sapiens

<400> SEQUENCE: 483
uacaauaaug ccauuu                                          16

<210> SEQ ID NO 484
<211> LENGTH: 16
<212> TYPE: RNA
<213> ORGANISM: Homo sapiens

<400> SEQUENCE: 484
acaauaaugc cauuuu                                          16

<210> SEQ ID NO 485
<211> LENGTH: 16
<212> TYPE: RNA
<213> ORGANISM: Homo sapiens

<400> SEQUENCE: 485
caauaaugcc auuuug                                          16

<210> SEQ ID NO 486
<211> LENGTH: 16
<212> TYPE: RNA
<213> ORGANISM: Homo sapiens

<400> SEQUENCE: 486
aauaaugcca uuuugu                                          16

<210> SEQ ID NO 487
<211> LENGTH: 16
<212> TYPE: RNA
<213> ORGANISM: Homo sapiens

<400> SEQUENCE: 487
auaaugccau uuugua                                          16

<210> SEQ ID NO 488
<211> LENGTH: 16
<212> TYPE: RNA
<213> ORGANISM: Homo sapiens

<400> SEQUENCE: 488
uaaugccauu uuguag 16

<210> SEQ ID NO 489
<211> LENGTH: 16
<212> TYPE: RNA
<213> ORGANISM: Homo sapiens

<400> SEQUENCE: 489
aaugccauuu uguagu 16

<210> SEQ ID NO 490
<211> LENGTH: 16
<212> TYPE: RNA
<213> ORGANISM: Homo sapiens

<400> SEQUENCE: 490
augccauuuu guaguc 16

<210> SEQ ID NO 491
<211> LENGTH: 16
<212> TYPE: RNA
<213> ORGANISM: Homo sapiens

<400> SEQUENCE: 491
ugccauuuug uagucc 16

<210> SEQ ID NO 492
<211> LENGTH: 16
<212> TYPE: RNA
<213> ORGANISM: Homo sapiens

<400> SEQUENCE: 492
augcuguuuu cuaaca 16

<210> SEQ ID NO 493
<211> LENGTH: 16
<212> TYPE: RNA
<213> ORGANISM: Homo sapiens

<400> SEQUENCE: 493
ugcuguuuuc uaacag 16

<210> SEQ ID NO 494
<211> LENGTH: 16
<212> TYPE: RNA
<213> ORGANISM: Homo sapiens

<400> SEQUENCE: 494
gcugcuucag acauau 16

<210> SEQ ID NO 495
<211> LENGTH: 16
<212> TYPE: RNA
<213> ORGANISM: Homo sapiens

<400> SEQUENCE: 495
cugcuucaga cauaug 16

<210> SEQ ID NO 496
<211> LENGTH: 16
<212> TYPE: RNA
<213> ORGANISM: Homo sapiens

```
<400> SEQUENCE: 496
ugcuucagac auaugu                                                    16

<210> SEQ ID NO 497
<211> LENGTH: 16
<212> TYPE: RNA
<213> ORGANISM: Homo sapiens

<400> SEQUENCE: 497
gcuucagaca uauguc                                                    16

<210> SEQ ID NO 498
<211> LENGTH: 16
<212> TYPE: RNA
<213> ORGANISM: Homo sapiens

<400> SEQUENCE: 498
cuucagacau augucu                                                    16

<210> SEQ ID NO 499
<211> LENGTH: 16
<212> TYPE: RNA
<213> ORGANISM: Homo sapiens

<400> SEQUENCE: 499
uucagacaua ugucug                                                    16

<210> SEQ ID NO 500
<211> LENGTH: 16
<212> TYPE: RNA
<213> ORGANISM: Homo sapiens

<400> SEQUENCE: 500
ucagacauau gucugu                                                    16

<210> SEQ ID NO 501
<211> LENGTH: 16
<212> TYPE: RNA
<213> ORGANISM: Homo sapiens

<400> SEQUENCE: 501
cagacauaug ucugug                                                    16

<210> SEQ ID NO 502
<211> LENGTH: 16
<212> TYPE: RNA
<213> ORGANISM: Homo sapiens

<400> SEQUENCE: 502
agacauaugu cugugu                                                    16

<210> SEQ ID NO 503
<211> LENGTH: 16
<212> TYPE: RNA
<213> ORGANISM: Homo sapiens

<400> SEQUENCE: 503
gacauauguc ugugug                                                    16

<210> SEQ ID NO 504
<211> LENGTH: 16
<212> TYPE: RNA
<213> ORGANISM: Homo sapiens
```

```
<400> SEQUENCE: 504
acauaugucu gugugu                                              16

<210> SEQ ID NO 505
<211> LENGTH: 16
<212> TYPE: RNA
<213> ORGANISM: Homo sapiens

<400> SEQUENCE: 505
cauaugucug ugugua                                              16

<210> SEQ ID NO 506
<211> LENGTH: 16
<212> TYPE: RNA
<213> ORGANISM: Homo sapiens

<400> SEQUENCE: 506
auaugucugu guguac                                              16

<210> SEQ ID NO 507
<211> LENGTH: 16
<212> TYPE: RNA
<213> ORGANISM: Homo sapiens

<400> SEQUENCE: 507
uaugucugug uguacg                                              16

<210> SEQ ID NO 508
<211> LENGTH: 16
<212> TYPE: RNA
<213> ORGANISM: Homo sapiens

<400> SEQUENCE: 508
augucugugu guacgc                                              16

<210> SEQ ID NO 509
<211> LENGTH: 16
<212> TYPE: RNA
<213> ORGANISM: Homo sapiens

<400> SEQUENCE: 509
ugucugugug uacgcu                                              16

<210> SEQ ID NO 510
<211> LENGTH: 16
<212> TYPE: RNA
<213> ORGANISM: Homo sapiens

<400> SEQUENCE: 510
uuuuuacggg auccau                                              16

<210> SEQ ID NO 511
<211> LENGTH: 16
<212> TYPE: RNA
<213> ORGANISM: Homo sapiens

<400> SEQUENCE: 511
uuuuacggga uccaug                                              16

<210> SEQ ID NO 512
<211> LENGTH: 16
<212> TYPE: RNA
```

```
<213> ORGANISM: Homo sapiens

<400> SEQUENCE: 512
uuuacgggau ccaugg                                               16

<210> SEQ ID NO 513
<211> LENGTH: 16
<212> TYPE: RNA
<213> ORGANISM: Homo sapiens

<400> SEQUENCE: 513
uuacgggauc caugga                                               16

<210> SEQ ID NO 514
<211> LENGTH: 16
<212> TYPE: RNA
<213> ORGANISM: Homo sapiens

<400> SEQUENCE: 514
uacgggaucc auggaa                                               16

<210> SEQ ID NO 515
<211> LENGTH: 16
<212> TYPE: RNA
<213> ORGANISM: Homo sapiens

<400> SEQUENCE: 515
acgggaucca uggaau                                               16

<210> SEQ ID NO 516
<211> LENGTH: 16
<212> TYPE: RNA
<213> ORGANISM: Homo sapiens

<400> SEQUENCE: 516
cgggauccau ggaauu                                               16

<210> SEQ ID NO 517
<211> LENGTH: 16
<212> TYPE: RNA
<213> ORGANISM: Homo sapiens

<400> SEQUENCE: 517
gggauccaug gaauug                                               16

<210> SEQ ID NO 518
<211> LENGTH: 16
<212> TYPE: RNA
<213> ORGANISM: Homo sapiens

<400> SEQUENCE: 518
ggauccaugg aauugg                                               16

<210> SEQ ID NO 519
<211> LENGTH: 16
<212> TYPE: RNA
<213> ORGANISM: Homo sapiens

<400> SEQUENCE: 519
gauccaugga auuggu                                               16

<210> SEQ ID NO 520
<211> LENGTH: 16
```

```
<212> TYPE: RNA
<213> ORGANISM: Homo sapiens

<400> SEQUENCE: 520
auccauggaa uugguu                                                        16

<210> SEQ ID NO 521
<211> LENGTH: 16
<212> TYPE: RNA
<213> ORGANISM: Homo sapiens

<400> SEQUENCE: 521
uccauggaau ugguug                                                        16

<210> SEQ ID NO 522
<211> LENGTH: 16
<212> TYPE: RNA
<213> ORGANISM: Homo sapiens

<400> SEQUENCE: 522
ccauggaauu gguugg                                                        16

<210> SEQ ID NO 523
<211> LENGTH: 16
<212> TYPE: RNA
<213> ORGANISM: Homo sapiens

<400> SEQUENCE: 523
cauggaauug guugga                                                        16

<210> SEQ ID NO 524
<211> LENGTH: 16
<212> TYPE: RNA
<213> ORGANISM: Homo sapiens

<400> SEQUENCE: 524
auggaauugg uuggau                                                        16

<210> SEQ ID NO 525
<211> LENGTH: 16
<212> TYPE: RNA
<213> ORGANISM: Homo sapiens

<400> SEQUENCE: 525
uggaauuggu uggauu                                                        16
```